(12) United States Patent
Silence et al.

(10) Patent No.: US 9,371,381 B2
(45) Date of Patent: Jun. 21, 2016

(54) SINGLE DOMAIN ANTIBODIES DIRECTED AGAINST TUMOR NECROSIS FACTOR-ALPHA AND USES THEREFOR

(71) Applicant: Ablynx N.V., Zwijnaarde (BE)

(72) Inventors: Karen Silence, Overijse (BE); Marc Jozef Lauwereys, Haaltert (BE); Hans De Haard, Oudelande (NL)

(73) Assignee: Ablynx, N.V., Zwijnaarde (BE)

( * ) Notice: Subject to any disclaimer, the term of this patent is extended or adjusted under 35 U.S.C. 154(b) by 0 days.

(21) Appl. No.: 14/529,280

(22) Filed: Oct. 31, 2014

(65) Prior Publication Data

US 2015/0110782 A1    Apr. 23, 2015

Related U.S. Application Data

(63) Continuation of application No. 12/905,589, filed on Oct. 15, 2010, now abandoned, which is a continuation of application No. 11/804,647, filed on May 18, 2007, now abandoned, which is a continuation of application No. 11/788,832, filed on Apr. 20, 2007, now abandoned, which is a continuation of application No. 11/636,300, filed on Dec. 8, 2006, now abandoned, which is a continuation of application No. 10/534,348, filed as application No. PCT/BE03/00192, filed as application No. PCT/EP03/07313, filed as application No. PCT/EP03/06581.

(60) Provisional application No. 60/425,073, filed on Nov. 8, 2002, provisional application No. 60/425,063, filed on Nov. 8, 2002.

(30) Foreign Application Priority Data

Jan. 10, 2003 (EP) .................................... 03447005

(51) Int. Cl.
| | |
|---|---|
| *C07K 16/24* | (2006.01) |
| *C07K 16/18* | (2006.01) |
| *C07K 16/28* | (2006.01) |
| *C07K 16/36* | (2006.01) |
| *C07K 16/40* | (2006.01) |
| *C07K 16/42* | (2006.01) |
| *A61K 39/00* | (2006.01) |

(52) U.S. Cl.
CPC .............. *C07K 16/241* (2013.01); *C07K 16/18* (2013.01); *C07K 16/249* (2013.01); *C07K 16/2863* (2013.01); *C07K 16/2875* (2013.01); *C07K 16/36* (2013.01); *C07K 16/40* (2013.01); *C07K 16/4291* (2013.01); *A61K 2039/505* (2013.01); *C07K 2317/22* (2013.01); *C07K 2317/24* (2013.01); *C07K 2317/31* (2013.01); *C07K 2317/34* (2013.01); *C07K 2317/565* (2013.01); *C07K 2317/569* (2013.01); *C07K 2317/626* (2013.01); *C07K 2317/76* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,405,306 A | 9/1983 | Pritchard et al. |
| 5,091,513 A | 2/1992 | Huston et al. |
| 5,196,193 A | 3/1993 | Carroll |
| 5,487,890 A | 1/1996 | Taylor et al. |
| 5,637,038 A | 6/1997 | Davis |
| 5,644,034 A | 7/1997 | Rathjen et al. |
| 5,656,273 A | 8/1997 | Amiri et al. |
| 5,672,347 A | 9/1997 | Aggarwal et al. |
| 5,837,243 A | 11/1998 | Deo et al. |
| 5,843,440 A | 12/1998 | Pouletty et al. |
| 5,891,996 A | 4/1999 | Mateo de Acosta del Rio et al. |
| 5,942,602 A | 8/1999 | Wels et al. |
| 5,976,532 A | 11/1999 | Coller et al. |
| 5,994,511 A | 11/1999 | Lowman et al. |
| 6,066,718 A | 5/2000 | Hardman et al. |
| 6,251,393 B1 | 6/2001 | Handin |
| 6,419,934 B1 | 7/2002 | Tobinick |
| 6,504,013 B1 | 1/2003 | Lawton et al. |
| 6,670,453 B2 | 12/2003 | Frenken et al. |
| 6,759,518 B1 | 7/2004 | Kontermann et al. |
| 6,838,254 B1 | 1/2005 | Hamers et al. |
| 6,902,734 B2 | 6/2005 | Giles-Komar et al. |
| 7,084,257 B2 | 8/2006 | Deshpande et al. |
| 7,300,655 B2 | 11/2007 | Hansen et al. |
| 7,368,111 B2 | 5/2008 | Thompson et al. |
| 7,589,180 B2 | 9/2009 | Old et al. |

(Continued)

FOREIGN PATENT DOCUMENTS

| | | |
|---|---|---|
| EP | 0 288 088 A2 | 10/1988 |
| EP | 0 366 043 A1 | 5/1990 |

(Continued)

OTHER PUBLICATIONS

Annex to Summons to Attend Oral Proceedings dated May 7, 2009.

(Continued)

*Primary Examiner* — Gregory S Emch
(74) *Attorney, Agent, or Firm* — Wolf, Greenfield & Sacks, P.C.

(57) ABSTRACT

The present invention relates to polypeptides derived from single domain heavy chain antibodies directed to Tumor Necrosis Factor-alpha. It further relates to single domain antibodies that are *Camelidae* VHHs. It further relates to methods of administering said polypeptides. It further relates to protocols for screening for agents that modulate the TNF-alpha receptor, and the agents resulting from said screening.

16 Claims, 10 Drawing Sheets

(56) References Cited

U.S. PATENT DOCUMENTS

Figure 2:
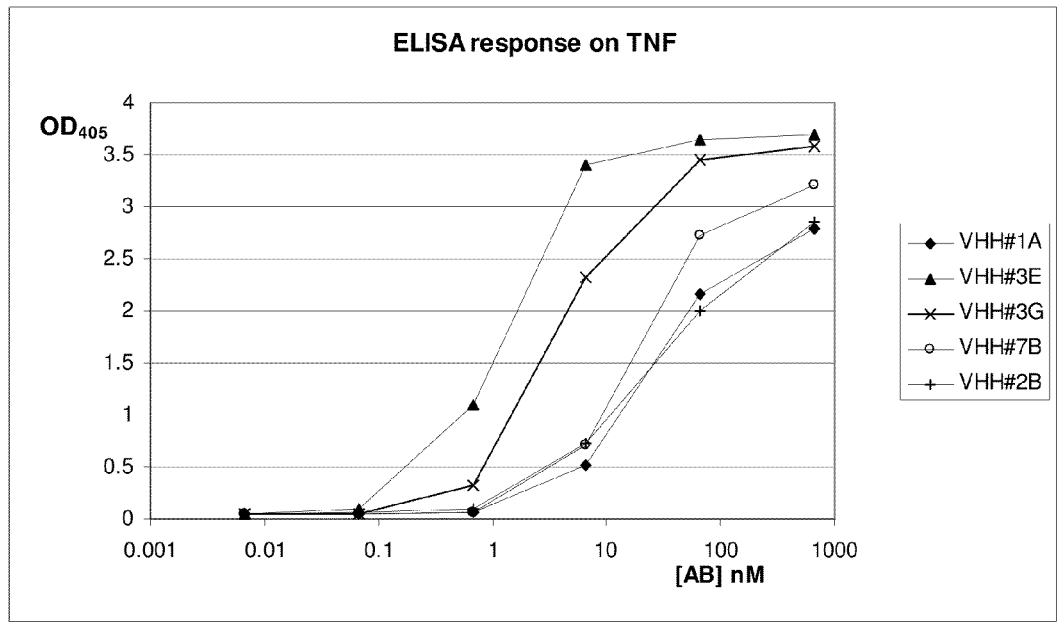

| | | |
|---|---|---|
| 7,598,350 B2 | 10/2009 | Liu et al. |
| 7,822,540 B2 | 10/2010 | Fukaya et al. |
| 7,897,151 B2 | 3/2011 | Morsey et al. |
| 8,097,251 B2 | 1/2012 | Muyldermans et al. |
| 8,188,223 B2 | 5/2012 | Beirnaert et al. |
| 8,217,140 B2 | 7/2012 | Revets et al. |
| 8,703,131 B2 | 4/2014 | Beirnaert |
| 2001/0024647 A1 | 9/2001 | Handin |
| 2002/0001587 A1 | 1/2002 | Erickson et al. |
| 2002/0009453 A1 | 1/2002 | Haurum et al. |
| 2002/0028204 A1 | 3/2002 | Nagano et al. |
| 2002/0052479 A1 | 5/2002 | Anderson et al. |
| 2002/0054878 A1 | 5/2002 | Lowman et al. |
| 2002/0058033 A1 | 5/2002 | Raisch et al. |
| 2002/0076404 A1 | 6/2002 | Chang |
| 2002/0132275 A1 | 9/2002 | Fidler et al. |
| 2002/0165387 A1 | 11/2002 | Anderson et al. |
| 2003/0088074 A1 | 5/2003 | Hamers et al. |
| 2003/0092892 A1 | 5/2003 | Frenken et al. |
| 2003/0118592 A1 | 6/2003 | Ledbetter et al. |
| 2004/0063912 A1 | 4/2004 | Blumberg et al. |
| 2004/0180046 A1 | 9/2004 | Himawan |
| 2004/0197326 A1 | 10/2004 | Fick et al. |
| 2004/0219643 A1 | 11/2004 | Winter et al. |
| 2004/0253638 A1 | 12/2004 | Casterman et al. |
| 2005/0054001 A1 | 3/2005 | Muyldermans |
| 2006/0034833 A1 | 2/2006 | Beirnaert |
| 2006/0034845 A1 | 2/2006 | Silence et al. |
| 2006/0115470 A1 | 6/2006 | Silence et al. |
| 2006/0228355 A1 | 10/2006 | Laeremans et al. |
| 2007/0031424 A1 | 2/2007 | Muyldermans |
| 2007/0077249 A1 | 4/2007 | Silence et al. |
| 2007/0178082 A1 | 8/2007 | Silence et al. |
| 2007/0237769 A1 | 10/2007 | Silence et al. |
| 2007/0264253 A1 | 11/2007 | Liu et al. |
| 2009/0022721 A1 | 1/2009 | Silence et al. |
| 2009/0238829 A1 | 9/2009 | Silence et al. |
| 2009/0324512 A1 | 12/2009 | Silence et al. |
| 2010/0003248 A1 | 1/2010 | Silence et al. |
| 2010/0003249 A1 | 1/2010 | Silence et al. |
| 2010/0003253 A1 | 1/2010 | Laeremans et al. |
| 2010/0021459 A1 | 1/2010 | Silence et al. |
| 2010/0040613 A1 | 2/2010 | Silence et al. |
| 2011/0027281 A1 | 2/2011 | Silence et al. |
| 2011/0123529 A1 | 5/2011 | Laeremans et al. |
| 2011/0178277 A1 | 7/2011 | Silence et al. |
| 2011/0184145 A1 | 7/2011 | Silence et al. |
| 2011/0184150 A1 | 7/2011 | Silence et al. |
| 2011/0184151 A1 | 7/2011 | Laeremans et al. |
| 2012/0202977 A1 | 8/2012 | Silence et al. |
| 2012/0251540 A1 | 10/2012 | Silence et al. |
| 2013/0136744 A1 | 5/2013 | Bouche et al. |
| 2015/0064182 A1 | 3/2015 | Silence et al. |

FOREIGN PATENT DOCUMENTS

| | | |
|---|---|---|
| EP | 0 368 684 A1 | 5/1990 |
| EP | 0 476 226 A1 | 3/1992 |
| EP | 0 584 421 A1 | 3/1994 |
| EP | 0 589 840 A1 | 3/1994 |
| EP | 0 614 984 A2 | 9/1994 |
| EP | 0 952 218 A2 | 10/1999 |
| EP | 0 954 978 A1 | 11/1999 |
| EP | 1 002 861 A1 | 5/2000 |
| EP | 1 118 669 A1 | 7/2001 |
| EP | 1 134 231 A1 | 9/2001 |
| EP | 1 517 921 | 3/2005 |
| GB | 0115841.9 | 6/2001 |
| GB | 0230202.4 | 12/2002 |
| JP | 62175426 A | 8/1987 |
| JP | 01-268645 | 10/1989 |
| JP | H11-503918 | 4/1999 |
| WO | WO 89/06138 A1 | 7/1989 |
| WO | WO 90/05144 A1 | 5/1990 |
| WO | WO 90/10707 A1 | 9/1990 |
| WO | WO 91/01743 A1 | 2/1991 |
| WO | WO 91/02078 A1 | 2/1991 |
| WO | WO 91/04054 A1 | 4/1991 |
| WO | WO 92/01787 A1 | 2/1992 |
| WO | WO 92/16142 A1 | 10/1992 |
| WO | WO 93/04173 A1 | 3/1993 |
| WO | WO 94/04678 A1 | 3/1994 |
| WO | WO 94/12531 A1 | 6/1994 |
| WO | WO 95/10302 A1 | 4/1995 |
| WO | WO 95/17673 A1 | 6/1995 |
| WO | WO 96/32478 A1 | 10/1996 |
| WO | WO 96/34096 A1 | 10/1996 |
| WO | WO 96/34103 A1 | 10/1996 |
| WO | WO 96/40210 A1 | 12/1996 |
| WO | WO 97/10846 A1 | 3/1997 |
| WO | WO 97/17207 A1 | 5/1997 |
| WO | WO 97/29131 A1 | 8/1997 |
| WO | WO 98/34645 A1 | 8/1998 |
| WO | WO 98/40469 A1 | 9/1998 |
| WO | WO 99/02078 A1 | 1/1999 |
| WO | WO 99/09055 A2 | 2/1999 |
| WO | WO 99/23221 A2 | 5/1999 |
| WO | WO 99/46300 A1 | 9/1999 |
| WO | WO 99/64069 A1 | 12/1999 |
| WO | WO 00/29004 A1 | 5/2000 |
| WO | WO 00/29442 A1 | 5/2000 |
| WO | WO 00/40262 A1 | 7/2000 |
| WO | WO 00/56772 A2 | 9/2000 |
| WO | WO 00/65057 A1 | 11/2000 |
| WO | WO 01/19871 A2 | 3/2001 |
| WO | WO 01/45746 A2 | 6/2001 |
| WO | WO 01/58956 A2 | 8/2001 |
| WO | WO 01/89567 A1 | 11/2001 |
| WO | WO 02/12502 A2 | 2/2002 |
| WO | WO 02/48193 A2 | 6/2002 |
| WO | WO 02/051351 A1 | 7/2002 |
| WO | WO 02/057445 A1 | 7/2002 |
| WO | WO 02/078598 A2 | 10/2002 |
| WO | WO 02/079781 A1 | 10/2002 |
| WO | WO 02/080967 A1 | 10/2002 |
| WO | WO 02/081649 A2 | 10/2002 |
| WO | WO 03/002609 A2 | 1/2003 |
| WO | WO 03/035694 A2 | 5/2003 |
| WO | WO 03/077834 A2 | 9/2003 |
| WO | WO 2004/003019 A2 | 1/2004 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/081026 A2 | 9/2004 |
| WO | WO 2006/056306 A2 | 6/2006 |
| WO | WO 2006/059108 A2 | 6/2006 |
| WO | WO 2007/066109 A1 | 6/2007 |
| WO | WO 2009/074634 A2 | 6/2009 |

OTHER PUBLICATIONS

Annex to the Decision Revoking European Patent No. EP 1 517 921—Grounds for the Decision to Revoke European Patent No. EP 1 517 921 filed Apr. 8, 2010.
Annex to the Decision Revoking European Patent No. EP 1 517 921—Opposition. Apr. 8, 2010.
Annex to the Decision Revoking European Patent No. EP 1 517 921. Apr. 8, 2010.
Applicant's Remarks for Reply to Written Opinion filed Apr. 28, 2006.
Auxiliary Request 1 filed by patentee on Jul. 30, 2010.
Auxiliary Request 2 filed by patentee on Jul. 30, 2010.
Auxiliary Request 3 filed by patentee on Jul. 30, 2010.
Decision Revoking European Patent No. EP 1 517 921. Letter dated Apr. 8, 2010.
Filing of a New Opposition in EP 1 517 921. Filed on Mar. 6, 2007.
Letter of Opponent dated Apr. 15, 2008 in opposition to EP 1 517 921 and in response to Patentee's Letter of Oct. 30, 2007.
Letter of Opponent dated May 28, 2008 in opposition to EP 1 517 921 and in response to Patentee's Letter of Oct. 30, 2007.

(56) References Cited

OTHER PUBLICATIONS

Letter of opponent regarding the opposition procedure filed in the opposition to EP 1 517 921 on Mar. 30, 2009.
Letter of Opponent regarding the Opposition Procedure in EP 1 517 921 dated Sep. 25, 2009.
Letter of Opponent regarding the Opposition Procedure in EP 1 517 921 filed by opponent. Dec. 10, 2009.
Letter of Patentee dated Oct. 13, 2008 in EP 1 517 921.
Letter of Patentee regarding the Opposition Procedure for EP 1 517 921 filed May 19, 2009.
Main Request filed by Patentee on Jul. 30, 2010.
Notice of Opposition in EP 1 517 921. Filed on Mar. 6, 2007.
Official Action concerning European application No. 03 775 004.9 dated Jan. 22, 2007.
Official Action concerning European application No. 03 776 677 dated Jun. 5, 2009.
Official Action concerning European application No. 06 006 277 dated May 29, 2009.
Reply of the patent proprietor to the notices of opposition dated Oct. 30, 2007.
Response to Patentee's Grounds of Appeal, dated Feb. 25, 2011.
Statement of Grounds of Appeal filed by patentee on Jul. 30, 2010.
Summary of telephone consultation in European Application No. 06 006 277.5, submitted in EP 1 517 921 on Sep. 25, 2009.
Third party observations in the Opposition Proceedings concerning European patent EP 1 517 921 in the name of Domantis Limited. Barcelona. Sep. 1, 2009.
Third party observations in the Opposition Proceedings concerning European patent EP 1 517 921 in the name of Domantis Limited. Munich. Jun. 17, 2009.
Third party observations in the Opposition Proceedings concerning European patent EP 1 517 921 in the name of Domantis Limited. Munich. Nov. 28, 2008.
Third party observations in the Opposition Proceedings concerning European patent EP 1 517 921 in the name of Domantis Limited. Paris. Sep. 4, 2009.
[No Author Listed] Ablynx, Protocol for affinity determination of the single immunoglobulin variable domains MSA-16 and MSA-26 as described in EP 1 517 921 B1 to mouse, rat, rabbit and human serum albumin via surface plasmon resonance (Biacore).
[No Author Listed] Domain antibodies. http://www.domantis com/domain.htm. Accessed on Oct. 28, 2009.
[No Author Listed] Domantis and Peptech announce outstanding pre-clinical results for their anti-TNF domain antibody in rheumatoid arthritis. Last accessed on May 25, 2012 at http://web.archive.org/web/20030907213244/http://www.domantis com/press_pf.asp?id=27.
[No Author Listed] Immunochemistry. Nankodo Co., Ltd., Jul. 15, 1983 (1st ed.), pp. 35-36.
[No Author Listed] Letter from D. Young & Co. regarding EP 1 558 650 Third Party Observations dated Sep. 12, 2007.
[No Author Listed] Letters from D. Young & Co. regarding opposition to EP 0656946 dated May 18, 2007 and Jun. 5, 2007.
[No Author Listed] Non-Patent Literature cited during the appeal procedure. Reference D53.
[No Author Listed] Non-Patent Literature cited during the appeal procedure. Reference D54.
[No Author Listed] Omalizumab: anti-IgE monoclonal antibody E25, E25, humanised anti-IgE MAb, IGE 025, monoclonal antibody E25, Olizumab, Xolair, rhuMAb-E25. BioDrugs. 2002;16(5):380-6.
[No Author Listed] Patentee's Letter regarding EP 05076402.6 dated Sep. 25, 2006.
[No Author Listed] Patentee's Letter regarding EP 03776677.1 dated Dec. 23, 2005.
[No Author Listed] The Gale Encyclopedia of Medicine. Olenderf et al., eds. 1999;1:419.
Adams et al., Generating improved single-chain Fv molecules for tumor targeting. J Immunol Methods. Dec. 10, 1999;231(1-2):249-60.

Adriouch et al., Probing the expression and function of the P2X7 purinoceptor with antibodies raised by genetic immunization. Cell Immunol. Jul.-Aug. 2005;236(1-2):72-7. Epub Sep. 12, 2005.
Amagai, Autoimmunity against desmosomal cadherins in pemphigus. J Dermatol Sci. Jun. 1999;20(2):92-102. Review.
Arbabi Ghahroudi et al., Selection and identification of single domain antibody fragments from camel heavy-chain antibodies. FEBS Lett. Sep. 15, 1997;414(3):521-6.
Baniyash et al., Inhibition of IgE binding to mast cells and basophils by monoclonal antibodies to murine IgE. Eur J Immunol. Sep. 1984;14(9):799-807.
Barrios et al., Length of the antibody heavy chain complementarity determining region 3 as a specificity-determining factor. J Mol Recognit. Jul.-Aug. 2004;17(4):332-8.
Bass et al., Molecular basis of age-dependent gastric inactivation of rhesus rotavirus in the mouse. J Clin Invest. Jun. 1992;89(6):1741-5.
Becerril et al., Toward selection of internalizing antibodies from phage libraries. Biochem Biophys Res Commun. Feb. 16, 1999;255(2):386-93.
Bins et al., A rapid and potent DNA vaccination strategy defined by in vivo monitoring of antigen expression. Nat Med. Aug. 2005;11(8):899-904. Epub Jun. 19, 2005.
Bins et al., In vivo antigen stability affects DNA vaccine immunogenicity. J Immunol. Aug. 15, 2007;179(4):2126-33.
Birkett, Chapter 3: Half-life. In Pharmacokinetics Made Easy. 2004:16-24.
Bogdan et al., Epidermal growth factor receptor signaling. Curr Biol. Apr. 17, 2001;11(8):R292-5.
Boulougouris et al., Epidermal growth factor receptor structure, regulation, mitogenic signalling and effects of activation. Anticancer Res. Jul.-Aug. 2001;21(4A):2769-75.
Cataldo et al., Matrix metalloproteinase-9 deficiency impairs cellular infiltration and bronchial hyperresponsiveness during allergen-induced airway inflammation. Am J Pathol. Aug. 2002;161(2):491-8.
Chang, The pharmacological basis of anti-IgE therapy. Nat Biotechnol. Feb. 2000;18(2):157-62.
Chen et al., TTD: Therapeutic Target Database. Nucleic Acids Res. Jan. 1, 2002;30(1):412-5.
Cheong et al., Affinity enhancement of bispecific antibody against two different epitopes in the same antigen. Biochem Biophys Res Commun. Dec. 31, 1990;173(3):795-800.
Chuang et al., Pharmaceutical strategies utilizing recombinant human serum albumin. Pharm Res. May 2002;19(5):569-77.
Cochran et al., Domain-level antibody epitope mapping through yeast surface display of epidermal growth factor receptor fragments. J Immunol Methods. Apr. 2004;287(1-2):147-58.
Colman, Effects of amino acid sequence changes on antibody-antigen interactions. Res Immunol. Jan. 1994;145(1):33-6.
Connelly, Fully human domain antibody therapeutics: the best of both worlds. Innovations in Pharmaceutical Technology. 2005;42-5.
Conrath et al., Beta-lactamase inhibitors derived from single-domain antibody fragments elicited in the camelidae. Antimicrob Agents Chemother. Oct. 2001;45(10):2807-12.
Conrath et al., Camel single-domain antibodies as modular building units in bispecific and bivalent antibody constructs. J Biol Chem. Mar. 9, 2001;276(10):7346-50.
Cortez-Retamozo et al., Efficient tumor targeting by single-domain antibody fragments of camels. Int J Cancer. Mar. 20, 2002;98(3):456-62.
Crombet-Ramos et al., Antiproliferative, antiangiogenic and proapoptotic activity of h-R3: A humanized anti-EGFR antibody. Int J Cancer. Oct. 20, 2002;101(6):567-75.
Crowe et al., Recombinant human respiratory syncytial virus (RSV) monoclonal antibody Fab is effective therapeutically when introduced directly into the lungs of RSV-infected mice. Proc Natl Acad Sci U S A. Feb. 15, 1994;91(4):1386-90.
Curriculum Vitae of Professor Roland E. Konterman.
D'Haens et al., Endoscopic and histological healing with infliximab anti-tumor necrosis factor antibodies in Crohn's disease: A European multicenter trial. Gastroenterology. May 1999;116(5):1029-34.
Davies et al., 'Camelising' human antibody fragments: NMR studies on VH domains. FEBS Lett. Feb. 21, 1994;339(3):285-90.

(56) References Cited

OTHER PUBLICATIONS

Davies et al., Antibody VH domains as small recognition units. Biotechnology (N Y). May 1995;13(5):475-9.
Davis et al., 508.1 Anatomy of the Glomerulus. Nelson Textbook of Pediatrics, 18th edition, 2007. Part XXII—Nephrology, Section 1—Glomerular Disease:2163.
Declaration of Dr. Felix Kratz, Feb. 21, 2011.
Declaration of Professor Per-Ake Nygren, Feb. 22, 2011.
Declaration of Professor Roland E. Konterman. Filed in opposition to EP 1517921. Dec. 3, 2009.
Dennis et al., Albumin binding as a general strategy for improving the pharmacokinetics of proteins. J Biol Chem. Sep. 20, 2002;277(38):35035-43. Epub Jul. 15, 2002.
Desmyter et al., Antigen specificity and high affinity binding provided by one single loop of a camel single-domain antibody. J Biol Chem. Jul. 13, 2001;276(28):26285-90. Epub May 7, 2001.
Desmyter et al., Three camelid VHH domains in complex with porcine pancreatic alpha-amylase. Inhibition and versatility of binding topology. J Biol Chem. Jun. 28, 2002;277(26):23645-50. Epub Apr. 17, 2002.
Dolk et al., Isolation of llama antibody fragments for prevention of dandruff by phage display in shampoo. Appl Environ Microbiol. Jan. 2005;71(1):442-50.
Drejer et al., Receptor binding and tyrosine kinase activation by insulin analogues with extreme affinities studied in human hepatoma HepG2 cells. Diabetes. Nov. 1991;40(11):1488-95.
Dubnovitsky et al., Expression, refolding, and ferritin-binding activity of the isolated VL-domain of monoclonal antibody F11. Biochemistry (Mosc). Sep. 2000;65(9):1011-8.
Ebina et al., Passive immunizations of suckling mice and infants with bovine colostrum containing antibodies to human rotavirus. J Med Virol. Oct. 1992;38(2):117-23.
Fahrner et al., Industrial purification of pharmaceutical antibodies: development, operation, and validation of chromatography processes. Biotechnol Genet Eng Rev. 2001;18:301-27. Review.
Fahy et al., Effect of aerosolized anti-IgE (E25) on airway responses to inhaled allergen in asthmatic subjects. Am J Respir Crit Care Med. Sep. 1999;160(3):1023-7.
Fan et al., Three-dimensional structure of an Fv from a human IgM immunoglobulin. J Mol Biol. Nov. 5, 1992;228(1):188-207.
Fendly et al., Murine monoclonal antibodies defining neutralizing epitopes on tumor necrosis factor. Hybridoma. Aug. 1987;6(4):359-70.
Frenken et al., Isolation of antigen specific llama VHH antibody fragments and their high level secretion by *Saccharomyces cerevisiae*. J Biotechnol. Feb. 28, 2000;78(1):11-21.
Guarino et al., Oral immunoglobulins for treatment of acute rotaviral gastroenteritis. Pediatrics. Jan. 1994;93(1):12-6.
Haber et al., Extensive degradation of antibody by pepsin. Biochemistry. Jul. 1967;6(7):1974-80.
Hamilton-Wessler et al., Mechanism of protracted metabolic effects of fatty acid acylated insulin, NN304, in dogs: retention of NN304 by albumin. Diabetologia. Oct. 1999;42(10):1254-63.
Harmsen et al., *Escherichia coli* F4 fimbriae specific llama single-domain antibody fragments effectively inhibit bacterial adhesion in vitro but poorly protect against diarrhoea. Vet Microbiol. Nov. 30, 2005;111(1-2):89-98. Epub Oct. 10, 2005.
Harmsen et al., Llama heavy-chain V regions consist of at least four distinct subfamilies revealing novel sequence features. Mol Immunol. Aug. 2000;37(10):579-90.
Harmsen et al., Prolonged in vivo residence times of llama single-domain antibody fragments in pigs by binding to porcine immunoglobulins. Vaccine. Sep. 30, 2005;23(41):4926-34.
Harmsen et al., Selection and optimization of proteolytically stable llama single-domain antibody fragments for oral immunotherapy. Appl Microbiol Biotechnol. Sep. 2006;72(3):544-51. Epub Feb. 1, 2006.
Heitner et al., Selection of cell binding and internalizing epidermal growth factor receptor antibodies from a phage display library. J Immunol Methods. Feb. 1, 2001;248(1-2):17-30.

Heusser et al., New concepts of IgE regulation. Int Arch Allergy Appl Immunol. 1991;94(1-4):87-90.
Hey et al., Artificial, non-antibody binding proteins for pharmaceutical and industrial applications. Trends Biotechnol. Oct. 2005;23(10):514-22.
Holliger et al., Retargeting serum immunoglobulin with bispecific diabodies. Nat Biotechnol. Jul. 1997;15(7):632-6.
Holm et al., Functional mapping and single chain construction of the anti-cytokeratin 8 monoclonal antibody TS1. Mol Immunol. Feb. 2007;44(6):1075-84. Epub Sep. 20, 2006.
Holt et al., Domain antibodies: proteins for therapy. Trends Biotechnol. Nov. 2003;21(11):484-90.
Hoogenboom, Mix and match: building manifold binding sites. Nat Biotechnol. Feb. 1997;15(2):125-6.
Hori et al., Effect of orally administered enterotoxigenic *Escherichia coli* K99-specific monoclonal antibody to neonatal calves. Journal of the Japan Veterinary Medical Association. 1989;42(6):411-16. Abstract Only.
Hulme et al., The measurement of renal permeability using labelled marcromolecules. Proc R Soc Med. Jun. 1966;59(6):509-12.
Janeway et al., Immunobiology. 3rd Edition. 1997. Garland Press. 11:11.
Janeway et al., Immunobiology. 3rd Edition. 1997. Garland Press. 2:2-2:5; 3.1-3.11; 11.1.
Janeway et al., Immunobiology. 3rd Edition. 1997. Garland Press. 3:1-3:11.
Janeway et al., Immunobiology. 3rd Edition. 1997. Garland Press. 2:19-2:20.
Kang et al., Anti-EGFR monoclonal antibody Cetuximab binds the EGFR variant III receptor and internalizes phosphorylated receptor on the cell surface. Eur. J. Cancer. 38:S149.
Kilpatrick et al., Gene gun delivered DNA-based immunizations mediate rapid production of murine monoclonal antibodies to the Flt-3 receptor. Hybridoma. Dec. 1998;17(6):569-76.
King, Applications and Engineering of Monoclonal Antibodies. Taylor and Francis Ltd, 1998:40-50.
Knudsen et al., Potent derivatives of glucagon-like peptide-1 with pharmacokinetic properties suitable for once daily administration. J Med Chem. May 4, 2000;43(9):1664-9.
Koch-Nolte et al., Single domain antibodies from llama effectively and specifically block T cell ecto-ADP-ribosyltransferase ART2.2 in vivo. FASEB J. Nov. 2007;21(13):3490-8. Epub Jun. 15, 2007.
Kolbinger et al., Humanization of a mouse anti-human IgE antibody: a potential therapeutic for IgE-mediated allergies. Protein Eng. Nov. 1993;6(8):971-80.
Koumenis et al., Modulating pharmacokinetics of an anti-interleukin-8 F(ab')(2) by amine-specific PEGylation with preserved bioactivity. Int J Pharm. Mar. 30, 2000;198(1):83-95.
Kruger et al., Therapeutic effect of llama derived VHH fragments against *Streptococcus* mutans on the development of dental caries. Appl Microbiol Biotechnol. Oct. 2006;72(4):732-7. Epub Apr. 25, 2006.
Kuo et al., Topical antibody delivery systems produce sustained levels in mucosal tissue and blood. Nat Biotechnol. Feb. 1998;16(2):163-7.
Kurtzhals et al., Albumin binding and time action of acylated insulins in various species. J Pharm Sci. Mar. 1996;85(3):304-8.
Kurtzhals et al., Albumin binding of insulins acylated with fatty acids: characterization of the ligand-protein interaction and correlation between binding affinity and timing of the insulin effect in vivo. Biochem J. Dec. 15, 1995;312 ( Pt 3):725-31.
Lauwereys et al., Potent enzyme inhibitors derived from dromedary heavy-chain antibodies. EMBO J. Jul. 1, 1998;17(13):3512-20.
Lederman et al., A single amino acid substitution in a common African allele of the CD4 molecule ablates binding of the monoclonal antibody, OKT4. Mol Immunol. Nov. 1991;28(11):1171-81.
Lewis et al., Immunoglobulin complementarity-determining region grafting by recombinant polymerase chain reaction to generate humanised monoclonal antibodies. Gene. May 30, 1991;101(2):297-302.
Lorimer et al., Mutant epidermal growth factor receptors as targets for cancer therapy. Curr Cancer Drug Targets. Jun. 2002;2(2):91-102. Review.

(56) References Cited

OTHER PUBLICATIONS

Losonsky et al., Oral administration of human serum immunoglobulin in immunodeficient patients with viral gastroenteritis. A pharmacokinetic and functional analysis. J Clin Invest. Dec. 1985;76(6):2362-7.

Maccallum et al., Antibody-antigen interactions: contact analysis and binding site topography. J Mol Biol. Oct. 11, 1996;262(5):732-45.

Macewan, TNF ligands and receptors—a matter of life and death. Br J Pharmacol. Feb. 2002;135(4):855-75.

Mallender et al., Construction, expression, and activity of a bivalent bispecific single-chain antibody. J Biol Chem. Jan. 7, 1994;269(1):199-206.

Mamot et al., Epidermal growth factor receptor (EGFR)-targeted immunoliposomes mediate specific and efficient drug delivery to EGFR- and EGFRvIII-overexpressing tumor cells. Cancer Res. Jun. 15, 2003;63(12):3154-61.

Mauri et al., Prevention of arthritis by interleukin 10-producing B cells. J Exp Med. Feb. 17, 2003;197(4):489-501.

Melamed et al., Benefit of oral immune globulin therapy in patients with immunodeficiency and chronic diarrhea. J Pediatr. Sep. 1991;119(3):486-9.

Mitri et al., Inhaled insulin—what went wrong. Nat Clin Pract Endocrinol Metab. Jan. 2009;5(1):24-5. doi: 10.1038/ncpendmet1007. Epub Nov. 4, 2008.

Miyajima et al., Rat monoclonal anti-murine IgE antibody removes IgE molecules already bound to mast cells or basophilic leukemia cells, resulting in the inhibition of systemic anaphylaxis and passive cutaneous anaphylaxis. Int Arch Allergy Immunol. May 2002;128(1):24-32.

Moghal et al., Multiple positive and negative regulators of signaling by the EGF-receptor. Curr Opin Cell Biol. Apr. 1999;11(2):190-6.

Morelli et al., Oral administration of anti-doxorubicin monoclonal antibody prevents chemotherapy-induced gastrointestinal toxicity in mice. Cancer Res. May 1, 1996;56(9):2082-5.

Murthy et al., Combination therapy of pentoxifylline and TNFalpha monoclonal antibody in dextran sulphate-induced mouse colitis. Aliment Pharmacol Ther. Feb. 1999;13(2):251-60.

Muruganandam et al., Selection of phage-displayed llama single-domain antibodies that transmigrate across human blood-brain barrier endothelium. FASEB J. Feb. 2002;16(2):240-2. Epub Dec. 28, 2001.

Muyldermans et al., Recognition of antigens by single-domain antibody fragments: the superfluous luxury of paired domains. Trends Biochem Sci. Apr. 2001;26(4):230-5.

Muyldermans et al., Unique single-domain antigen binding fragments derived from naturally occurring camel heavy-chain antibodies. J Mol Recognit. Mar.-Apr. 1999;12(2):131-40.

Muyldermans, Single domain camel antibodies: current status. J Biotechnol. Jun. 2001;74(4):277-302.

Myers et al., Acylation of human insulin with palmitic acid extends the time action of human insulin in diabetic dogs. Diabetes. Apr. 1997;46(4):637-42.

Nagatomi et al., [Absorption of the antibody formation to anticartilage-antiparathyroid antibodies administered into the rectum (author's transl)]. Nihon Yakurigaku Zasshi. Aug. 1981;78(2):109-15. Japanese.

Nagatomi et al., Antigen-binding activity and allergenicity of heterologous gamma-globulin absorbed from the rectum. Int Arch Allergy Appl Immunol. 1980;63(3):340-3.

Nilsson et al., Affinity fusion strategies for detection, purification, and immobilization of recombinant proteins. Protein Expr Purif. Oct. 1997;11(1):1-16.

Nuttall et al., Immunoglobulin VH domains and beyond: design and selection of single-domain binding and targeting reagents. Curr Pharm Biotechnol. Nov. 2000;1(3):253-63.

Nygren et al., in vivo stabilization of a human recombinant CD4 derivative by fusion to a serum-albumin-binding receptor. Vaccines. 1991;91:363-8.

Pant et al., Lactobacilli expressing variable domain of llama heavy-chain antibody fragments (lactobodies) confer protection against rotavirus-induced diarrhea. J Infect Dis. Dec. 1, 2006;194(11):1580-8. Epub Oct. 23, 2006.

Pant et al., Lactobacilli producing bispecific llama-derived anti-rotavirus proteins in vivo for rotavirus-induced diarrhea. Future Microbiol. May 2011;6(5):583-93.

Patton, Breathing life into protein drugs. Nat Biotechnol. Feb. 1998;16(2):141-3.

Paul, Fv structure and diversity in three dimensions. Fundamental immunology, 3rd Edition, 1993:292-295.

Poul et al., Selection of tumor-specific internalizing human antibodies from phage libraries. J Mol Biol. Sep. 1, 2000;301(5):1149-61.

Presta et al., Generation of a humanized, high affinity anti-tissue factor antibody for use as a novel antithrombotic therapeutic. Thromb Haemost. Mar. 2001;85(3):379-89.

Prince et al., Effectiveness of topically administered neutralizing antibodies in experimental immunotherapy of respiratory syncytial virus infection in cotton rats. J Virol. Jun. 1987;61(6):1851-4.

Prince et al., Mechanism of antibody-mediated viral clearance in immunotherapy of respiratory syncytial virus infection of cotton rats. J Virol. Jun. 1990;64(6):3091-2.

Queen et al., A humanized antibody that binds to the interleukin 2 receptor. Proc Natl Acad Sci U S A. Dec. 1989;86(24):10029-33.

Radomsky et al., Controlled vaginal delivery of antibodies in the mouse. Biol Reprod. Jul. 1992;47(1):133-40.

Reeck et al., "Homology" in proteins and nucleic acids: a terminology muddle and a way out of it. Cell. Aug. 28, 1987;50(5):667.

Reilly et al., Oral delivery of antibodies. Future pharmacokinetic trends. Clin Pharmacokinet. Apr. 1997;32(4):313-23.

Reiter et al., An antibody single-domain phage display library of a native heavy chain variable region: isolation of functional single-domain VH molecules with a unique interface. Mol Biol. Jul. 16, 1999;290(3):685-98.

Reiter et al., Engineering antibody Fv fragments for cancer detection and therapy: disulfide-stabilized Fv fragments. Nat Biotechnol. Oct. 1996;14(10):1239-45.

Rheinnecker et al., Multivalent antibody fragments with high functional affinity for a tumor-associated carbohydrate antigen. J Immunol. Oct. 1, 1996;157(7):2989-97.

Riechmann et al., Reshaping human antibodies for therapy. Nature. Mar. 24, 1988;332(6162):323-7.

Riechmann et al., Single domain antibodies: comparison of camel VH and camelised human VH domains. J Immunol Methods. Dec. 10, 1999;231(1-2):25-38.

Riemer et al., Matching of trastuzumab (Herceptin) epitope mimics onto the surface of Her-2/neu—a new method of epitope definition. Mol Immunol. May 2005;42(9):1121-4. Epub Jan. 8, 2005.

Roovers et al., Efficient inhibition of EGFR signaling and of tumour growth by antagonistic anti-EFGR Nanobodies. Cancer Immunol Immunother. Mar. 2007;56(3):303-317.

Rosenberg, Effects of protein aggregates: an immunologic perspective. AAPS J. Aug. 4, 2006;8(3):E501-7.

Rote et al., Antithrombotic effects of DMP 728, a platelet GPIIb/IIIa receptor antagonist, in a canine model of arterial thrombosis. J Cardiovasc Pharmacol. Apr. 1994;23(4):681-9.

Rudikoff et al., Single amino acid substitution altering antigen-binding specificity. Proc Natl Acad Sci U S A. Mar. 1982;79(6):1979-83.

Saelman et al., Platelet adhesion to collagen types I through VIII under conditions of stasis and flow is mediated by GPIa/IIa (alpha 2 beta 1-integrin). Blood. Mar. 1, 1994;83(5):1244-50.

Saerens et al., Identification of a universal VHH framework to graft non-canonical antigen-binding loops of camel single-domain antibodies. J Mol Biol. Sep. 23, 2005;352(3):597-607.

Saltzman et al., Long-term vaginal antibody delivery: delivery systems and biodistribution. Biotechnol Bioeng. Feb. 5, 2000;67(3):253-64. Erratum in: Biotechnol Bioeng Nov. 20, 2001;75(4):494.

Scheurich et al., Quantification and characterization of high-affinity membrane receptors for tumor necrosis factor on human leukemic cell lines. Int J Cancer. Jul. 15, 1986;38(1):127-33.

(56) References Cited

OTHER PUBLICATIONS

Schlaeppi et al., Characterization of a new potent, in vivo neutralizing monoclonal antibody to human vascular endothelial growth factor. J Cancer Res Clin Oncol. 1999;125(6):336-42.
Shalaby et al., The involvement of human tumor necrosis factors-alpha and -beta in the mixed lymphocyte reaction. J Immunol. Jul. 15, 1988;141(2):499-503.
Sherman et al., Protection of calves against fatal enteric colibacillosis by orally administered *Escherichia coli* K99-specific monoclonal antibody. Infect Immun. Nov. 1983;42(2):653-8.
Shimamoto et al., Inhibition of Helicobacter pylori infection by orally administered yolk-derived anti-Helicobacter pylori antibody. Database Biosis Bioscience Information Service, Philadelphia, PA, US. May 2002.
Silacci et al., Design, construction, and characterization of a large synthetic human antibody phage display library. Proteomics. Jun. 2005;5(9):2340-50.
Skurkovich et al., Treatment of corneal transplant rejection in humans with anti-interferon-gamma antibodies. Am J Ophthalmol Jun. 2002;133(6):829-30.
Smith et al., Prolonged in vivo residence times of antibody fragments associated with albumin. Bioconjug Chem. Sep.-Oct. 2001;12(5):750-6.
Stadler et al., Biological activities of anti-IgE antibodies. Int Arch Allergy Immunol. 1993;102(2):121-6.
Stahl et al., The use of gene fusions to protein A and protein G in immunology and biotechnology. Pathol Biol (Paris). Jan. 1997;45(1):66-76.
Stancovski et al., Mechanistic aspects of the opposing effects of monoclonal antibodies to the ERBB2 receptor on tumor growth. Proc Natl Acad Sci U S A. Oct. 1, 1991;88(19):8691-5.
Sunada et al., Monoclonal antibody against epidermal growth factor receptor is internalized without stimulating receptor phosphorylation. Proc Natl Acad Sci U S A. Jun. 1986;83(11):3825-9.
Tanha et al., Optimal design features of camelized human single-domain antibody libraries. J Biol Chem. Jul. 6, 2001;276(27):24774-80. Epub May 2, 2001.
Tanha et al., Selection by phage display of llama conventional V(H) fragments with heavy chain antibody V(H)H properties. J Immunol Methods. May 1, 2002;263(1-2):97-109.
Teitelbaum et al., A mAb recognizing a surface antigen of *Mycobacterium tuberculosis* enhances host survival. Proc Natl Acad Sci U S A. Dec. 22, 1998;95(26):15688-93.
Terskikh et al., "Peptabody": a new type of high avidity binding protein. Proc Natl Acad Sci U S A. Mar. 4, 1997;94(5):1663-8.
Thiel et al., Penetration of engineered antibody fragments into the eye. Clin Exp Immunol. Apr. 2002;128(1):67-74.
Think et al., Improved tumor targeting of anti-epidermal growth factor receptor Nanobodies through albumin binding: taking advantage of modular Nanobody technology. Mol Cancer Ther. Aug. 2008;7(8):2288-97.
Valle et al., Infliximab. Expert Opin Pharmacother. Jun. 2001;2(6):1015-25.

Van Den Beucken et al., Building novel binding ligands to B7.1 and B7.2 based on human antibody single variable light chain domains. J Mol Biol. Jul. 13, 2001;310(3):591-601.
Van Der Linden et al., Induction of immune responses and molecular cloning of the heavy chain antibody repertoire of Lama glama. J Immunol Methods. Jun. 23, 2000;240(1-2):185-95.
Van Der Vaart et al., Reduction in morbidity of rotavirus induced diarrhoea in mice by yeast produced monovalent llama-derived antibody fragments. Vaccine. May 8, 2006;24(19):4130-7. Epub Mar. 7, 2006.
Vickers, A vaccine against Alzheimer's disease: developments to date. Drugs Aging. 2002;19(7):487-94.
Waldmann et al., The renal handling of low molecular weight proteins. II. Disorders of serum protein catabolism in patients with tubular proteinuria, the nephrotic syndrome, or uremia. J Clin Invest. Aug. 1972;51(8):2162-74.
Ward et al., Binding activities of a repertoire of single immunoglobulin variable domains secreted from *Escherichia coli*. Nature. Oct. 12, 1989;341(6242):544-6.
Weir et al., Formatting antibody fragments to mediate specific therapeutic functions. Biochem Soc Trans. Aug. 2002;30(4):512-6.
Wesolowski et al., Single domain antibodies: promising experimental and therapeutic tools in infection and immunity. Med Microbiol Immunol. Aug. 2009;198(3):157-74. Epub Jun. 16, 2009.
Wilkstrand et al., Monoclonal antibodies against EGFRvIII are tumor specific and react with breast and lung carcinomas and malignant gliomas. Cancer Res. Jul. 15, 1995;55(14):3140-8.
Winkler et al., Changing the antigen binding specificity by single point mutations of an anti-p24 (HIV-1) antibody. J Immunol. Oct. 15, 2000;165(8):4505-14.
Witte et al., Monoclonal antibodies targeting the VEGF receptor-2 (Flk1/KDR) as an antiangiogenic therapeutic strategy. Cancer Metastasis Rev. Jun. 1998;17(2):155-61.
Worledge et al., Oral administration of avian tumor necrosis factor antibodies effectively treats experimental colitis in rats. Dig Dis Sci. Dec. 2000;45(12):2298-305.
Zhu et al., Inhibition of tumor growth and metastasis by targeting tumor-associated angiogenesis with antagonists to the receptors of vascular endothelial growth factor. Invest New Drugs. 1999;17(3):195-212.
Davies et al., Single antibody domains as small recognition units: design and in vitro antigen selection of camelized, human VH domains with improved protein stability. Protein Eng. Jun. 1996;9(6):531-7.
Hamada et al., Localization of carcinoembryonic antigen in medullary thyroid carcinoma by immunofluorescent techniques. Br J Cancer. Nov. 1977;36(5):572-6.
Nielsen et al., Carcino-embryonic antigen (CEA) in gastric adenocarcinomas. Morphologic patterns and their relationship to a histogenetic classification. Acta Pathol Microbiol Immunol Scand A. Nov. 1982;90(6):393-6. Abstract only.
Riechmann, Rearrangement of the former VL interface in the solution structure of a camelised, single antibody VH domain. J Mol Biol. Jun. 28, 1996;259(5):957-69.
Tsaltas et al., Demonstration of monoclonal anti-carcinoembryonic antigen (CEA) antibody internalization by electron microscopy, western blotting and radioimmunoassay. Anticancer Res. Nov.-Dec. 1992;12(6B):2133-42. Abstract only.

```
            FR1                    CDR1             FR2
VHH#3G   QVQLQDSGGGLVQAGGSLRLSCAVSGR TFSAHS--VYTMG   WFRQAPGKEREFVA
VHH#3E   QVQLQESGGGLVQPGGSLRLSCAASGR TFSDHSGYTYTIG   WFRQAPGKEREFVA
VHH#1A   QVQLQESGGGLVQPGGSLRLSCATSGF DFS--VSWMY---   WVRQAPGKGLEWVS
VHH#2B   QVQLQESGGGLVQPGGSLRLSCATSGF TFS--DYWMY---   WVRQAPGKGLEWVS
VHH#12B  QVQLQESGGGLVQPGGSLRLSCAASGF EFE--NHWMY---   WVRQAPGKGLEWVS
VHH#7B   QVQLQESGGGLVQPGGSLRLSCAASGS IFRVNA-----MG   WYRQVPGNQREFVA
         ***** ****** ********* **   *             * ** **    * *

CDR2                        FR2
VHH#3G   RIYWSSANTYYADSVKG   RFTISRDNAKNTVDLLMNSLKPEDTAVYYCAA
VHH#3E   RIYWSSGNTYYADSVKG   RFAISRDIAKNTVDLTMNNLEPEDTAVYYCAA
VHH#1A   EINTNGLITKYVDSVKG   RFTISRDNAKNTLYLQMDSLIPEDTALYYCAR
VHH#2B   TVNTNGLITRYADSVKG   RFTISRDNAKYTLYLQMNSLKSEDTAVYYCTK
VHH#12B  TVNTNGLITRYADSVKG   RFTISRDNAKYTLYLQMNSLKSEDTAVYYCTK
VHH#7B   -IITSGDNLNYADAVKG   RFTISTDNVKKTVYLQMNVLKPEDTAVYYCNA
          *  * *** ** ** *   *  *   *   *  **** ***

CDR3         FR4       Hinge
VHH#3G   RDGIPTSRTVGSYNY  WGQGTQVTVSS EPKTPKPQP
VHH#3E   RDGIPTSRSVESYNY  WGQGTQVTVSS EPKTPKPQP
VHH#1A   ----------SPSGSF RGQGTQVTVSS EPKTPKPQP
VHH#2B   -VVPPYSDDSRTNAD  WGQGTQVTVSS EPKTPKPQP
VHH#12B  -VLPPYSDDSRTNAD  WGQGTQVTVSS EPKTPKPQP
VHH#7B   --ILQTSRWSIPSNY  WGQGTQVTVSS EPKTPKPQP
                         ********** *********
```

Figure 1

```
                       FR1                     CDR1      FR2
VHH#m3F    QVQLQDSGGGLVQAGGSLRLSCAASGG TFSSIIMA WFRQAPGKEREFVGA
VHH#m4B    QVQLQDSGGGLVQAGGSLRLSCGVSGL SFSGYTMG WFRQAPGKEREFAAA
VHH#m9A    EVQLVESGGGLVQAGGSLRLSCAASGG TLSSYITG WFRQAPGKEREFVGA
VHH#m9E    QVQLVESGGGLVQAGGSLRLSCAASEG TLSGYILG WFRQAPGKEREFVGA
           ***  ***************  *        *    ***********  *

CDR2                          FR2
VHH#m3F    VSWSGGTTVYADSVLG RFEISRDSARKSVYLQMNSLKPEDTAVYYCAA
VHH#m4B    IGWNSGTTEYRNSVKG RFTISRDNAKNTVYLQMNSLKPEDTAVYYCAA
VHH#m9A    VSWSSSTIVYADSVEG RFTISRDNHQNTVYLQMDSLKPEDTAVYYCAA
VHH#m9E    VSWSGGTIVYADSVKG RFEISRDNARNTVYLQMDSLKSEDTAVYYCAA
            *  *  *  ** * ** ****  ***** *** **********

CDR3            FR4      Hinge
VHH#m3F    RPYQKYNWA-SASYNV WGQGTQVTVSS EPKTPKPQP
VHH#m4B    SP--KYMTAYERSYDF WGQGTQVTVSS EPKTPKPQP
VHH#m9A    RPYQKYNWA-SASYNV WGQGTQVTVSS ---------
VHH#m9E    RPYQRFNWA-SASYNV WGRGTQVTVSS ---------
             *  *  **     ** ********
```

Figure 8

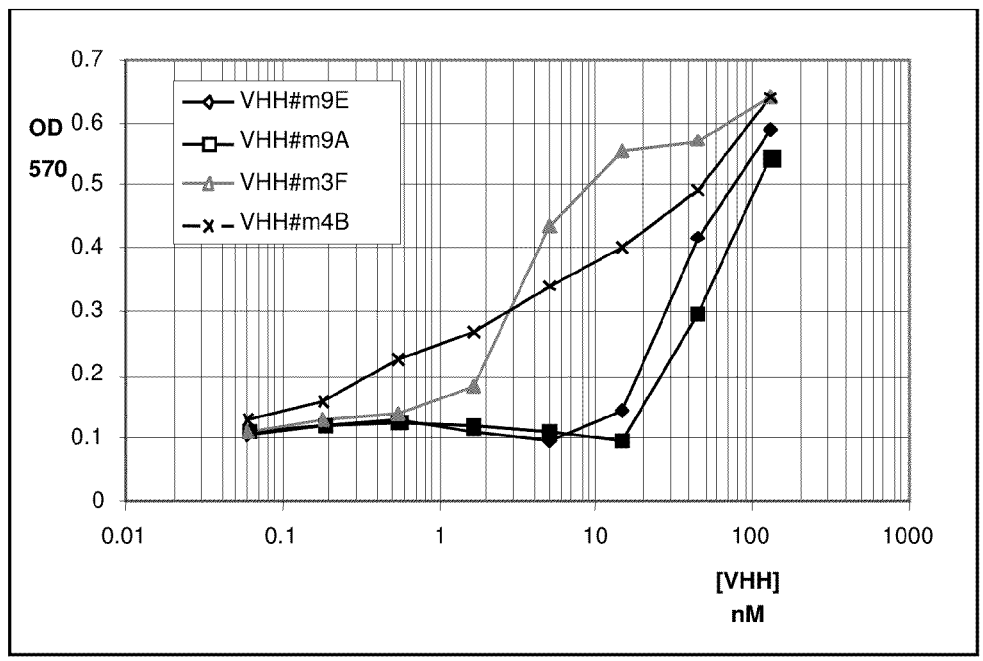

Figure 9

```
     HindIII
   1 aagcttgcat gcaaattcta tttcaaggag acagtcataa tgaaatacct attgcctacg gcagccgctg gattgttatt
                                                 M  K  Y  L  L  P  T  A  A  A  G  L  L  L
                                                 <                          pelB-leader SfiI  NcoI               NotI             PstI
  81 actcgcggcc cagccggcca tggggcctaa taggcggccg cacaggtgca gctgcaggag tcataatgag ggacccaggt
      L  A  A  Q  P  A  M  G  P  -  - A  A  A  Q  V  Q  L  Q  E  S  -  -  G  T  Q  V
           Leader            ><     VHH#1 >        <                             VHH#2

BstEII
 161 caccgtctcc tcagaacaaa aactcatctc agaagaggat ctgaatgggg ccgcacatca tcatcatcat cattaatgag
      T  V  S  S  E  Q  K  L  I  S  E  E  D  L  N  G  A  A  H  H  H  H  H  H  -  -
            ><       C-MYC                              >      <       His6             >

EcoRI
 241 aattcactgg ccg
```

Figure 10

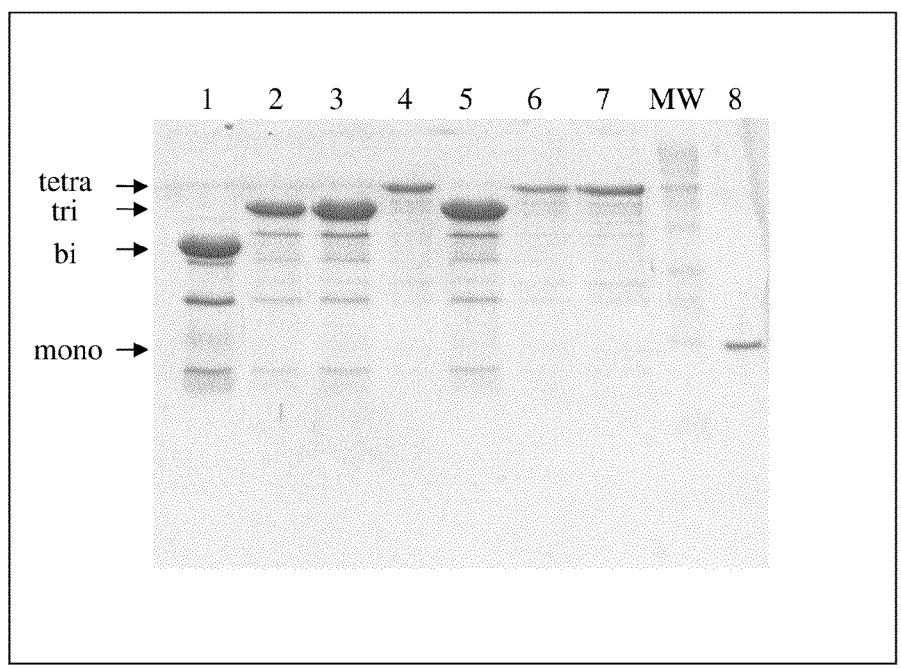

Figure 11

SEQUENCE LISTING

<160> NUMBER OF SEQ ID NOS: 132

<210> SEQ ID NO 1
<211> LENGTH: 115
<212> TYPE: PRT
<213> ORGANISM: Lama glama

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Asp Phe Ser Val Ser
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Ile Pro Glu Asp Thr Ala Leu Tyr Tyr Cys
            85                  90                  95

Ala Arg Ser Pro Ser Gly Ser Phe Arg Gly Gln Gly Thr Gln Val Thr
                100                 105                 110

Val Ser Ser
        115

<210> SEQ ID NO 2
<211> LENGTH: 121
<212> TYPE: PRT
<213> ORGANISM: Lama glama

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Arg Val Asn
            20                  25                  30

Ala Met Gly Trp Tyr Arg Gln Val Pro Gly Asn Gln Arg Glu Phe Val
        35                  40                  45

Ala Ile Ile Thr Ser Gly Asp Asn Leu Asn Tyr Ala Asp Ala Val Lys
    50                  55                  60

Gly Arg Phe Thr Ile Ser Thr Asp Asn Val Lys Lys Thr Val Tyr Leu
65                  70                  75                  80

Gln Met Asn Val Leu Lys Pro Glu Asp Thr Ala Val Tyr Tyr Cys Asn
            85                  90                  95

Ala Ile Leu Gln Thr Ser Arg Trp Ser Ile Pro Ser Asn Tyr Trp Gly
                100                 105                 110

Gln Gly Thr Gln Val Thr Val Ser Ser
        115                 120

<210> SEQ ID NO 3
<211> LENGTH: 123
<212> TYPE: PRT
<213> ORGANISM: Lama glama

<400> SEQUENCE: 3

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Thr Val Asn Thr Asn Gly Leu Ile Thr Arg Tyr Ala Asp Ser Val
    50                  55                  60

Lys Gly Arg Phe Thr Ile Ser Arg Asp Asn Ala Lys Tyr Thr Leu Tyr
65                  70                  75                  80

Leu Gln Met Asn Ser Leu Lys Ser Glu Asp Thr Ala Val Tyr Tyr Cys
            85                  90                  95

Thr Lys Val Val Pro Pro Tyr Ser Asp Asp Ser Arg Thr Asn Ala Asp
                100                 105                 110

Trp Gly Gln Gly Thr Gln Val Thr Val Ser Ser
        115                 120

<210> SEQ ID NO 4

```
<211> LENGTH: 129
<212> TYPE: PRT
<213> ORGANISM: Lama glama

<400> SEQUENCE: 4

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asp His
            20                  25                  30

Ser Gly Tyr Thr Tyr Thr Ile Gly Trp Phe Arg Gln Ala Pro Gly Lys
        35                  40                  45

Glu Arg Glu Phe Val Ala Arg Ile Tyr Trp Ser Ser Gly Asn Thr Tyr
50                  55                  60

Tyr Ala Asp Ser Val Lys Gly Arg Phe Ala Ile Ser Arg Asp Ile Ala
65                  70                  75                  80

Lys Asn Thr Val Asp Leu Thr Met Asn Asn Leu Glu Pro Glu Asp Thr
                85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser

<210> SEQ ID NO 5
<211> LENGTH: 127
<212> TYPE: PRT
<213> ORGANISM: Lama glama

<400> SEQUENCE: 5

Gln Val Gln Leu Gln Asp Ser Gly Gly Gly Leu Val Gln Ala Gly Gly
1               5                   10                  15

Ser Leu Arg Leu Ser Cys Ala Val Ser Gly Arg Thr Phe Ser Ala His
            20                  25                  30

Ser Val Tyr Thr Met Gly Trp Phe Arg Gln Ala Pro Gly Lys Glu Arg
        35                  40                  45

Glu Phe Val Ala Arg Ile Tyr Trp Ser Ser Ala Asn Thr Tyr Tyr Ala
50                  55                  60

Asp Ser Val Lys Gly Arg Phe Thr Ile Ser Arg Asp Asn Ala Lys Asn
65                  70                  75                  80

Thr Val Asp Leu Leu Met Asn Ser Leu Lys Pro Glu Asp Thr Ala Val
                85                  90                  95

Tyr Tyr Cys Ala Ala Arg Asp Gly Ile Pro Thr Ser Arg Thr Val Gly
            100                 105                 110

Ser Tyr Asn Tyr Trp Gly Gln Gly Thr Gln Val Thr Val Ser Ser
        115                 120                 125

<210> SEQ ID NO 6
<211> LENGTH: 124
<212> TYPE: PRT
<213> ORGANISM: Lama glama

<400> SEQUENCE: 6

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Arg Val Asn
            20                  25                  30

Ala Met Gly Trp Tyr Arg Gln Val Pro Gly Asn Gln Arg Glu Phe Val
```

```
                35                  40                  45
Ala Ile Ile Thr Ser Ser Asp Thr Asn Asp Thr Asn Tyr Ala Asp
            50                  55                  60
Ala Val Lys Gly Arg Phe Thr Ile Ser Thr Asp Asn Val Lys Thr
 65                  70                  75                  80
Val Tyr Leu Gln Met Asn Val Leu Lys Pro Glu Asp Thr Ala Val Tyr
                85                  90                  95
Tyr Cys Asn Ala Val Leu Gln Thr Ser Arg Trp Ser Ile Pro Ser Asn
            100                 105                 110
Tyr Trp Gly Gln Gly Thr Gln Val Thr Val Ser Ser
        115                 120
```

<210> SEQ ID NO 7
<211> LENGTH: 123
<212> TYPE: PRT
<213> ORGANISM: Lama glama

<400> SEQUENCE: 7

```
Gln Val Gln Leu Gln Asp Ser Gly Gly Gly Leu Val Gln Ala Gly Gly
 1               5                  10                  15
Ser Leu Arg Leu Ser Cys Thr Ser Gly Arg Thr Ile Ser Val Tyr
            20                  25                  30
Ala Met Gly Trp Phe Arg Gln Ala Pro Gly Lys Glu Arg Glu Phe Val
                35                  40                  45
Ala Ser Ile Ser Gly Ser Gly Ala Ile Thr Pro Tyr Ala Asp Ser Val
            50                  55                  60
Lys Gly Arg Phe Thr Ile Ser Arg Asp Asn Ala Lys Asn Thr Val Tyr
 65                  70                  75                  80
Leu Gln Met Asn Ser Leu Asn Pro Glu Asp Thr Ala Val Tyr Tyr Cys
                85                  90                  95
Ala Ala Ser Arg Tyr Ala Arg Tyr Arg Asp Val His Ala Tyr Asp Tyr
            100                 105                 110
Trp Gly Gln Gly Thr Gln Val Thr Val Ser Ser
        115                 120
```

<210> SEQ ID NO 8
<211> LENGTH: 124
<212> TYPE: PRT
<213> ORGANISM: Lama glama

<400> SEQUENCE: 8

```
Gln Val Gln Leu Gln Asp Ser Gly Gly Gly Leu Val Gln Ala Gly Gly
 1               5                  10                  15
Ser Leu Arg Leu Ser Cys Ala Ala Ser Thr Arg Thr Phe Ser Arg Tyr
            20                  25                  30
Val Val Gly Trp Phe Arg Gln Ala Pro Gly Lys Glu Arg Glu Phe Val
                35                  40                  45
Ala Thr Ile Ser Trp Asn Gly Glu His Thr Tyr Tyr Ala Asp Ser Val
            50                  55                  60
Lys Gly Arg Tyr Thr Ile Ser Arg Asp Asn Ala Lys Asn Thr Val Tyr
 65                  70                  75                  80
Leu Gln Met Gly Ser Leu Lys Pro Glu Asp Thr Ala Val Tyr Tyr Cys
                85                  90                  95
Ala Ala Arg Ser Phe Trp Gly Tyr Asn Val Glu Gln Arg Asp Phe Gly
            100                 105                 110
Ser Trp Gly Gln Gly Thr Pro Val Thr Val Ser Ser
```

<210> SEQ ID NO 9
<211> LENGTH: 120
<212> TYPE: PRT
<213> ORGANISM: Lama glama

<400> SEQUENCE: 9

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Arg Val Asn
            20                  25                  30

Ala Met Gly Trp Tyr Arg Gln Val Pro Gly Asn Gln Arg Glu Phe Val
        35                  40                  45

Ala Ile Ile Thr Asn Asp Thr Thr Asn Tyr Ala Asp Ala Val Lys Gly
    50                  55                  60

Arg Phe Thr Ile Ser Thr Asp Asn Val Lys Lys Thr Val Tyr Leu Gln
65                  70                  75                  80

Met Asn Val Leu Lys Pro Glu Asp Thr Ala Val Tyr Tyr Cys Asn Thr
                85                  90                  95

Val Leu Gln Thr Ser Arg Trp Asn Ile Pro Thr Asn Tyr Trp Gly Gln
            100                 105                 110

Gly Thr Gln Val Thr Val Ser Ser
        115                 120

<210> SEQ ID NO 10
<211> LENGTH: 120
<212> TYPE: PRT
<213> ORGANISM: Lama glama

<400> SEQUENCE: 10

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Arg Val Asn
            20                  25                  30

Ala Met Gly Trp Tyr Arg Gln Val Pro Gly Asn Gln Arg Glu Phe Val
        35                  40                  45

Ala Ile Ile Ser Gly Asp Thr Thr Asn Tyr Ala Asp Ala Val Lys Gly
    50                  55                  60

Arg Phe Thr Ile Ser Thr Asp Asn Val Lys Lys Thr Val Tyr Leu Gln
65                  70                  75                  80

Met Asn Val Leu Glu Ser Glu Asp Thr Ala Val Tyr Tyr Cys Asn Ala
                85                  90                  95

Val Leu Gln Thr Ser Arg Trp Ser Ile Pro Ser Asn Tyr Trp Gly Gln
            100                 105                 110

Gly Thr Gln Val Thr Val Ser Ser
        115                 120

<210> SEQ ID NO 11
<211> LENGTH: 116
<212> TYPE: PRT
<213> ORGANISM: Lama glama

<400> SEQUENCE: 11

Gln Val Gln Leu Gln Asp Ser Gly Gly Gly Leu Val Gln Pro Gly Gly
1               5                   10                  15

Ser Leu Arg Leu Ala Cys Val Ala Ser Gly Ser Ile Phe Ser Ile Asp
            20                  25                  30

```
Val Met Gly Trp Tyr Arg Gln Ala Pro Gly Gln Gln Arg Glu Leu Val
        35                  40                  45

Ala Thr Ile Thr Asn Ser Trp Thr Asn Tyr Ala Asp Ser Val Lys
 50                  55                  60

Gly Arg Phe Thr Ile Ser Arg Asp Asn Ala Lys Asn Val Val Tyr Leu
 65                  70                  75                  80

Gln Met Asn Ser Leu Lys Leu Glu Asp Thr Ala Val Tyr Tyr Cys Asn
                 85                  90                  95

Ala Arg Arg Trp Tyr Gln Pro Glu Ala Trp Gly Gln Gly Thr Gln Val
            100                 105                 110

Thr Val Ser Ser
            115
```

<210> SEQ ID NO 12
<211> LENGTH: 115
<212> TYPE: PRT
<213> ORGANISM: Lama glama

<400> SEQUENCE: 12

```
Gln Val Gln Leu Gln Asp Ser Gly Gly Gly Leu Val Gln Pro Gly Gly
 1               5                  10                  15

Ser Leu Arg Leu Ser Cys Ala Ala Ser Gly Phe Thr Phe Ser Thr His
                 20                  25                  30

Trp Met Tyr Trp Val Arg Gln Ala Pro Gly Lys Gly Leu Glu Trp Val
            35                  40                  45

Ser Thr Ile Asn Thr Asn Gly Leu Ile Thr Asp Tyr Ile His Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                 85                  90                  95

Ala Leu Asn Gln Ala Gly Leu Ser Arg Gly Gly Gly Thr Gln Val Thr
            100                 105                 110

Val Ser Ser
            115
```

<210> SEQ ID NO 13
<211> LENGTH: 126
<212> TYPE: PRT
<213> ORGANISM: Lama glama

<400> SEQUENCE: 13

```
Gln Val Gln Leu Gln Glu Ser Gly Gly Gly Leu Val Gln Ala Gly Gly
 1               5                  10                  15

Ser Leu Arg Leu Ser Cys Ala Ala Ser Arg Arg Thr Phe Ser Gly Tyr
                 20                  25                  30

Ala Met Gly Trp Phe Arg Gln Ala Pro Gly Lys Glu Arg Glu Phe Val
            35                  40                  45

Ala Val Val Ser Gly Thr Gly Thr Ile Ala Tyr Tyr Ala Asp Ser Val
 50                  55                  60

Lys Gly Arg Phe Thr Ile Ser Arg Asp Asn Ala Glu Asn Thr Val Tyr
 65                  70                  75                  80

Leu Gln Met Asn Ser Leu Lys Pro Glu Asp Thr Gly Leu Tyr Tyr Cys
                 85                  90                  95

Ala Val Gly Pro Ser Ser Ser Arg Trp Tyr Tyr Arg Gly Ala Ser Leu
            100                 105                 110
```

```
Val Asp Tyr Trp Gly Lys Gly Thr Leu Val Thr Val Ser Ser
            115                 120                 125
```

<210> SEQ ID NO 14
<211> LENGTH: 123
<212> TYPE: PRT
<213> ORGANISM: Lama glama

<400> SEQUENCE: 14

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Glu Phe Glu Asn His
            20                  25                  30

Trp Met Tyr Trp Val Arg Gln Ala Pro Gly Lys Gly Leu Glu Trp Val
        35                  40                  45

Ser Thr Val Asn Thr Asn Gly Leu Ile Thr Arg Tyr Ala Asp Ser Val
    50                  55                  60

Lys Gly Arg Phe Thr Ile Ser Arg Asp Asn Ala Lys Tyr Thr Leu Tyr
65                  70                  75                  80

Leu Gln Met Asn Ser Leu Lys Ser Glu Asp Thr Ala Val Tyr Tyr Cys
                85                  90                  95

Thr Lys Val Leu Pro Pro Tyr Ser Asp Asp Ser Arg Thr Asn Ala Asp
            100                 105                 110

Trp Gly Gln Gly Thr Gln Val Thr Val Ser Ser
            115                 120
```

<210> SEQ ID NO 15
<211> LENGTH: 124
<212> TYPE: PRT
<213> ORGANISM: Lama glama

<400> SEQUENCE: 15

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Ser Tyr
            20                  25                  30

Ile Thr Gly Trp Phe Arg Gln Ala Pro Gly Lys Glu Arg Glu Phe Val
        35                  40                  45

Gly Ala Val Ser Trp Ser Ser Thr Ile Val Tyr Ala Asp Ser Val
    50                  55                  60

Glu Gly Arg Phe Thr Ile Ser Arg Asp Asn His Gln Asn Thr Val Tyr
65                  70                  75                  80

Leu Gln Met Asp Ser Leu Lys Pro Glu Asp Thr Ala Val Tyr Tyr Cys
                85                  90                  95

Ala Ala Arg Pro Tyr Gln Lys Tyr Asn Trp Ala Ser Ala Ser Tyr Asn
            100                 105                 110

Val Trp Gly Gln Gly Thr Gln Val Thr Val Ser Ser
            115                 120
```

<210> SEQ ID NO 16
<211> LENGTH: 124
<212> TYPE: PRT
<213> ORGANISM: Lama glama

<400> SEQUENCE: 16

```
Gln Val Gln Leu Gln Asp Ser Gly Gly Gly Leu Val Gln Ala Gly Gly
1               5                   10                  15
```

```
Ser Leu Arg Leu Ser Cys Ala Ala Ser Gly Thr Phe Ser Ser Ile
            20                  25                  30

Ile Met Ala Trp Phe Arg Gln Ala Pro Gly Lys Glu Arg Glu Phe Val
        35                  40                  45

Gly Ala Val Ser Trp Ser Gly Gly Thr Thr Val Tyr Ala Asp Ser Val
    50                  55                  60

Leu Gly Arg Phe Glu Ile Ser Arg Asp Ser Ala Arg Lys Ser Val Tyr
65                  70                  75                  80

Leu Gln Met Asn Ser Leu Lys Pro Glu Asp Thr Ala Val Tyr Tyr Cys
            85                  90                  95

Ala Ala Arg Pro Tyr Gln Lys Tyr Asn Trp Ala Ser Ala Ser Tyr Asn
            100                 105                 110

Val Trp Gly Gln Gly Thr Gln Val Thr Val Ser Ser
        115                 120

<210> SEQ ID NO 17
<211> LENGTH: 123
<212> TYPE: PRT
<213> ORGANISM: Lama glama

<400> SEQUENCE: 17

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Glu Phe Glu Asn His
            20                  25                  30

Trp Met Tyr Trp Val Arg Gln Ala Pro Gly Lys Gly Leu Glu Trp Val
        35                  40                  45

Ser Thr Val Asn Thr Asn Gly Leu Ile Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Lys Val Leu Pro Pro Tyr Ser Asp Asp Ser Arg Thr Asn Ala Asp
            100                 105                 110

Trp Gly Gln Gly Thr Gln Val Thr Val Ser Ser
        115                 120

<210> SEQ ID NO 18
<211> LENGTH: 123
<212> TYPE: PRT
<213> ORGANISM: Lama glama

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Glu Phe Glu Asn His
            20                  25                  30

Trp Met Tyr Trp Val Arg Gln Ala Pro Gly Lys Gly Leu Glu Trp Val
        35                  40                  45

Ser Thr Val Asn Thr Asn Gly Leu Ile Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95
```

```
Thr Lys Val Leu Pro Pro Tyr Ser Asp Asp Ser Arg Thr Asn Ala Asp
            100                 105                 110

Trp Gly Gln Gly Thr Gln Val Thr Val Ser Ser
        115                 120
```

<210> SEQ ID NO 19
<211> LENGTH: 123
<212> TYPE: PRT
<213> ORGANISM: Lama glama

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Glu Phe Glu Asn His
            20                  25                  30

Trp Met Tyr Trp Val Arg Gln Ala Pro Gly Lys Gly Leu Glu Trp Val
        35                  40                  45

Ser Thr Val Asn Thr Asn Gly Leu Ile Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Pro Pro Tyr Ser Asp Asp Ser Arg Thr Asn Ala Asp
            100                 105                 110

Trp Gly Gln Gly Thr Gln Val Thr Val Ser Ser
        115                 120
```

<210> SEQ ID NO 20
<211> LENGTH: 123
<212> TYPE: PRT
<213> ORGANISM: Lama glama

<400> SEQUENCE: 20

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Glu Phe Glu Asn His
            20                  25                  30

Trp Met Tyr Trp Val Arg Gln Ala Pro Gly Lys Gly Leu Glu Trp Val
        35                  40                  45

Ser Thr Val Asn Thr Asn Gly Leu Ile Thr Arg Tyr Ala Asp Ser Val
    50                  55                  60

Lys Gly Arg Phe Thr Ile Ser Arg Asp Asn Ala Lys Tyr Thr Leu Tyr
65                  70                  75                  80

Leu Gln Met Asn Ser Leu Lys Ser Glu Asp Thr Ala Val Tyr Tyr Cys
                85                  90                  95

Thr Lys Val Leu Pro Pro Tyr Ser Asp Asp Ser Arg Thr Asn Ala Asp
            100                 105                 110

Trp Gly Gln Gly Thr Gln Val Thr Val Ser Ser
        115                 120
```

<210> SEQ ID NO 21
<211> LENGTH: 129
<212> TYPE: PRT
<213> ORGANISM: Lama glama

<400> SEQUENCE: 21

```
Gln Val Gln Leu Gln Glu Ser Gly Gly Gly Leu Val Gln Pro Gly Gly
```

```
  1               5                  10                 15
Ser Leu Arg Leu Ser Cys Ala Ala Ser Gly Arg Thr Phe Ser Asp His
                20                  25                 30

Ser Gly Tyr Thr Tyr Thr Ile Gly Trp Val Arg Gln Ala Pro Gly Lys
                35                  40                 45

Glu Arg Glu Phe Val Ala Arg Ile Tyr Trp Ser Ser Gly Asn Thr Tyr
        50                  55                 60

Tyr Ala Asp Ser Val Lys Gly Arg Phe Ala Ile Ser Arg Asp Ile Ala
 65                 70                  75                 80

Lys Asn Thr Val Asp Leu Thr Met Asn Asn Leu Glu Pro Glu Asp Thr
                85                  90                 95

Ala Val Tyr Tyr Cys Ala Ala Arg Asp Gly Ile Pro Thr Ser Arg Ser
               100                 105                110

Val Glu Ser Tyr Asn Tyr Trp Gly Gln Gly Thr Gln Val Thr Val Ser
               115                 120                125

Ser
```

<210> SEQ ID NO 22
<211> LENGTH: 129
<212> TYPE: PRT
<213> ORGANISM: Lama glama

<400> SEQUENCE: 22

```
Gln Val Gln Leu Gln Glu Ser Gly Gly Gly Leu Val Gln Pro Gly Gly
 1               5                  10                 15

Ser Leu Arg Leu Ser Cys Ala Ala Ser Gly Arg Thr Phe Ser Asp His
                20                  25                 30

Ser Gly Tyr Thr Tyr Thr Ile Gly Trp Phe Arg Gln Ala Pro Gly Lys
                35                  40                 45

Gly Arg Glu Phe Val Ala Arg Ile Tyr Trp Ser Ser Gly Asn Thr Tyr
        50                  55                 60

Tyr Ala Asp Ser Val Lys Gly Arg Phe Ala Ile Ser Arg Asp Ile Ala
 65                 70                  75                 80

Lys Asn Thr Val Asp Leu Thr Met Asn Asn Leu Glu Pro Glu Asp Thr
                85                  90                 95

Ala Val Tyr Tyr Cys Ala Ala Arg Asp Gly Ile Pro Thr Ser Arg Ser
               100                 105                110

Val Glu Ser Tyr Asn Tyr Trp Gly Gln Gly Thr Gln Val Thr Val Ser
               115                 120                125

Ser
```

<210> SEQ ID NO 23
<211> LENGTH: 129
<212> TYPE: PRT
<213> ORGANISM: Lama glama

<400> SEQUENCE: 23

```
Gln Val Gln Leu Gln Glu Ser Gly Gly Gly Leu Val Gln Pro Gly Gly
 1               5                  10                 15

Ser Leu Arg Leu Ser Cys Ala Ala Ser Gly Arg Thr Phe Ser Asp His
                20                  25                 30

Ser Gly Tyr Thr Tyr Thr Ile Gly Trp Phe Arg Gln Ala Pro Gly Lys
                35                  40                 45

Glu Leu Glu Phe Val Ala Arg Ile Tyr Trp Ser Ser Gly Asn Thr Tyr
        50                  55                 60
```

```
Tyr Ala Asp Ser Val Lys Gly Arg Phe Ala Ile Ser Arg Asp Ile Ala
 65                  70                  75                  80

Lys Asn Thr Val Asp Leu Thr Met Asn Asn Leu Glu Pro Glu Asp Thr
                 85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser

<210> SEQ ID NO 24
<211> LENGTH: 129
<212> TYPE: PRT
<213> ORGANISM: Lama glama

<400> SEQUENCE: 24

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Arg Thr Phe Ser Asp His
            20                  25                  30

Ser Gly Tyr Thr Tyr Thr Ile Gly Trp Phe Arg Gln Ala Pro Gly Lys
        35                  40                  45

Glu Arg Glu Trp Val Ala Arg Ile Tyr Trp Ser Ser Gly Asn Thr Tyr
 50                  55                  60

Tyr Ala Asp Ser Val Lys Gly Arg Phe Ala Ile Ser Arg Asp Ile Ala
 65                  70                  75                  80

Lys Asn Thr Val Asp Leu Thr Met Asn Asn Leu Glu Pro Glu Asp Thr
                 85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser

<210> SEQ ID NO 25
<211> LENGTH: 129
<212> TYPE: PRT
<213> ORGANISM: Lama glama

<400> SEQUENCE: 25

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Arg Thr Phe Ser Asp His
            20                  25                  30

Ser Gly Tyr Thr Tyr Thr Ile Gly Trp Phe Arg Gln Ala Pro Gly Lys
        35                  40                  45

Glu Arg Glu Phe Val Ala Arg Ile Tyr Trp Ser Ser Gly Asn Thr Tyr
 50                  55                  60

Tyr Ala Asp Ser Val Lys Gly Arg Phe Ala Ile Ser Arg Asp Ile Ala
 65                  70                  75                  80

Lys Asn Thr Val Asp Leu Thr Met Asn Asn Leu Glu Pro Glu Asp Thr
                 85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125
```

Ser

<210> SEQ ID NO 26
<211> LENGTH: 115
<212> TYPE: PRT
<213> ORGANISM: Lama glama

<400> SEQUENCE: 26

```
Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110

Val Ser Ser
        115
```

<210> SEQ ID NO 27
<211> LENGTH: 115
<212> TYPE: PRT
<213> ORGANISM: Lama glama

<400> SEQUENCE: 27

```
Gln Val Gln Leu Gln Glu Ser Gly Gly Gly Leu Val Gln Pro Gly Asn
1               5                   10                  15

Ser Leu Arg Leu Ser Cys Ala Ala Ser Gly Phe Thr Phe Arg Asn Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asn Thr Ile Tyr Ala Asp Ser Val
    50                  55                  60

Lys Asp Arg Phe Thr Ile Ser Arg Asp Asn Ala Lys Ser Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115
```

<210> SEQ ID NO 28
<211> LENGTH: 114
<212> TYPE: PRT
<213> ORGANISM: Lama glama

<400> SEQUENCE: 28

```
Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Ser Ser Phe
```

```
                    20                  25                  30

Gly Met Ser Trp Val Arg Gln Ala Pro Gly Lys Gly Leu Glu Trp Val
            35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Ser Gln Gly Thr Gln Val Thr Val
            100                 105                 110

Ser Ser

<210> SEQ ID NO 29
<211> LENGTH: 114
<212> TYPE: PRT
<213> ORGANISM: Lama glama

<400> SEQUENCE: 29

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Gly Leu Glu Trp Val
            35                  40                  45

Ser Ala Ile Ser Ala Asp Gly Ser Asp Lys Arg Tyr Ala Asp Ser Val
    50                  55                  60

Lys Gly Arg Phe Thr Ile Ser Arg Asp Asn Gly Lys Lys Met Leu Thr
65                  70                  75                  80

Leu Asp Met Asn Ser Leu Lys Pro Glu Asp Thr Ala Val Tyr Tyr Cys
                85                  90                  95

Val Ile Gly Arg Gly Ser Pro Ala Ser Gln Gly Thr Gln Val Thr Val
            100                 105                 110

Ser Ser

<210> SEQ ID NO 30
<211> LENGTH: 256
<212> TYPE: PRT
<213> ORGANISM: Lama glama

<400> SEQUENCE: 30

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
            35                  40                  45

Ser Gly Ile Ser Ser Leu Gly Asp Ser Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110
```

Val Ser Ser Glu Pro Lys Thr Pro Lys Pro Gln Pro Ala Ala Ala Gln
            115                 120                 125

Val Gln Leu Gln Glu Ser Gly Gly Gly Leu Val Gln Pro Gly Gly Ser
        130                 135                 140

Leu Arg Leu Ser Cys Ala Ala Ser Gly Arg Thr Phe Ser Asp His Ser
145                 150                 155                 160

Gly Tyr Thr Tyr Thr Ile Gly Trp Phe Arg Gln Ala Pro Gly Lys Glu
                165                 170                 175

Arg Glu Phe Val Ala Arg Ile Tyr Trp Ser Ser Gly Asn Thr Tyr Tyr
            180                 185                 190

Ala Asp Ser Val Lys Gly Arg Phe Ala Ile Ser Arg Asp Ile Ala Lys
        195                 200                 205

Asn Thr Val Asp Leu Thr Met Asn Asn Leu Glu Pro Glu Asp Thr Ala
    210                 215                 220

Val Tyr Tyr Cys Ala Ala Arg Asp Gly Ile Pro Thr Ser Arg Ser Val
225                 230                 235                 240

Glu Ser Tyr Asn Tyr Trp Gly Gln Gly Thr Gln Val Thr Val Ser Ser
                245                 250                 255

<210> SEQ ID NO 31
<211> LENGTH: 256
<212> TYPE: PRT
<213> ORGANISM: Lama glama

<400> SEQUENCE: 31

Gln Val Gln Leu Gln Glu Ser Gly Gly Gly Leu Val Gln Pro Gly Asn
1               5                   10                  15

Ser Leu Arg Leu Ser Cys Ala Ala Ser Gly Phe Thr Phe Arg Asn Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asn Thr Ile Tyr Ala Asp Ser Val
    50                  55                  60

Lys Asp Arg Phe Thr Ile Ser Arg Asp Asn Ala Lys Ser Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser Glu Pro Lys Thr Pro Lys Pro Gln Pro Ala Ala Ala Gln
        115                 120                 125

Val Gln Leu Gln Glu Ser Gly Gly Gly Leu Val Gln Pro Gly Gly Ser
    130                 135                 140

Leu Arg Leu Ser Cys Ala Ala Ser Gly Arg Thr Phe Ser Asp His Ser
145                 150                 155                 160

Gly Tyr Thr Tyr Thr Ile Gly Trp Phe Arg Gln Ala Pro Gly Lys Glu
                165                 170                 175

Arg Glu Phe Val Ala Arg Ile Tyr Trp Ser Ser Gly Asn Thr Tyr Tyr
            180                 185                 190

Ala Asp Ser Val Lys Gly Arg Phe Ala Ile Ser Arg Asp Ile Ala Lys
        195                 200                 205

Asn Thr Val Asp Leu Thr Met Asn Asn Leu Glu Pro Glu Asp Thr Ala
    210                 215                 220

Val Tyr Tyr Cys Ala Ala Arg Asp Gly Ile Pro Thr Ser Arg Ser Val
225                 230                 235                 240

```
Glu Ser Tyr Asn Tyr Trp Gly Gln Gly Thr Gln Val Thr Val Ser Ser
                245                 250                 255
```

<210> SEQ ID NO 32
<211> LENGTH: 255
<212> TYPE: PRT
<213> ORGANISM: Lama glama

<400> SEQUENCE: 32

```
Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Gln Gly Thr Gln Val Thr Val
                100                 105                 110

Ser Ser Glu Pro Lys Thr Pro Lys Pro Gln Pro Ala Ala Ala Gln Val
            115                 120                 125

Gln Leu Gln Glu Ser Gly Gly Gly Leu Val Gln Pro Gly Gly Ser Leu
130                 135                 140

Arg Leu Ser Cys Ala Ala Ser Gly Arg Thr Phe Ser Asp His Ser Gly
145                 150                 155                 160

Tyr Thr Tyr Thr Ile Gly Trp Phe Arg Gln Ala Pro Gly Lys Glu Arg
                165                 170                 175

Glu Phe Val Ala Arg Ile Tyr Trp Ser Ser Gly Asn Thr Tyr Tyr Ala
            180                 185                 190

Asp Ser Val Lys Gly Arg Phe Ala Ile Ser Arg Asp Ile Ala Lys Asn
        195                 200                 205

Thr Val Asp Leu Thr Met Asn Asn Leu Glu Pro Glu Asp Thr Ala Val
    210                 215                 220

Tyr Tyr Cys Ala Ala Arg Asp Gly Ile Pro Thr Ser Arg Ser Val Glu
225                 230                 235                 240

Ser Tyr Asn Tyr Trp Gly Gln Gly Thr Gln Val Thr Val Ser Ser
                245                 250                 255
```

<210> SEQ ID NO 33
<211> LENGTH: 255
<212> TYPE: PRT
<213> ORGANISM: Lama glama

<400> SEQUENCE: 33

```
Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ala Ile Ser Ala Asp Gly Ser Asp Lys Arg Tyr Ala Asp Ser Val
    50                  55                  60
```

```
Lys Gly Arg Phe Thr Ile Ser Arg Asp Asn Gly Lys Met Leu Thr
 65                  70                  75                  80

Leu Asp Met Asn Ser Leu Lys Pro Glu Asp Thr Ala Val Tyr Tyr Cys
                 85                  90                  95

Val Ile Gly Arg Gly Ser Pro Ala Ser Gln Gly Thr Gln Val Thr Val
            100                 105                 110

Ser Ser Glu Pro Lys Thr Pro Lys Pro Gln Pro Ala Ala Ala Gln Val
        115                 120                 125

Gln Leu Gln Glu Ser Gly Gly Gly Leu Val Gln Pro Gly Gly Ser Leu
    130                 135                 140

Arg Leu Ser Cys Ala Ala Ser Gly Arg Thr Phe Ser Asp His Ser Gly
145                 150                 155                 160

Tyr Thr Tyr Thr Ile Gly Trp Phe Arg Gln Ala Pro Gly Lys Glu Arg
                165                 170                 175

Glu Phe Val Ala Arg Ile Tyr Trp Ser Ser Gly Asn Thr Tyr Tyr Ala
            180                 185                 190

Asp Ser Val Lys Gly Arg Phe Ala Ile Ser Arg Asp Ile Ala Lys Asn
        195                 200                 205

Thr Val Asp Leu Thr Met Asn Asn Leu Glu Pro Glu Asp Thr Ala Val
    210                 215                 220

Tyr Tyr Cys Ala Ala Arg Asp Gly Ile Pro Thr Ser Arg Ser Val Glu
225                 230                 235                 240

Ser Tyr Asn Tyr Trp Gly Gln Gly Thr Gln Val Thr Val Ser Ser
                245                 250                 255

<210> SEQ ID NO 34
<211> LENGTH: 383
<212> TYPE: PRT
<213> ORGANISM: Lama glama

<400> SEQUENCE: 34

Gln Val Gln Leu Gln Glu Ser Gly Gly Gly Leu Val Gln Pro Gly Gly
  1               5                  10                  15

Ser Leu Arg Leu Ser Cys Glu Ala Ser Gly Phe Thr Phe Ser Arg Phe
             20                  25                  30

Gly Met Thr Trp Val Arg Gln Ala Pro Gly Lys Gly Val Glu Trp Val
         35                  40                  45

Ser Gly Ile Ser Ser Leu Gly Asp Ser Thr Leu Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Thr Ile Gly Gly Ser Leu Asn Pro Gly Gly Gln Gly Thr Gln Val Thr
            100                 105                 110

Val Ser Ser Glu Pro Lys Thr Pro Lys Pro Gln Pro Ala Ala Ala Gln
        115                 120                 125

Val Gln Leu Gln Glu Ser Gly Gly Gly Leu Val Gln Pro Gly Gly Ser
    130                 135                 140

Leu Arg Leu Ser Cys Glu Ala Ser Gly Phe Thr Phe Ser Arg Phe Gly
145                 150                 155                 160

Met Thr Trp Val Arg Gln Ala Pro Gly Lys Gly Val Glu Trp Val Ser
                165                 170                 175

Gly Ile Ser Ser Leu Gly Asp Ser Thr Leu Tyr Ala Asp Ser Val Lys
```

```
            180                 185                 190
Gly Arg Phe Thr Ile Ser Arg Asp Asn Ala Lys Asn Thr Leu Tyr Leu
            195                 200                 205

Gln Met Asn Ser Leu Lys Pro Glu Asp Thr Ala Val Tyr Tyr Cys Thr
            210                 215                 220

Ile Gly Gly Ser Leu Asn Pro Gly Gly Gln Gly Thr Gln Val Thr Val
225                 230                 235                 240

Ser Ser Glu Pro Lys Thr Pro Lys Pro Gln Pro Ala Ala Ala Gln Val
            245                 250                 255

Gln Leu Gln Glu Ser Gly Gly Gly Leu Val Gln Pro Gly Gly Ser Leu
            260                 265                 270

Arg Leu Ser Cys Ala Ala Ser Gly Arg Thr Phe Ser Asp His Ser Gly
            275                 280                 285

Tyr Thr Tyr Thr Ile Gly Trp Phe Arg Gln Ala Pro Gly Lys Glu Arg
            290                 295                 300

Glu Phe Val Ala Arg Ile Tyr Trp Ser Ser Gly Asn Thr Tyr Tyr Ala
305                 310                 315                 320

Asp Ser Val Lys Gly Arg Phe Ala Ile Ser Arg Asp Ile Ala Lys Asn
            325                 330                 335

Thr Val Asp Leu Thr Met Asn Asn Leu Glu Pro Glu Asp Thr Ala Val
            340                 345                 350

Tyr Tyr Cys Ala Ala Arg Asp Gly Ile Pro Thr Ser Arg Ser Val Glu
            355                 360                 365

Ser Tyr Asn Tyr Trp Gly Gln Gly Thr Gln Val Thr Val Ser Ser
            370                 375                 380

<210> SEQ ID NO 35
<211> LENGTH: 241
<212> TYPE: PRT
<213> ORGANISM: Lama glama

<400> SEQUENCE: 35

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ala Ile Ser Ser Asp Ser Gly Thr Lys Asn Tyr Ala Asp Ser Val
            50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
            85                  90                  95

Val Ile Gly Arg Gly Ser Pro Ser Ser Gln Gly Thr Gln Val Thr Val
            100                 105                 110

Ser Ser Glu Pro Lys Thr Pro Lys Pro Gln Pro Ala Ala Ala Gln Val
            115                 120                 125

Gln Leu Gln Glu Ser Gly Gly Gly Leu Val Gln Pro Gly Gly Ser Leu
            130                 135                 140

Arg Leu Ser Cys Ala Thr Ser Gly Phe Asp Phe Ser Val Ser Trp Met
145                 150                 155                 160

Tyr Trp Val Arg Gln Ala Pro Gly Lys Gly Leu Glu Trp Val Ser Glu
            165                 170                 175
```

Ile Asn Thr Asn Gly Leu Ile Thr Lys Tyr Val Asp Ser Val Lys Gly
            180                 185                 190

Arg Phe Thr Ile Ser Arg Asp Asn Ala Lys Asn Thr Leu Tyr Leu Gln
        195                 200                 205

Met Asp Ser Leu Ile Pro Glu Asp Thr Ala Leu Tyr Tyr Cys Ala Arg
    210                 215                 220

Ser Pro Ser Gly Ser Phe Arg Gly Gln Gly Thr Gln Val Thr Val Ser
225                 230                 235                 240

Ser

<210> SEQ ID NO 36
<211> LENGTH: 247
<212> TYPE: PRT
<213> ORGANISM: Lama glama

<400> SEQUENCE: 36

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Ser Gln Gly Thr Gln Val Thr Val
            100                 105                 110

Ser Ser Glu Pro Lys Thr Pro Lys Pro Gln Pro Ala Ala Ala Gln Val
        115                 120                 125

Gln Leu Gln Glu Ser Gly Gly Gly Leu Val Gln Pro Gly Gly Ser Leu
    130                 135                 140

Arg Leu Ser Cys Ala Ala Ser Gly Ser Ile Phe Arg Val Asn Ala Met
145                 150                 155                 160

Gly Trp Tyr Arg Gln Val Pro Gly Asn Gln Arg Glu Phe Val Ala Ile
                165                 170                 175

Ile Thr Ser Gly Asp Asn Leu Asn Tyr Ala Asp Ala Val Lys Gly Arg
            180                 185                 190

Phe Thr Ile Ser Thr Asp Asn Val Lys Lys Thr Val Tyr Leu Gln Met
        195                 200                 205

Asn Val Leu Lys Pro Glu Asp Thr Ala Val Tyr Tyr Cys Asn Ala Ile
    210                 215                 220

Leu Gln Thr Ser Arg Trp Ser Ile Pro Ser Asn Tyr Trp Gly Gln Gly
225                 230                 235                 240

Thr Gln Val Thr Val Ser Ser
                245

<210> SEQ ID NO 37
<211> LENGTH: 249
<212> TYPE: PRT
<213> ORGANISM: Lama glama

<400> SEQUENCE: 37

Gln Val Gln Leu Gln Glu Ser Gly Gly Gly Leu Val Gln Pro Gly Gly

```
   1               5                   10                  15
Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Gln Gly Thr Gln Val Thr Val
            100                 105                 110

Ser Ser Glu Pro Lys Thr Pro Lys Pro Gln Pro Ala Ala Ala Gln Val
        115                 120                 125

Gln Leu Gln Glu Ser Gly Gly Gly Leu Val Gln Pro Gly Gly Ser Leu
    130                 135                 140

Arg Leu Ser Cys Ala Thr Ser Gly Phe Thr Phe Ser Asp Tyr Trp Met
145                 150                 155                 160

Tyr Trp Val Arg Gln Ala Pro Gly Lys Gly Leu Glu Trp Val Ser Thr
                165                 170                 175

Val Asn Thr Asn Gly Leu Ile Thr Arg Tyr Ala Asp Ser Val Lys Gly
            180                 185                 190

Arg Phe Thr Ile Ser Arg Asp Asn Ala Lys Tyr Thr Leu Tyr Leu Gln
        195                 200                 205

Met Asn Ser Leu Lys Ser Glu Asp Thr Ala Val Tyr Tyr Cys Thr Lys
    210                 215                 220

Val Val Pro Pro Tyr Ser Asp Asp Ser Arg Thr Asn Ala Asp Trp Gly
225                 230                 235                 240

Gln Gly Thr Gln Val Thr Val Ser Ser
                245

<210> SEQ ID NO 38
<211> LENGTH: 255
<212> TYPE: PRT
<213> ORGANISM: Lama glama

<400> SEQUENCE: 38

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Gln Gly Thr Gln Val Thr Val
            100                 105                 110

Ser Ser Glu Pro Lys Thr Pro Lys Pro Gln Pro Ala Ala Ala Gln Val
        115                 120                 125
```

```
Gln Leu Gln Glu Ser Gly Gly Gly Leu Val Gln Pro Gly Gly Ser Leu
    130                 135                 140
Arg Leu Ser Cys Ala Ala Ser Gly Arg Thr Phe Ser Asp His Ser Gly
145                 150                 155                 160
Tyr Thr Tyr Thr Ile Gly Trp Phe Arg Gln Ala Pro Gly Lys Glu Arg
                165                 170                 175
Glu Phe Val Ala Arg Ile Tyr Trp Ser Ser Gly Asn Thr Tyr Tyr Ala
                180                 185                 190
Asp Ser Val Lys Gly Arg Phe Ala Ile Ser Arg Asp Ile Ala Lys Asn
                195                 200                 205
Thr Val Asp Leu Thr Met Asn Asn Leu Glu Pro Glu Asp Thr Ala Val
    210                 215                 220
Tyr Tyr Cys Ala Ala Arg Asp Gly Ile Pro Thr Ser Arg Ser Val Glu
225                 230                 235                 240
Ser Tyr Asn Tyr Trp Gly Gln Gly Thr Gln Val Thr Val Ser Ser
                245                 250                 255

<210> SEQ ID NO 39
<211> LENGTH: 253
<212> TYPE: PRT
<213> ORGANISM: Lama glama

<400> SEQUENCE: 39

Gln Val Gln Leu Gln Glu Ser Gly Gly Gly Leu Val Gln Pro Gly Gly
1               5                   10                  15
Ser Leu Arg Leu Thr Cys Thr Ala Ser Gly Phe Thr Phe Ser Ser Phe
                20                  25                  30
Gly Met Ser Trp Val Arg Gln Ala Pro Gly Lys Gly Leu Glu Trp Val
            35                  40                  45
Ser Ala Ile Ser Ser Asp Ser Gly Thr Lys Asn Tyr Ala Asp Ser Val
    50                  55                  60
Lys Gly Arg Phe Thr Ile Ser Arg Asp Asn Ala Lys Lys Met Leu Phe
65                  70                  75                  80
Leu Gln Met Asn Ser Leu Arg Pro Glu Asp Thr Ala Val Tyr Tyr Cys
                85                  90                  95
Val Ile Gly Arg Gly Ser Pro Ser Ser Gln Gly Thr Gln Val Thr Val
                100                 105                 110
Ser Ser Glu Pro Lys Thr Pro Lys Pro Gln Pro Ala Ala Ala Gln Val
            115                 120                 125
Gln Leu Gln Asp Ser Gly Gly Gly Leu Val Gln Ala Gly Gly Ser Leu
    130                 135                 140
Arg Leu Ser Cys Ala Val Ser Gly Arg Thr Phe Ser Ala His Ser Val
145                 150                 155                 160
Tyr Thr Met Gly Trp Phe Arg Gln Ala Pro Gly Lys Glu Arg Glu Phe
                165                 170                 175
Val Ala Arg Ile Tyr Trp Ser Ser Ala Asn Thr Tyr Tyr Ala Asp Ser
                180                 185                 190
Val Lys Gly Arg Phe Thr Ile Ser Arg Asp Asn Ala Lys Asn Thr Val
            195                 200                 205
Asp Leu Leu Met Asn Ser Leu Lys Pro Glu Asp Thr Ala Val Tyr Tyr
    210                 215                 220
Cys Ala Ala Arg Asp Gly Ile Pro Thr Ser Arg Thr Val Gly Ser Tyr
225                 230                 235                 240
Asn Tyr Trp Gly Gln Gly Thr Gln Val Thr Val Ser Ser
                245                 250
```

<210> SEQ ID NO 40
<211> LENGTH: 250
<212> TYPE: PRT
<213> ORGANISM: Lama glama

<400> SEQUENCE: 40

```
Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110

Val Ser Ser Glu Pro Lys Thr Pro Lys Pro Gln Pro Ala Ala Ala Gln
        115                 120                 125

Val Gln Leu Gln Glu Ser Gly Gly Gly Leu Val Gln Pro Gly Gly Ser
    130                 135                 140

Leu Arg Leu Ser Cys Ala Ala Ser Gly Phe Glu Phe Glu Asn His Trp
145                 150                 155                 160

Met Tyr Trp Val Arg Gln Ala Pro Gly Lys Gly Leu Glu Trp Val Ser
                165                 170                 175

Thr Val Asn Thr Asn Gly Leu Ile Thr Arg Tyr Ala Asp Ser Val Lys
            180                 185                 190

Gly Arg Phe Thr Ile Ser Arg Asp Asn Ala Lys Tyr Thr Leu Tyr Leu
        195                 200                 205

Gln Met Asn Ser Leu Lys Ser Glu Asp Thr Ala Val Tyr Tyr Cys Thr
    210                 215                 220

Lys Val Leu Pro Pro Tyr Ser Asp Asp Ser Arg Thr Asn Ala Asp Trp
225                 230                 235                 240

Gly Gln Gly Thr Gln Val Thr Val Ser Ser
                245                 250
```

<210> SEQ ID NO 41
<211> LENGTH: 250
<212> TYPE: PRT
<213> ORGANISM: Lama glama

<400> SEQUENCE: 41

```
Gln Val Gln Leu Gln Glu Ser Gly Gly Gly Leu Val Gln Pro Gly Asn
1               5                   10                  15

Ser Leu Arg Leu Ser Cys Ala Ala Ser Gly Phe Thr Phe Arg Asn Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asn Thr Ile Tyr Ala Asp Ser Val
    50                  55                  60

Lys Asp Arg Phe Thr Ile Ser Arg Asp Asn Ala Lys Ser Thr Leu Tyr
65                  70                  75                  80
```

```
Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser Glu Pro Lys Thr Pro Lys Pro Gln Pro Ala Ala Ala Gln
            115                 120                 125

Val Gln Leu Gln Glu Ser Gly Gly Leu Val Gln Pro Gly Gly Ser
        130                 135                 140

Leu Arg Leu Ser Cys Ala Ala Ser Gly Phe Glu Phe Glu Asn His Trp
145                 150                 155                 160

Met Tyr Trp Val Arg Gln Ala Pro Gly Lys Gly Leu Glu Trp Val Ser
                165                 170                 175

Thr Val Asn Thr Asn Gly Leu Ile Thr Arg Tyr Ala Asp Ser Val Lys
            180                 185                 190

Gly Arg Phe Thr Ile Ser Arg Asp Asn Ala Lys Tyr Thr Leu Tyr Leu
            195                 200                 205

Gln Met Asn Ser Leu Lys Ser Glu Asp Thr Ala Val Tyr Tyr Cys Thr
        210                 215                 220

Lys Val Leu Pro Pro Tyr Ser Asp Asp Ser Arg Thr Asn Ala Asp Trp
225                 230                 235                 240

Gly Gln Gly Thr Gln Val Thr Val Ser Ser
                245                 250

<210> SEQ ID NO 42
<211> LENGTH: 249
<212> TYPE: PRT
<213> ORGANISM: Lama glama

<400> SEQUENCE: 42

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Ser Gln Gly Thr Gln Val Thr Val
            100                 105                 110

Ser Ser Glu Pro Lys Thr Pro Lys Pro Gln Pro Ala Ala Ala Gln Val
            115                 120                 125

Gln Leu Gln Glu Ser Gly Gly Gly Leu Val Gln Pro Gly Gly Ser Leu
        130                 135                 140

Arg Leu Ser Cys Ala Ala Ser Gly Phe Glu Phe Glu Asn His Trp Met
145                 150                 155                 160

Tyr Trp Val Arg Gln Ala Pro Gly Lys Gly Leu Glu Trp Val Ser Thr
                165                 170                 175

Val Asn Thr Asn Gly Leu Ile Thr Arg Tyr Ala Asp Ser Val Lys Gly
            180                 185                 190

Arg Phe Thr Ile Ser Arg Asp Asn Ala Lys Tyr Thr Leu Tyr Leu Gln
```

```
            195                 200                 205
Met Asn Ser Leu Lys Ser Glu Asp Thr Ala Val Tyr Tyr Cys Thr Lys
        210                 215                 220

Val Leu Pro Pro Tyr Ser Asp Asp Ser Arg Thr Asn Ala Asp Trp Gly
225                 230                 235                 240

Gln Gly Thr Gln Val Thr Val Ser Ser
                245

<210> SEQ ID NO 43
<211> LENGTH: 249
<212> TYPE: PRT
<213> ORGANISM: Lama glama

<400> SEQUENCE: 43

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ala Ile Ser Ala Asp Gly Ser Asp Lys Arg Tyr Ala Asp Ser Val
    50                  55                  60

Lys Gly Arg Phe Thr Ile Ser Arg Asp Asn Gly Lys Lys Met Leu Thr
65                  70                  75                  80

Leu Asp Met Asn Ser Leu Lys Pro Glu Asp Thr Ala Val Tyr Tyr Cys
                85                  90                  95

Val Ile Gly Arg Gly Ser Pro Ala Ser Gln Gly Thr Gln Val Thr Val
            100                 105                 110

Ser Ser Glu Pro Lys Thr Pro Lys Pro Gln Pro Ala Ala Ala Gln Val
        115                 120                 125

Gln Leu Gln Glu Ser Gly Gly Gly Leu Val Gln Pro Gly Gly Ser Leu
    130                 135                 140

Arg Leu Ser Cys Ala Ala Ser Gly Phe Glu Phe Glu Asn His Trp Met
145                 150                 155                 160

Tyr Trp Val Arg Gln Ala Pro Gly Lys Gly Leu Glu Trp Val Ser Thr
                165                 170                 175

Val Asn Thr Asn Gly Leu Ile Thr Arg Tyr Ala Asp Ser Val Lys Gly
            180                 185                 190

Arg Phe Thr Ile Ser Arg Asp Asn Ala Lys Tyr Thr Leu Tyr Leu Gln
        195                 200                 205

Met Asn Ser Leu Lys Ser Glu Asp Thr Ala Val Tyr Tyr Cys Thr Lys
    210                 215                 220

Val Leu Pro Pro Tyr Ser Asp Asp Ser Arg Thr Asn Ala Asp Trp Gly
225                 230                 235                 240

Gln Gly Thr Gln Val Thr Val Ser Ser
                245

<210> SEQ ID NO 44
<211> LENGTH: 124
<212> TYPE: PRT
<213> ORGANISM: Lama glama

<400> SEQUENCE: 44

Gln Val Gln Leu Gln Asp Ser Gly Gly Gly Thr Val Gln Ala Gly Gly
1               5                   10                  15

Ser Leu Arg Leu Ser Cys Ala Ala Ser Gly Arg Thr Phe Ser Asp Tyr
```

```
            20                  25                  30
Ala Val Gly Trp Phe Arg Gln Ala Pro Gly Lys Glu Arg Glu Phe Val
            35                  40                  45

Ala Arg Ile Leu Trp Thr Gly Ala Ser Arg Ser Tyr Ala Asn Ser Val
        50                  55                  60

Asp Gly Arg Phe Thr Val Ser Thr Asp Asn Ala Lys Asn Thr Val Tyr
 65                  70                  75                  80

Leu Gln Met Asn Ser Leu Lys Pro Glu Asp Thr Ala Ile Tyr Tyr Cys
                85                  90                  95

Ala Ala Leu Pro Ser Asn Ile Ile Thr Thr Asp Tyr Leu Arg Val Tyr
               100                 105                 110

Tyr Trp Gly Gln Gly Thr Gln Val Thr Val Ser Ser
               115                 120

<210> SEQ ID NO 45
<211> LENGTH: 123
<212> TYPE: PRT
<213> ORGANISM: Lama glama

<400> SEQUENCE: 45

Gln Val Gln Leu Gln Asp Ser Gly Gly Gly Thr Val Gln Ala Gly Gly
 1               5                  10                  15

Ser Leu Arg Leu Ser Cys Ala Ala Ser Gly Arg Thr Phe Ser Asn Tyr
                20                  25                  30

Ala Val Gly Trp Phe Arg Gln Ala Pro Gly Lys Glu Arg Glu Phe Val
            35                  40                  45

Ala Arg Ile Lys Trp Ser Gly Ser Arg Ser Tyr Ala Asn Ser Val
        50                  55                  60

Asp Gly Arg Phe Thr Val Ser Thr Asp Asn Ala Lys Asn Thr Val Tyr
 65                  70                  75                  80

Leu Gln Met Asn Ser Leu Lys Pro Glu Asp Thr Ala Ile Tyr Tyr Cys
                85                  90                  95

Ala Leu Pro Ser Asn Ile Ile Thr Thr Asp Tyr Leu Arg Val Tyr Tyr
               100                 105                 110

Trp Gly Gln Gly Thr Gln Val Thr Val Ser Ser
               115                 120

<210> SEQ ID NO 46
<211> LENGTH: 118
<212> TYPE: PRT
<213> ORGANISM: Lama glama

<400> SEQUENCE: 46

Gln Val Gln Leu Gln Glu Ser Gly Gly Gly Leu Val Gln Ala Gly Gly
 1               5                  10                  15

Ser Leu Arg Leu Ser Cys Ala Ala Ala Gly Ile Ser Gly Ser Val Phe
                20                  25                  30

Ser Arg Thr Pro Met Gly Trp Tyr Arg Gln Ala Pro Gly Lys Gln Arg
            35                  40                  45

Glu Leu Val Ala Gly Ile Leu Thr Gly Ala Thr Ser Tyr Ala Glu
        50                  55                  60

Ser Val Lys Gly Arg Phe Thr Ile Ser Arg Asp Asn Ala Lys Asn Thr
 65                  70                  75                  80

Val Tyr Leu Gln Met Asn Ser Leu Ser Pro Glu Asp Thr Ala Glu Tyr
                85                  90                  95

Tyr Cys Asn Thr Tyr Pro Thr Trp Val Leu Ser Trp Gly Gln Gly Thr
```

Gln Val Thr Val Ser Ser
        115

<210> SEQ ID NO 47
<211> LENGTH: 118
<212> TYPE: PRT
<213> ORGANISM: Lama glama

<400> SEQUENCE: 47

Gln Val Gln Leu Gln Asp Ser Gly Gly Gly Leu Val Gln Ala Gly Gly
1               5                   10                  15

Ser Leu Arg Leu Ser Cys Ala Ala Gly Ile Ser Gly Ser Val Phe
        20                  25                  30

Ser Arg Thr Pro Met Gly Trp Tyr Arg Gln Ala Pro Gly Lys Gln Arg
        35                  40                  45

Glu Leu Val Ala Gly Ile Leu Ser Ser Gly Ala Thr Val Tyr Ala Glu
        50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Ser Pro Glu Asp Thr Ala Glu Tyr
                85                  90                  95

Tyr Cys Asn Thr Tyr Pro Thr Trp Val Leu Ser Trp Gly Gln Gly Thr
            100                 105                 110

Gln Val Thr Val Ser Ser
        115

<210> SEQ ID NO 48
<211> LENGTH: 118
<212> TYPE: PRT
<213> ORGANISM: Lama glama

<400> SEQUENCE: 48

Gln Val Gln Leu Gln Glu Ser Gly Gly Gly Leu Val Gln Ala Gly Gly
1               5                   10                  15

Ser Leu Arg Leu Ser Cys Ala Ala Gly Ile Ser Gly Ser Val Phe
        20                  25                  30

Ser Arg Thr Pro Met Gly Trp Tyr Arg Gln Ala Pro Gly Lys Gln Arg
        35                  40                  45

Glu Leu Val Ala Gly Ile Leu Ser Ser Gly Ala Thr Ala Tyr Ala Glu
        50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Ser Pro Glu Asp Thr Ala Glu Tyr
                85                  90                  95

Tyr Cys Asn Thr Tyr Pro Thr Trp Val Leu Ser Trp Gly Gln Gly Thr
            100                 105                 110

Gln Val Thr Val Ser Ser
        115

<210> SEQ ID NO 49
<211> LENGTH: 113
<212> TYPE: PRT
<213> ORGANISM: Lama glama

<400> SEQUENCE: 49

Gln Val Gln Leu Gln Glu Ser Gly Gly Gly Leu Val Gln Pro Gly Glu
1               5                   10                  15

```
Ser Leu Arg Leu Ser Cys Ala Ala Ser Arg Gly Ile Phe Arg Phe Asn
            20                  25                  30

Ala Gly Gly Trp Tyr Arg Gln Ala Pro Gly Lys Gln Arg Glu Leu Val
        35                  40                  45

Ala Phe Ile Gly Val Asp Asn Thr Thr Arg Tyr Ile Asp Ser Val Lys
    50                  55                  60

Gly Arg Phe Thr Ile Ser Arg Asp Asn Ala Lys Thr Thr Val Tyr Leu
65                  70                  75                  80

Gln Met Asn Ser Leu Gln Pro Glu Asp Thr Ala Val Tyr Tyr Cys Asn
                85                  90                  95

Lys Val Pro Tyr Ile Asp Trp Gly Gln Gly Thr Gln Val Thr Val Ser
            100                 105                 110

Ser

<210> SEQ ID NO 50
<211> LENGTH: 126
<212> TYPE: PRT
<213> ORGANISM: Lama glama

<400> SEQUENCE: 50

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Asn Met Gly Trp Phe Arg Gln Ala Pro Gly Lys Glu Arg Glu Phe Val
        35                  40                  45

Ala Gly Ile Ser Trp Asn Gly Gly Ser Ile Tyr Tyr Thr Ser Ser Val
    50                  55                  60

Glu Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Gly Val Tyr Tyr Cys
                85                  90                  95

Ala Ser Lys Gly Arg Pro Tyr Gly Val Pro Ser Pro Arg Gln Gly Asp
            100                 105                 110

Tyr Asp Tyr Trp Gly Gln Gly Thr Gln Val Thr Val Ser Ser
        115                 120                 125

<210> SEQ ID NO 51
<211> LENGTH: 126
<212> TYPE: PRT
<213> ORGANISM: Lama glama

<400> SEQUENCE: 51

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Asn Met Gly Trp Phe Arg Gln Ala Pro Gly Lys Glu Arg Glu Phe Val
        35                  40                  45

Ala Gly Ile Ser Trp Asn Gly Gly Ser Ile Tyr Tyr Thr Ser Ser Val
    50                  55                  60

Glu Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Gly Val Tyr Tyr Cys
                85                  90                  95
```

```
Ala Ser Lys Gly Arg Pro Tyr Gly Val Pro Ser Pro Arg Gln Gly Asp
            100                 105                 110

Tyr Asp Tyr Trp Gly Gln Gly Thr Gln Val Thr Val Ser Ser
            115                 120                 125
```

<210> SEQ ID NO 52
<211> LENGTH: 126
<212> TYPE: PRT
<213> ORGANISM: Lama glama

<400> SEQUENCE: 52

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ile Tyr
            20                  25                  30

Asn Met Gly Trp Phe Arg Gln Ala Pro Gly Lys Glu Arg Glu Phe Val
            35                  40                  45

Ala Ala Ile Ser Trp Asn Gly Gly Ser Ile Tyr Tyr Thr Ser Ser Val
        50                  55                  60

Glu Gly Arg Phe Thr Ile Ser Arg Asp Asn Ala Ile Asn Thr Val Tyr
65                  70                  75                  80

Leu Gln Met Asn Ser Leu Lys Pro Glu Asp Thr Gly Val Tyr Tyr Cys
                85                  90                  95

Ala Ser Lys Gly Arg Pro Tyr Gly Val Pro Ser Pro Arg Gln Gly Glu
            100                 105                 110

Tyr Asp Tyr Trp Gly Gln Gly Thr Gln Val Thr Val Ser Ser
            115                 120                 125
```

<210> SEQ ID NO 53
<211> LENGTH: 126
<212> TYPE: PRT
<213> ORGANISM: Lama glama

<400> SEQUENCE: 53

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Asn Ile Tyr
            20                  25                  30

Asn Met Gly Trp Phe Arg Gln Ala Pro Gly Lys Glu Arg Asp Phe Val
            35                  40                  45

Ala Ala Ile Ser Trp Asn Gly Gly Ser Ile Tyr Tyr Thr Ser Ser Val
        50                  55                  60

Glu Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Gly Val Tyr Tyr Cys
                85                  90                  95

Ala Ser Lys Gly Arg Pro Tyr Gly Val Pro Ser Pro Arg Gln Gly Asp
            100                 105                 110

Tyr Asp Tyr Trp Gly Gln Gly Thr Gln Val Thr Val Ser Ser
            115                 120                 125
```

<210> SEQ ID NO 54
<211> LENGTH: 126
<212> TYPE: PRT
<213> ORGANISM: Lama glama

<400> SEQUENCE: 54

```
Gln Val Lys Leu Glu Glu Ser Gly Gly Gly Leu Val Gln Ala Gly Gly
```

```
                1               5                   10                  15
            Ser Leu Arg Leu Ser Cys Ala Ala Ser Gly Arg Thr Phe Asn Asn Tyr
                        20                  25                  30

Asn Met Gly Trp Phe Arg Gln Ala Pro Gly Lys Glu Arg Glu Phe Val
                        35                  40                  45

Ala Ala Ile Ser Trp Asn Gly Ser Thr Tyr Tyr Asp Asp Ser Val
                        50                  55                  60

Lys Gly Arg Phe Thr Ile Ser Arg Asp Asn Ala Asn Asn Leu Val Tyr
             65                 70                  75                  80

Leu Gln Met Asn Ser Leu Asn Phe Glu Asp Thr Ala Val Tyr Tyr Cys
                        85                  90                  95

Ala Cys Ala Ala Asn Pro Tyr Gly Ile Pro Gln Tyr Arg Glu Asn Arg
                        100                 105                 110

Tyr Asp Phe Trp Gly Gln Gly Thr Gln Val Thr Val Ser Ser
                        115                 120                 125
```

<210> SEQ ID NO 55
<211> LENGTH: 126
<212> TYPE: PRT
<213> ORGANISM: Lama glama

<400> SEQUENCE: 55

```
            Gln Val Gln Leu Gln Glu Ser Gly Gly Leu Val Gln Ala Gly Gly
             1              5                   10                  15

Ser Leu Arg Leu Ser Cys Ala Ala Ser Gly Arg Thr Phe Asp Asn Tyr
                        20                  25                  30

Asn Met Gly Trp Phe Arg Gln Ala Pro Gly Lys Glu Arg Glu Phe Val
                        35                  40                  45

Ala Ala Ile Ser Trp Asn Gly Gly Ser Thr Tyr Tyr Asp Asp Ser Val
                        50                  55                  60

Lys Gly Arg Phe Thr Ile Ser Arg Asp Asn Phe Gln Lys Leu Val Tyr
             65                 70                  75                  80

Leu Gln Met Asn Ser Leu Lys Leu Glu Asp Thr Ala Val Tyr Tyr Cys
                        85                  90                  95

Ala Cys Ala Ala Asn Pro Tyr Gly Ile Pro Gln Tyr Arg Glu Asn Arg
                        100                 105                 110

Tyr Asp Phe Trp Gly Gln Gly Thr Gln Val Thr Val Ser Ser
                        115                 120                 125
```

<210> SEQ ID NO 56
<211> LENGTH: 128
<212> TYPE: PRT
<213> ORGANISM: Lama glama

<400> SEQUENCE: 56

```
            Gln Val Gln Leu Val Glu Ser Gly Gly Arg Leu Val Gln Ala Gly Gly
             1              5                   10                  15

Ser Leu Arg Leu Ser Cys Ile Ala Ser Gly Arg Thr Ile Ser Asp Tyr
                        20                  25                  30

Ala Ala Gly Trp Phe Arg Gln Ala Pro Gly Lys Glu Arg Glu Phe Leu
                        35                  40                  45

Ala Ser Val Thr Trp Gly Phe Gly Ser Thr Ser Tyr Ala Asp Ser Val
                        50                  55                  60

Lys Gly Arg Phe Thr Ile Ser Arg Asp Lys Ala Lys Asp Thr Val Tyr
             65                 70                  75                  80

Leu Gln Met Asn Thr Leu Glu Pro Asp Asp Thr Ser Val Tyr Tyr Cys
```

85                  90                  95

Ala Ser Ser Pro Arg Tyr Cys Ala Gly Tyr Arg Cys Tyr Val Thr Ala
                100                 105                 110

Ser Glu Phe Asp Ser Trp Gly Gln Gly Thr Gln Val Thr Val Ser Ser
                115                 120                 125

<210> SEQ ID NO 57
<211> LENGTH: 128
<212> TYPE: PRT
<213> ORGANISM: Lama glama

<400> SEQUENCE: 57

Gln Val Lys Leu Glu Glu Ser Gly Gly Arg Leu Val Gln Ala Gly Gly
1               5                   10                  15

Ser Leu Arg Leu Ser Cys Ile Ala Ser Gly Arg Thr Ile Ser Asp Tyr
                20                  25                  30

Ala Ala Gly Trp Phe Arg Gln Ala Pro Gly Lys Glu Arg Glu Phe Leu
            35                  40                  45

Ala Ser Val Ser Trp Gly Phe Gly Ser Thr Tyr Tyr Ala Asp Ser Val
        50                  55                  60

Lys Gly Arg Phe Thr Ile Ser Arg Asp Thr Ala Lys Asp Thr Val Tyr
65                  70                  75                  80

Leu Gln Met Asn Thr Leu Glu Pro Asp Asp Thr Ser Val Tyr Tyr Cys
                85                  90                  95

Ala Ser Ser Pro Arg Tyr Cys Ala Gly Tyr Arg Cys Tyr Ala Thr Ala
                100                 105                 110

Ser Glu Phe Asp Ser Trp Gly Gln Gly Thr Gln Val Thr Val Ser Ser
                115                 120                 125

<210> SEQ ID NO 58
<211> LENGTH: 128
<212> TYPE: PRT
<213> ORGANISM: Lama glama

<400> SEQUENCE: 58

Gln Val Gln Leu Gln Glu Ser Gly Gly Arg Leu Val Gln Ala Gly Gly
1               5                   10                  15

Ser Leu Arg Leu Ser Cys Ile Ala Ser Gly Arg Thr Ile Ser Asp Tyr
                20                  25                  30

Ala Ala Gly Trp Phe Arg Gln Ala Pro Gly Lys Glu Arg Glu Phe Leu
            35                  40                  45

Ala Ser Val Thr Trp Gly Phe Gly Ser Thr Tyr Tyr Ala Asp Ser Val
        50                  55                  60

Lys Gly Arg Phe Thr Ile Ser Arg Asp Lys Ala Lys Asp Thr Val Tyr
65                  70                  75                  80

Leu Gln Met Asn Thr Leu Glu Pro Asp Asp Thr Ser Ala Tyr Tyr Cys
                85                  90                  95

Ala Ser Ser Pro Arg Tyr Cys Ala Gly Tyr Arg Cys Tyr Val Thr Ala
                100                 105                 110

Ser Glu Phe Asp Ser Trp Gly Pro Gly Thr Gln Val Thr Val Ser Ser
                115                 120                 125

<210> SEQ ID NO 59
<211> LENGTH: 126
<212> TYPE: PRT
<213> ORGANISM: Lama glama

<400> SEQUENCE: 59

-continued

```
Gln Val Gln Leu Gln Asp Ser Gly Gly Gly Leu Val Gln Ala Gly Asp
1               5                   10                  15

Ser Leu Arg Leu Ser Cys Ala Ala Ser Gly Arg Ser Phe Ser Ser Tyr
            20                  25                  30

Gly Met Gly Trp Phe Arg Gln Ala Pro Gly Lys Glu His Glu Phe Val
        35                  40                  45

Ala Gly Ile Trp Arg Ser Gly Val Ser Leu Tyr Tyr Thr Asp Ser Val
    50                  55                  60

Lys Gly Arg Phe Thr Ile Ser Arg Asp Asp Ala Lys Met Thr Val Ser
65                  70                  75                  80

Leu Gln Met Asn Ser Leu Lys Pro Glu Asp Thr Ala Val Tyr Tyr Cys
                85                  90                  95

Ala Ala Glu Ala Thr Phe Pro Thr Trp Ser Arg Gly Arg Phe Ala Asp
            100                 105                 110

Tyr Asp Tyr Arg Gly Gln Gly Thr Gln Val Thr Val Ser Ser
            115                 120                 125
```

<210> SEQ ID NO 60
<211> LENGTH: 126
<212> TYPE: PRT
<213> ORGANISM: Lama glama

<400> SEQUENCE: 60

```
Gln Val Gln Leu Gln Glu Ser Gly Gly Gly Leu Val Gln Ala Gly Asp
1               5                   10                  15

Ser Leu Arg Leu Ser Cys Thr Ala Ser Gly Arg Ser Phe Ser Ser Tyr
            20                  25                  30

Gly Met Gly Trp Phe Arg Gln Ala Pro Gly Lys Asp His Glu Phe Val
        35                  40                  45

Ala Gly Ile Trp Arg Ser Gly Val Ser Leu Tyr Tyr Ala Asp Ser Val
    50                  55                  60

Lys Gly Arg Phe Thr Ile Ser Arg Asp Asp Ala Lys Met Thr Val Ser
65                  70                  75                  80

Leu Gln Met Asn Gly Leu Lys Pro Glu Asp Thr Ala Val Tyr Tyr Cys
                85                  90                  95

Ala Ala Glu Ala Thr Phe Pro Thr Trp Asn Arg Gly Thr Phe Ala Asp
            100                 105                 110

Tyr Asp Tyr Arg Gly Gln Gly Thr Gln Val Thr Val Ser Ser
            115                 120                 125
```

<210> SEQ ID NO 61
<211> LENGTH: 126
<212> TYPE: PRT
<213> ORGANISM: Lama glama

<400> SEQUENCE: 61

```
Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Ser Phe Ser Ser Tyr
            20                  25                  30

Gly Met Gly Trp Phe Arg Gln Ala Pro Gly Lys Glu His Glu Phe Val
        35                  40                  45

Ala Gly Ile Trp Arg Ser Gly Val Ser Leu Tyr Tyr Ala Asp Ser Val
    50                  55                  60

Lys Gly Arg Phe Thr Ile Ser Arg Asp Asp Ala Lys Met Thr Val Ser
65                  70                  75                  80
```

-continued

Leu Gln Met Asn Gly Leu Lys Pro Glu Asp Thr Ala Val Tyr Tyr Cys
                85                  90                  95

Ala Ala Glu Ala Thr Phe Pro Thr Trp Asn Arg Gly Ser Phe Ala Asp
            100                 105                 110

Tyr Asp Tyr Arg Gly Gln Gly Thr Gln Val Thr Val Ser Ser
        115                 120                 125

<210> SEQ ID NO 62
<211> LENGTH: 126
<212> TYPE: PRT
<213> ORGANISM: Lama glama

<400> SEQUENCE: 62

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Ser Phe Ser Ser Tyr
                20                  25                  30

Gly Met Gly Trp Phe Arg Gln Ala Pro Gly Lys Glu His Glu Phe Val
            35                  40                  45

Ala Gly Ile Trp Arg Ser Gly Val Ser Leu Tyr Tyr Ala Asp Ser Val
        50                  55                  60

Lys Gly Arg Phe Thr Ile Ser Arg Asp Asp Ala Lys Met Thr Val Ser
65                  70                  75                  80

Leu Gln Met Asn Ser Leu Lys Pro Glu Asp Thr Ala Val Tyr Tyr Cys
                85                  90                  95

Ala Ala Glu Ala Thr Phe Pro Thr Trp Asn Arg Gly Arg Phe Ala Asp
            100                 105                 110

Tyr Asp Tyr Ser Gly Gln Gly Thr Gln Val Thr Val Ser Ser
        115                 120                 125

<210> SEQ ID NO 63
<211> LENGTH: 120
<212> TYPE: PRT
<213> ORGANISM: Lama glama

<400> SEQUENCE: 63

Ala Val Gln Leu Val Glu Ser Gly Gly Gly Leu Val Gln Thr Gly Asp
1               5                   10                  15

Ser Leu Arg Leu Ser Cys Val Ala Ser Gly Gly Thr Phe Ser Arg Tyr
                20                  25                  30

Ala Met Gly Trp Phe Arg Gln Ala Pro Gly Lys Glu Arg Glu Phe Val
            35                  40                  45

Ala Arg Ile Gly Tyr Ser Gly Arg Ser Ile Ser Tyr Ala Thr Ser Val
        50                  55                  60

Glu Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ser Leu Val Ser Gly Thr Leu Tyr Gln Ala Asp Tyr Trp Gly Gln
            100                 105                 110

Gly Thr Gln Val Thr Val Ser Ser
        115                 120

<210> SEQ ID NO 64
<211> LENGTH: 120
<212> TYPE: PRT
<213> ORGANISM: Lama glama

<400> SEQUENCE: 64

Gln Val Gln Leu Val Glu Ser Gly Gly Leu Val Gln Thr Gly Asp
1               5                   10                  15

Ser Leu Arg Leu Ser Cys Val Ala Ser Gly Gly Thr Phe Ser Arg Tyr
            20                  25                  30

Ala Met Gly Trp Phe Arg Gln Pro Pro Gly Lys Glu Arg Asp Phe Val
        35                  40                  45

Ala Arg Ile Gly Tyr Ser Gly Gln Ser Ile Ser Tyr Ala Thr Ser Val
    50                  55                  60

Glu Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ser Leu Val Ser Gly Thr Leu Tyr Lys Pro Asn Tyr Trp Gly Gln
            100                 105                 110

Gly Thr Gln Val Thr Val Ser Ser
        115                 120

<210> SEQ ID NO 65
<211> LENGTH: 121
<212> TYPE: PRT
<213> ORGANISM: Lama glama

<400> SEQUENCE: 65

Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Thr Tyr Thr Val Gly
            20                  25                  30

Trp Phe Arg Gln Ala Pro Gly Lys Glu Arg Glu Phe Val Ala Ala Ile
        35                  40                  45

Ser Trp Ser Gly Gly Ser Ala Leu Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Gly Ser Leu Glu Pro Glu Asp Thr Ala Tyr Tyr Ser Cys Ala Ala Pro
                85                  90                  95

Gly Thr Arg Tyr Tyr Gly Ser Asn Gln Val Tyr Asn Tyr Trp Gly
            100                 105                 110

Gln Gly Thr Gln Val Thr Val Ser Ser
        115                 120

<210> SEQ ID NO 66
<211> LENGTH: 121
<212> TYPE: PRT
<213> ORGANISM: Lama glama

<400> SEQUENCE: 66

Gln Val Lys Leu Glu Glu Ser Gly Gly Gly Leu Val Gln Ala Gly Asp
1               5                   10                  15

Ser Leu Arg Leu Ser Cys Ala Ala Ser Gly Leu Thr Tyr Thr Val Gly
            20                  25                  30

Trp Phe Arg Gln Ala Pro Gly Lys Glu Arg Glu Phe Val Ala Ala Ile
        35                  40                  45

Asp Trp Ser Gly Gly Ser Ala Leu Tyr Ala Asp Ser Val Lys Gly Arg
    50                  55                  60

```
Phe Thr Ile Ser Arg Asp Asn Thr Lys Asn Thr Val Tyr Leu Gln Met
 65                  70                  75                  80

Gly Ser Leu Glu Pro Glu Asp Thr Ala Val Tyr Trp Cys Ala Ala Pro
                 85                  90                  95

Gly Thr Arg Tyr His Gly Arg Asn Gln Val Asn Tyr Asn Tyr Trp Gly
            100                 105                 110

Gln Gly Thr Gln Val Thr Val Ser Ser
            115                 120

<210> SEQ ID NO 67
<211> LENGTH: 116
<212> TYPE: PRT
<213> ORGANISM: Lama glama

<400> SEQUENCE: 67

Gln Val Gln Leu Gln Glu Ser Gly Gly Gly Leu Val Gln Pro Gly Gly
  1               5                  10                  15

Ser Leu Arg Leu Ser Cys Ala Ala Ser Gly Phe Thr Ser Ser Asn Tyr
             20                  25                  30

Ala Met Ser Trp Val Arg Gln Ala Pro Gly Lys Gly Leu Glu Trp Val
         35                  40                  45

Ser Ser Ile Asn Ser Arg Thr Gly Ser Ile Thr Tyr Ala Asp Ser Val
 50                  55                  60

Lys Gly Arg Phe Thr Ile Thr Leu Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Ser Arg Val Asp Asp Arg Val Ser Arg Gly Gln Gly Thr Gln Val
            100                 105                 110

Thr Val Ser Ser
            115

<210> SEQ ID NO 68
<211> LENGTH: 120
<212> TYPE: PRT
<213> ORGANISM: Lama glama

<400> SEQUENCE: 68

Gln Val Gln Leu Val Glu Ser Gly Gly Gly Leu Val Gln Ala Gly Gly
  1               5                  10                  15

Ser Leu Arg Leu Ser Cys Ala Ala Ser Gly Arg Thr Ile Ser Ser Phe
             20                  25                  30

Arg Met Gly Trp Phe Arg Arg Ala Pro Gly Glu Glu Arg Glu Phe Val
         35                  40                  45

Ala Phe Val Arg Ser Asn Gly Thr Ser Thr Tyr Tyr Ala Asp Ser Val
 50                  55                  60

Glu Gly Arg Phe Thr Ile Thr Arg Asp Asn Ala Lys Asn Thr Val Tyr
 65                  70                  75                  80

Leu Arg Met Asp Ser Leu Lys Pro Glu Asp Thr Ala Val Tyr Tyr Cys
                 85                  90                  95

Ala Ala Ala Thr Arg Asp Tyr Gly Gly Ser Phe Asp Tyr Trp Gly Gln
            100                 105                 110

Gly Thr Gln Val Thr Val Ser Ser
            115                 120

<210> SEQ ID NO 69
<211> LENGTH: 120
```

```
<212> TYPE: PRT
<213> ORGANISM: Lama glama

<400> SEQUENCE: 69

Gln Val Gln Leu Gln Asp Ser Gly Gly Gly Leu Val Gln Ala Gly Gly
1               5                   10                  15

Ser Leu Arg Leu Ser Cys Ala Ala Ser Gly Arg Thr Phe Ser Ser Phe
            20                  25                  30

Arg Met Gly Trp Phe Arg Ala Pro Gly Glu Glu Arg Glu Phe Val
        35                  40                  45

Ala Phe Val Arg Ser Asn Gly Thr Ser Thr Tyr Tyr Ala Asp Ser Val
    50                  55                  60

Glu Gly Arg Phe Thr Ile Thr Arg Asp Asn Ala Lys Asn Thr Val Tyr
65                  70                  75                  80

Leu Arg Met Asp Ser Leu Lys Pro Glu Asp Thr Ala Val Tyr Tyr Cys
                85                  90                  95

Ala Ala Ala Thr Arg Asp Tyr Gly Gly Ser Phe Asp Tyr Trp Gly Gln
            100                 105                 110

Gly Thr Gln Val Ile Val Ser Ser
        115                 120

<210> SEQ ID NO 70
<211> LENGTH: 116
<212> TYPE: PRT
<213> ORGANISM: Lama glama

<400> SEQUENCE: 70

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Met Ser Trp Val Arg Gln Pro Pro Gly Lys Gly Ile Glu Trp Val
        35                  40                  45

Ser Ser Ile Asn Asn Arg Asn Asp His Ile Thr Tyr Ala Asp Ser Val
    50                  55                  60

Lys Gly Arg Phe Thr Ile Ala Arg Asp Asn Ala Asn Asn Ile Leu Tyr
65                  70                  75                  80

Leu Gln Met Asn Ser Leu Lys Pro Glu Asp Thr Ala Val Tyr Tyr Cys
                85                  90                  95

Ala Ser Arg Val Asp Asp Arg Val Ser Arg Gly Gln Gly Thr Gln Val
            100                 105                 110

Thr Val Ser Ser
        115

<210> SEQ ID NO 71
<211> LENGTH: 124
<212> TYPE: PRT
<213> ORGANISM: Lama glama

<400> SEQUENCE: 71

Gln Val Gln Leu Gln Asp Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Gly Met Ala Trp Phe Arg Gln Ala Pro Gly Lys Glu Arg Glu Leu Val
        35                  40                  45

Val Ala Ile Asn Arg Ser Gly Gly Ala Thr Ser Tyr Ala Thr Ser Val
```

```
                   50                  55                  60
Arg Gly Arg Phe Thr Ile Ser Arg Asp Asn Ala Lys Asn Thr Met Tyr
 65                  70                  75                  80

Leu Gln Met Asn Ser Leu Asn Pro Glu Asp Thr Ala Val Tyr Tyr Cys
                     85                  90                  95

Ala Ala Arg Asp Pro Thr Arg Thr Tyr Ser Ser Tyr Phe Glu Tyr Thr
                100                 105                 110

Tyr Trp Gly Gln Gly Thr Gln Val Thr Val Ser Ser
                115                 120

<210> SEQ ID NO 72
<211> LENGTH: 128
<212> TYPE: PRT
<213> ORGANISM: Lama glama

<400> SEQUENCE: 72

Gln Val Gln Leu Gln Glu Ser Gly Gly Gly Leu Val Gln Ala Gly Gly
  1               5                  10                  15

Ser Leu Thr Leu Ser Cys Val Ala Ser Gly Arg Thr Ile Ser Asp Tyr
                 20                  25                  30

Ala Val Gly Trp Phe Arg Gln Ala Pro Gly Lys Glu Arg Glu Phe Val
             35                  40                  45

Ala Ser Ile Ser Trp Gly Gly Phe Thr Ala Phe Ala Asp Ser Met
         50                  55                  60

Lys Gly Arg Phe Thr Ile Ser Arg Asp Asn Ala Lys Asn Thr Val Tyr
 65                  70                  75                  80

Leu Gln Thr His Thr Leu Glu Pro Asp Asp Thr Ser Val Tyr Tyr Cys
                 85                  90                  95

Ala Ser Ser Arg Arg Tyr Cys Thr Gly Tyr Arg Cys Tyr Ala Thr Ala
                100                 105                 110

Ser Glu Phe Asp Ser Trp Gly Gln Gly Thr Gln Val Thr Val Ser Ser
                115                 120                 125

<210> SEQ ID NO 73
<211> LENGTH: 260
<212> TYPE: PRT
<213> ORGANISM: Lama glama

<400> SEQUENCE: 73

Gln Val Gln Leu Gln Asp Ser Gly Gly Gly Leu Val Gln Ala Gly Gly
  1               5                  10                  15

Ser Leu Arg Leu Ser Cys Ala Ala Ser Gly Gly Thr Phe Ser Ser Ile
                 20                  25                  30

Ile Met Ala Trp Phe Arg Gln Ala Pro Gly Lys Glu Arg Glu Phe Val
             35                  40                  45

Gly Ala Val Ser Trp Ser Gly Gly Thr Thr Val Tyr Ala Asp Ser Val
         50                  55                  60

Leu Gly Arg Phe Glu Ile Ser Arg Asp Ser Ala Arg Lys Ser Val Tyr
 65                  70                  75                  80

Leu Gln Met Asn Ser Leu Lys Pro Glu Asp Thr Ala Val Tyr Tyr Cys
                 85                  90                  95

Ala Ala Arg Pro Tyr Gln Lys Tyr Asn Trp Ala Ser Ala Ser Tyr Asn
                100                 105                 110

Val Trp Gly Gln Gly Thr Gln Val Thr Val Ser Ser Glu Pro Lys Thr
                115                 120                 125

Pro Lys Pro Gln Pro Ala Ala Ala Gln Val Gln Leu Gln Asp Ser Gly
```

```
            130                 135                 140
Gly Gly Leu Val Gln Ala Gly Gly Ser Leu Arg Leu Ser Cys Ala Ala
145                 150                 155                 160

Ser Gly Gly Thr Phe Ser Ser Ile Ile Met Ala Trp Phe Arg Gln Ala
                    165                 170                 175

Pro Gly Lys Glu Arg Glu Phe Val Gly Ala Val Ser Trp Ser Gly Gly
                180                 185                 190

Thr Thr Val Tyr Ala Asp Ser Val Leu Gly Arg Phe Glu Ile Ser Arg
            195                 200                 205

Asp Ser Ala Arg Lys Ser Val Tyr Leu Gln Met Asn Ser Leu Lys Pro
        210                 215                 220

Glu Asp Thr Ala Val Tyr Tyr Cys Ala Ala Arg Pro Tyr Gln Lys Tyr
225                 230                 235                 240

Asn Trp Ala Ser Ala Ser Tyr Asn Val Trp Gly Gln Gly Thr Gln Val
                    245                 250                 255

Thr Val Ser Ser
            260

<210> SEQ ID NO 74
<211> LENGTH: 411
<212> TYPE: PRT
<213> ORGANISM: Lama glama

<400> SEQUENCE: 74

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asp His
                20                  25                  30

Ser Gly Tyr Thr Tyr Thr Ile Gly Trp Phe Arg Gln Ala Pro Gly Lys
            35                  40                  45

Glu Arg Glu Phe Val Ala Arg Ile Tyr Trp Ser Ser Gly Asn Thr Tyr
        50                  55                  60

Tyr Ala Asp Ser Val Lys Gly Arg Phe Ala Ile Ser Arg Asp Ile Ala
65                  70                  75                  80

Lys Asn Thr Val Asp Leu Thr Met Asn Asn Leu Glu Pro Glu Asp Thr
                85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser Glu Pro Lys Thr Pro Lys Pro Gln Pro Ala Ala Ala Gln Val Gln
    130                 135                 140

Leu Gln Glu Ser Gly Gly Gly Leu Val Gln Pro Gly Gly Ser Leu Arg
145                 150                 155                 160

Leu Ser Cys Ala Ala Ser Gly Arg Thr Phe Ser Asp His Ser Gly Tyr
                165                 170                 175

Thr Tyr Thr Ile Gly Trp Phe Arg Gln Ala Pro Gly Lys Glu Arg Glu
            180                 185                 190

Phe Val Ala Arg Ile Tyr Trp Ser Ser Gly Asn Thr Tyr Tyr Ala Asp
        195                 200                 205

Ser Val Lys Gly Arg Phe Ala Ile Ser Arg Asp Ile Ala Lys Asn Thr
    210                 215                 220

Val Asp Leu Thr Met Asn Asn Leu Glu Pro Glu Asp Thr Ala Val Tyr
225                 230                 235                 240
```

-continued

```
Tyr Cys Ala Ala Arg Asp Gly Ile Pro Thr Ser Arg Ser Val Glu Ser
                245                 250                 255

Tyr Asn Tyr Trp Gly Gln Gly Thr Gln Val Thr Val Ser Ser Glu Pro
        260                 265                 270

Lys Thr Pro Lys Pro Gln Pro Ala Ala Ala Gln Val Gln Leu Gln Glu
    275                 280                 285

Ser Gly Gly Gly Leu Val Gln Pro Gly Gly Ser Leu Arg Leu Ser Cys
290                 295                 300

Ala Ala Ser Gly Arg Thr Phe Ser Asp His Ser Gly Tyr Thr Tyr Thr
305                 310                 315                 320

Ile Gly Trp Phe Arg Gln Ala Pro Gly Lys Glu Arg Glu Phe Val Ala
                325                 330                 335

Arg Ile Tyr Trp Ser Ser Gly Asn Thr Tyr Tyr Ala Asp Ser Val Lys
            340                 345                 350

Gly Arg Phe Ala Ile Ser Arg Asp Ile Ala Lys Asn Thr Val Asp Leu
        355                 360                 365

Thr Met Asn Asn Leu Glu Pro Glu Asp Thr Ala Val Tyr Tyr Cys Ala
    370                 375                 380

Ala Arg Asp Gly Ile Pro Thr Ser Arg Ser Val Glu Ser Tyr Asn Tyr
385                 390                 395                 400

Trp Gly Gln Gly Thr Gln Val Thr Val Ser Ser
                405                 410

<210> SEQ ID NO 75
<211> LENGTH: 552
<212> TYPE: PRT
<213> ORGANISM: Lama glama

<400> SEQUENCE: 75

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asp His
            20                  25                  30

Ser Gly Tyr Thr Tyr Thr Ile Gly Trp Phe Arg Gln Ala Pro Gly Lys
        35                  40                  45

Glu Arg Glu Phe Val Ala Arg Ile Tyr Trp Ser Ser Gly Asn Thr Tyr
    50                  55                  60

Tyr Ala Asp Ser Val Lys Gly Arg Phe Ala Ile Ser Arg Asp Ile Ala
65                  70                  75                  80

Lys Asn Thr Val Asp Leu Thr Met Asn Asn Leu Glu Pro Glu Asp Thr
                85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser Glu Pro Lys Thr Pro Lys Pro Gln Pro Ala Ala Ala Gln Val Gln
    130                 135                 140

Leu Gln Glu Ser Gly Gly Gly Leu Val Gln Pro Gly Gly Ser Leu Arg
145                 150                 155                 160

Leu Ser Cys Ala Ala Ser Gly Arg Thr Phe Ser Asp His Ser Gly Tyr
                165                 170                 175

Thr Tyr Thr Ile Gly Trp Phe Arg Gln Ala Pro Gly Lys Glu Arg Glu
            180                 185                 190

Phe Val Ala Arg Ile Tyr Trp Ser Ser Gly Asn Thr Tyr Tyr Ala Asp
        195                 200                 205
```

-continued

Ser Val Lys Gly Arg Phe Ala Ile Ser Arg Asp Ile Ala Lys Asn Thr
210                 215                 220

Val Asp Leu Thr Met Asn Asn Leu Glu Pro Glu Asp Thr Ala Val Tyr
225                 230                 235                 240

Tyr Cys Ala Ala Arg Asp Gly Ile Pro Thr Ser Arg Ser Val Glu Ser
                245                 250                 255

Tyr Asn Tyr Trp Gly Gln Gly Thr Gln Val Thr Val Ser Ser Glu Pro
            260                 265                 270

Lys Thr Pro Lys Pro Gln Pro Ala Ala Gln Val Gln Leu Gln Glu
            275                 280                 285

Ser Gly Gly Gly Leu Val Gln Pro Gly Gly Ser Leu Arg Leu Ser Cys
290                 295                 300

Ala Ala Ser Gly Arg Thr Phe Ser Asp His Ser Gly Tyr Thr Tyr Thr
305                 310                 315                 320

Ile Gly Trp Phe Arg Gln Ala Pro Gly Lys Glu Arg Glu Phe Val Ala
                325                 330                 335

Arg Ile Tyr Trp Ser Ser Gly Asn Thr Tyr Tyr Ala Asp Ser Val Lys
                340                 345                 350

Gly Arg Phe Ala Ile Ser Arg Asp Ile Ala Lys Asn Thr Val Asp Leu
            355                 360                 365

Thr Met Asn Asn Leu Glu Pro Glu Asp Thr Ala Val Tyr Tyr Cys Ala
370                 375                 380

Ala Arg Asp Gly Ile Pro Thr Ser Arg Ser Val Glu Ser Tyr Asn Tyr
385                 390                 395                 400

Trp Gly Gln Gly Thr Gln Val Thr Val Ser Ser Glu Pro Lys Thr Pro
                405                 410                 415

Lys Pro Gln Pro Ala Ala Gln Val Gln Leu Gln Glu Ser Gly Gly
            420                 425                 430

Gly Leu Val Gln Pro Gly Gly Ser Leu Arg Leu Ser Cys Ala Ala Ser
            435                 440                 445

Gly Arg Thr Phe Ser Asp His Ser Gly Tyr Thr Tyr Thr Ile Gly Trp
            450                 455                 460

Phe Arg Gln Ala Pro Gly Lys Glu Arg Glu Phe Val Ala Arg Ile Tyr
465                 470                 475                 480

Trp Ser Ser Gly Asn Thr Tyr Tyr Ala Asp Ser Val Lys Gly Arg Phe
                485                 490                 495

Ala Ile Ser Arg Asp Ile Ala Lys Asn Thr Val Asp Leu Thr Met Asn
            500                 505                 510

Asn Leu Glu Pro Glu Asp Thr Ala Val Tyr Tyr Cys Ala Ala Arg Asp
            515                 520                 525

Gly Ile Pro Thr Ser Arg Ser Val Glu Ser Tyr Asn Tyr Trp Gly Gln
530                 535                 540

Gly Thr Gln Val Thr Val Ser Ser
545                 550

<210> SEQ ID NO 76
<211> LENGTH: 260
<212> TYPE: PRT
<213> ORGANISM: Lama glama

<400> SEQUENCE: 76

Gln Val Gln Leu Gln Asp Ser Gly Gly Gly Leu Val Gln Ala Gly Gly
1               5                   10                  15

Ser Leu Arg Leu Ser Cys Ala Ala Ser Gly Gly Thr Phe Ser Ser Ile

```
            20                  25                  30
Ile Met Ala Trp Phe Arg Gln Ala Pro Gly Lys Glu Arg Glu Phe Val
            35                  40                  45
Gly Ala Val Ser Trp Ser Gly Gly Thr Thr Val Tyr Ala Asp Ser Val
50                      55                  60
Leu Gly Arg Phe Glu Ile Ser Arg Asp Ser Ala Arg Lys Ser Val Tyr
65                  70                  75                  80
Leu Gln Met Asn Ser Leu Lys Pro Glu Asp Thr Ala Val Tyr Tyr Cys
                85                  90                  95
Ala Ala Arg Pro Tyr Gln Lys Tyr Asn Trp Ala Ser Ala Ser Tyr Asn
                100                 105                 110
Val Trp Gly Gln Gly Thr Gln Val Thr Val Ser Ser Glu Pro Lys Thr
            115                 120                 125
Pro Lys Pro Gln Pro Ala Ala Ala Gln Val Gln Leu Gln Asp Ser Gly
        130                 135                 140
Gly Gly Leu Val Gln Ala Gly Gly Ser Leu Arg Leu Ser Cys Ala Ala
145                 150                 155                 160
Ser Gly Gly Thr Phe Ser Ser Ile Ile Met Ala Trp Phe Arg Gln Ala
                165                 170                 175
Pro Gly Lys Glu Arg Glu Phe Val Gly Ala Val Ser Trp Ser Gly Gly
                180                 185                 190
Thr Thr Val Tyr Ala Asp Ser Val Leu Gly Arg Phe Glu Ile Ser Arg
            195                 200                 205
Asp Ser Ala Arg Lys Ser Val Tyr Leu Gln Met Asn Ser Leu Lys Pro
        210                 215                 220
Glu Asp Thr Ala Val Tyr Tyr Cys Ala Ala Arg Pro Tyr Gln Lys Tyr
225                 230                 235                 240
Asn Trp Ala Ser Ala Ser Tyr Asn Val Trp Gly Gln Gly Thr Gln Val
                245                 250                 255
Thr Val Ser Ser
            260

<210> SEQ ID NO 77
<211> LENGTH: 248
<212> TYPE: PRT
<213> ORGANISM: Lama glama

<400> SEQUENCE: 77

Gln Val Gln Leu Gln Asp Ser Gly Gly Gly Leu Val Gln Ala Gly Gly
1               5                   10                  15
Ser Leu Arg Leu Ser Cys Ala Ala Ser Gly Gly Thr Phe Ser Ser Ile
            20                  25                  30
Ile Met Ala Trp Phe Arg Gln Ala Pro Gly Lys Glu Arg Glu Phe Val
            35                  40                  45
Gly Ala Val Ser Trp Ser Gly Gly Thr Thr Val Tyr Ala Asp Ser Val
        50                  55                  60
Leu Gly Arg Phe Glu Ile Ser Arg Asp Ser Ala Arg Lys Ser Val Tyr
65                  70                  75                  80
Leu Gln Met Asn Ser Leu Lys Pro Glu Asp Thr Ala Val Tyr Tyr Cys
                85                  90                  95
Ala Ala Arg Pro Tyr Gln Lys Tyr Asn Trp Ala Ser Ala Ser Tyr Asn
                100                 105                 110
Val Trp Gly Gln Gly Thr Gln Val Thr Val Ser Ser Gln Val Gln Leu
            115                 120                 125
```

```
Gln Asp Ser Gly Gly Leu Val Gln Ala Gly Ser Leu Arg Leu
        130                 135                 140
Ser Cys Ala Ala Ser Gly Gly Thr Phe Ser Ser Ile Ile Met Ala Trp
145                 150                 155                 160
Phe Arg Gln Ala Pro Gly Lys Glu Arg Glu Phe Val Gly Ala Val Ser
                165                 170                 175
Trp Ser Gly Gly Thr Thr Val Tyr Ala Asp Ser Val Leu Gly Arg Phe
                180                 185                 190
Glu Ile Ser Arg Asp Ser Ala Arg Lys Ser Val Tyr Leu Gln Met Asn
                195                 200                 205
Ser Leu Lys Pro Glu Asp Thr Ala Val Tyr Tyr Cys Ala Ala Arg Pro
210                 215                 220
Tyr Gln Lys Tyr Asn Trp Ala Ser Ala Ser Tyr Asn Val Trp Gly Gln
225                 230                 235                 240
Gly Thr Gln Val Thr Val Ser Ser
                245

<210> SEQ ID NO 78
<211> LENGTH: 246
<212> TYPE: PRT
<213> ORGANISM: Lama glama

<400> SEQUENCE: 78

Gln Val Gln Leu Gln Glu Ser Gly Gly Gly Leu Val Gln Pro Gly Gly
1               5                   10                  15
Ser Leu Arg Leu Ser Cys Ala Ala Ser Gly Phe Glu Phe Glu Asn His
                20                  25                  30
Trp Met Tyr Trp Val Arg Gln Ala Pro Gly Lys Gly Leu Glu Trp Val
                35                  40                  45
Ser Thr Val Asn Thr Asn Gly Leu Ile Thr Arg Tyr Ala Asp Ser Val
            50                  55                  60
Lys Gly Arg Phe Thr Ile Ser Arg Asp Asn Ala Lys Tyr Thr Leu Tyr
65                  70                  75                  80
Leu Gln Met Asn Ser Leu Lys Ser Glu Asp Thr Ala Val Tyr Tyr Cys
                85                  90                  95
Thr Lys Val Leu Pro Pro Tyr Ser Asp Asp Ser Arg Thr Asn Ala Asp
                100                 105                 110
Trp Gly Gln Gly Thr Gln Val Thr Val Ser Ser Gln Val Gln Leu Gln
            115                 120                 125
Glu Ser Gly Gly Gly Leu Val Gln Pro Gly Gly Ser Leu Arg Leu Ser
        130                 135                 140
Cys Ala Ala Ser Gly Phe Glu Phe Glu Asn His Trp Met Tyr Trp Val
145                 150                 155                 160
Arg Gln Ala Pro Gly Lys Gly Leu Glu Trp Val Ser Thr Val Asn Thr
                165                 170                 175
Asn Gly Leu Ile Thr Arg Tyr Ala Asp Ser Val Lys Gly Arg Phe Thr
                180                 185                 190
Ile Ser Arg Asp Asn Ala Lys Tyr Thr Leu Tyr Leu Gln Met Asn Ser
                195                 200                 205
Leu Lys Ser Glu Asp Thr Ala Val Tyr Tyr Cys Thr Lys Val Leu Pro
210                 215                 220
Pro Tyr Ser Asp Asp Ser Arg Thr Asn Ala Asp Trp Gly Gln Gly Thr
225                 230                 235                 240
Gln Val Thr Val Ser Ser
                245
```

```
<210> SEQ ID NO 79
<211> LENGTH: 124
<212> TYPE: PRT
<213> ORGANISM: Lama glama

<400> SEQUENCE: 79

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Ser Tyr
            20                  25                  30

Ile Thr Gly Trp Phe Arg Gln Ala Pro Gly Lys Glu Arg Glu Phe Val
        35                  40                  45

Gly Ala Val Ser Trp Ser Ser Thr Ile Val Tyr Ala Asp Ser Val
    50                  55                  60

Glu Gly Arg Phe Thr Ile Ser Arg Asp Asn His Gln Asn Thr Val Tyr
65                  70                  75                  80

Leu Gln Met Asp Ser Leu Lys Pro Glu Asp Thr Ala Val Tyr Tyr Cys
                85                  90                  95

Ala Ala Arg Pro Tyr Gln Lys Tyr Asn Trp Ala Ser Ala Ser Tyr Asn
            100                 105                 110

Val Trp Gly Gln Gly Thr Gln Val Thr Val Ser Ser
            115                 120

<210> SEQ ID NO 80
<211> LENGTH: 123
<212> TYPE: PRT
<213> ORGANISM: Lama glama

<400> SEQUENCE: 80

Gln Val Gln Leu Gln Asp Ser Gly Gly Gly Leu Val Gln Ala Gly Gly
1               5                   10                  15

Ser Leu Arg Leu Ser Cys Gly Val Ser Gly Leu Ser Phe Ser Gly Tyr
            20                  25                  30

Thr Met Gly Trp Phe Arg Gln Ala Pro Gly Lys Glu Arg Glu Phe Ala
        35                  40                  45

Ala Ala Ile Gly Trp Asn Ser Gly Thr Thr Glu Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Pro Lys Tyr Met Thr Ala Tyr Glu Arg Ser Tyr Asp Phe
            100                 105                 110

Trp Gly Gln Gly Thr Gln Val Thr Val Ser Ser
        115                 120

<210> SEQ ID NO 81
<211> LENGTH: 115
<212> TYPE: PRT
<213> ORGANISM: Lama glama

<400> SEQUENCE: 81

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Gly Asp Ser
            20                  25                  30
```

Trp Met Tyr Trp Val Arg Gln Ala Pro Gly Lys Gly Leu Glu Trp Val
              35                  40                  45

Ser Glu Ile Asn Thr Asn Gly Leu Ile Thr Lys Tyr Lys Asp Ser Val
 50                  55                  60

Thr Gly Arg Phe Thr Ile Ser Arg Asp Asn Ala Lys Asn Thr Leu His
 65                  70                  75                  80

Leu Glu Met Asn Arg Leu Lys Pro Glu Asp Thr Ala Leu Tyr Tyr Cys
                 85                  90                  95

Ala Arg Asp Pro Ser Gly Lys Leu Arg Gly Pro Gly Thr Gln Val Thr
                100                 105                 110

Val Ser Ser
        115

<210> SEQ ID NO 82
<211> LENGTH: 115
<212> TYPE: PRT
<213> ORGANISM: Lama glama

<400> SEQUENCE: 82

Gln Val Gln Leu Val Glu Ser Gly Gly Gly Leu Val Gln Pro Gly Gly
 1               5                  10                  15

Pro Leu Arg Leu Ser Cys Ala Ala Ser Gly Phe Ala Phe Gly Asp Ser
                 20                  25                  30

Trp Met Tyr Trp Val Arg Gln Ala Pro Gly Lys Gly Leu Glu Trp Val
              35                  40                  45

Ser Glu Ile Asn Thr Asn Gly Leu Ile Thr Lys Tyr Lys Asp Ser Val
 50                  55                  60

Thr Gly Arg Phe Thr Ile Ser Arg Asp Asn Ala Lys Asn Thr Leu His
 65                  70                  75                  80

Leu Glu Met Asn Arg Leu Lys Pro Glu Asp Thr Ala Leu Tyr Tyr Cys
                 85                  90                  95

Ala Arg Asp Pro Ser Gly Lys Leu Arg Gly Pro Gly Thr Gln Val Thr
                100                 105                 110

Val Ser Ser
        115

<210> SEQ ID NO 83
<211> LENGTH: 115
<212> TYPE: PRT
<213> ORGANISM: Lama glama

<400> SEQUENCE: 83

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Gly Asp Ser
                 20                  25                  30

Trp Met Tyr Trp Val Arg Gln Ala Pro Gly Lys Gly Leu Glu Trp Val
              35                  40                  45

Ser Glu Ile Asn Thr Asn Gly Leu Ile Thr Lys Tyr Lys Asp Ser Val
 50                  55                  60

Thr Gly Arg Phe Thr Ile Ser Arg Asp Asn Ala Lys Asn Thr Leu His
 65                  70                  75                  80

Leu Glu Met Asn Arg Leu Lys Pro Glu Asp Thr Ala Leu Tyr Tyr Cys
                 85                  90                  95

Ala Arg Asp Pro Ser Gly Lys Leu Arg Gly Pro Gly Thr Gln Val Thr
                100                 105                 110

```
Val Ser Ser
        115

<210> SEQ ID NO 84
<211> LENGTH: 115
<212> TYPE: PRT
<213> ORGANISM: Lama glama

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Tyr Trp Val Arg Gln Ala Pro Gly Lys Gly Leu Glu Trp Val
        35                  40                  45

Ser Thr Ile Asn Thr Asn Gly Leu Ile Thr Asn Tyr Ile His Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Leu Asn Gln Ala Gly Leu Ser Arg Gly Gln Gly Thr Gln Val Thr
            100                 105                 110

Val Ser Ser
        115

<210> SEQ ID NO 85
<211> LENGTH: 128
<212> TYPE: PRT
<213> ORGANISM: Lama glama

<400> SEQUENCE: 85

Ala Val Gln Leu Val Glu Ser Gly Gly Gly Leu Val Gln Ala Gly Asp
1               5                   10                  15

Ser Leu Arg Leu Ser Cys Val Val Ser Gly Thr Thr Phe Ser Ser Ala
            20                  25                  30

Ala Met Gly Trp Phe Arg Gln Ala Pro Gly Lys Glu Arg Glu Phe Val
        35                  40                  45

Gly Ala Ile Lys Trp Ser Gly Thr Ser Thr Tyr Tyr Thr Asp Ser Val
    50                  55                  60

Lys Gly Arg Phe Thr Ile Ser Arg Asp Asn Val Lys Asn Thr Val Tyr
65                  70                  75                  80

Leu Gln Met Asn Asn Leu Lys Pro Glu Asp Thr Gly Val Tyr Thr Cys
                85                  90                  95

Ala Ala Asp Arg Asp Arg Tyr Arg Asp Arg Met Gly Pro Met Thr Thr
            100                 105                 110

Thr Asp Phe Arg Phe Trp Gly Gln Gly Thr Gln Val Thr Val Ser Ser
        115                 120                 125

<210> SEQ ID NO 86
<211> LENGTH: 124
<212> TYPE: PRT
<213> ORGANISM: Lama glama

<400> SEQUENCE: 86

Gln Val Lys Leu Glu Glu Ser Gly Gly Gly Leu Val Gln Thr Gly Gly
1               5                   10                  15

Ser Leu Arg Leu Ser Cys Ala Ala Ser Gly Arg Thr Phe Ser Ser Phe
```

```
            20                  25                  30
Ala Met Gly Trp Phe Arg Gln Ala Pro Gly Arg Glu Arg Glu Phe Val
            35                  40                  45

Ala Ser Ile Gly Ser Ser Gly Ile Thr Thr Asn Tyr Ala Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Gly Leu Cys Tyr Cys
                85                  90                  95

Ala Val Asn Arg Tyr Gly Ile Pro Tyr Arg Ser Gly Thr Gln Tyr Gln
                100                 105                 110

Asn Trp Gly Gln Gly Thr Gln Val Thr Val Ser Ser
            115                 120

<210> SEQ ID NO 87
<211> LENGTH: 120
<212> TYPE: PRT
<213> ORGANISM: Lama glama

<400> SEQUENCE: 87

Glu Val Gln Leu Glu Glu Ser Gly Gly Gly Leu Val Gln Pro Gly Gly
  1               5                  10                  15

Ser Leu Arg Leu Ser Cys Ala Ala Ser Gly Leu Thr Phe Asn Asp Tyr
            20                  25                  30

Ala Met Gly Trp Tyr Arg Gln Ala Pro Gly Lys Glu Arg Asp Met Val
            35                  40                  45

Ala Thr Ile Ser Ile Gly Gly Arg Thr Tyr Tyr Ala Asp Ser Val Lys
            50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Ile Tyr Tyr Cys Val
                85                  90                  95

Ala His Arg Gln Thr Val Val Arg Gly Pro Tyr Leu Leu Trp Gly Gln
                100                 105                 110

Gly Thr Gln Val Thr Val Ser Ser
            115                 120

<210> SEQ ID NO 88
<211> LENGTH: 123
<212> TYPE: PRT
<213> ORGANISM: Lama glama

<400> SEQUENCE: 88

Gln Val Gln Leu Val Glu Ser Gly Gly Gly Lys Leu Val Gln Ala Gly
  1               5                  10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
            35                  40                  45

Ala Gly Ser Gly Arg Ser Asn Ser Tyr Asn Tyr Tyr Ser Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Ser Thr Asn Leu Trp Pro Arg Asp Arg Asn Leu Tyr Ala Tyr
```

```
                100             105             110
Trp Gly Gln Gly Thr Gln Val Thr Val Ser Ser
        115                 120

<210> SEQ ID NO 89
<211> LENGTH: 125
<212> TYPE: PRT
<213> ORGANISM: Lama glama

<400> SEQUENCE: 89

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ser Leu Gly Ile Tyr
            20                  25                  30

Arg Met Gly Trp Phe Arg Gln Val Pro Gly Lys Glu Arg Glu Phe Val
        35                  40                  45

Ala Ala Ile Ser Trp Ser Gly Gly Thr Thr Arg Tyr Leu Asp Ser Val
    50                  55                  60

Lys Gly Arg Phe Thr Ile Ser Arg Asp Ser Thr Lys Asn Ala Val Tyr
65                  70                  75                  80

Leu Gln Met Asn Ser Leu Lys Pro Glu Asp Thr Ala Val Tyr Tyr Cys
                85                  90                  95

Ala Val Asp Ser Ser Gly Arg Leu Tyr Trp Thr Leu Ser Thr Ser Tyr
            100                 105                 110

Asp Tyr Trp Gly Gln Gly Thr Gln Val Thr Val Ser Ser
        115                 120                 125

<210> SEQ ID NO 90
<211> LENGTH: 125
<212> TYPE: PRT
<213> ORGANISM: Lama glama

<400> SEQUENCE: 90

Gln Val Gln Leu Val Glu Phe Gly Gly Gly Leu Val Gln Ala Gly Asp
1               5                   10                  15

Ser Leu Arg Leu Ser Cys Ala Ala Ser Gly Arg Ser Leu Gly Ile Tyr
            20                  25                  30

Lys Met Ala Trp Phe Arg Gln Val Pro Gly Lys Glu Arg Glu Phe Val
        35                  40                  45

Ala Ala Ile Ser Trp Ser Gly Gly Thr Thr Arg Tyr Ile Asp Ser Val
    50                  55                  60

Lys Gly Arg Phe Thr Leu Ser Arg Asp Asn Thr Lys Asn Met Val Tyr
65                  70                  75                  80

Leu Gln Met Asn Ser Leu Lys Pro Asp Asp Thr Ala Val Tyr Tyr Cys
                85                  90                  95

Ala Val Asp Ser Ser Gly Arg Leu Tyr Trp Thr Leu Ser Thr Ser Tyr
            100                 105                 110

Asp Tyr Trp Gly Gln Gly Thr Gln Val Thr Val Ser Ser
        115                 120                 125

<210> SEQ ID NO 91
<211> LENGTH: 124
<212> TYPE: PRT
<213> ORGANISM: Lama glama

<400> SEQUENCE: 91

Glu Val Gln Leu Val Glu Ser Gly Gly Gly Leu Val Gln Ala Gly Gly
1               5                   10                  15
```

```
Ser Leu Ser Leu Ser Cys Ala Ala Ser Gly Arg Thr Phe Ser Pro Tyr
            20                  25                  30

Thr Met Gly Trp Phe Arg Gln Ala Pro Gly Lys Glu Arg Glu Phe Leu
            35                  40                  45

Ala Gly Val Thr Trp Ser Gly Ser Thr Phe Tyr Gly Asp Ser Val
 50                  55                  60

Lys Gly Arg Phe Thr Ala Ser Arg Asp Ser Ala Lys Asn Thr Val Thr
 65                  70                  75                  80

Leu Glu Met Asn Ser Leu Asn Pro Glu Asp Thr Ala Val Tyr Tyr Cys
                85                  90                  95

Ala Ala Ala Tyr Gly Gly Gly Leu Tyr Arg Asp Pro Arg Ser Tyr Asp
                100                 105                 110

Tyr Trp Gly Arg Gly Thr Gln Val Thr Val Ser Ser
            115                 120
```

<210> SEQ ID NO 92
<211> LENGTH: 131
<212> TYPE: PRT
<213> ORGANISM: Lama glama

<400> SEQUENCE: 92

```
Ala Val Gln Leu Val Glu Ser Gly Gly Gly Leu Val Gln Ala Gly Gly
 1               5                   10                  15

Ser Leu Arg Leu Ser Cys Ala Ala Ser Gly Phe Thr Leu Asp Ala Trp
            20                  25                  30

Pro Ile Ala Trp Phe Arg Gln Ala Pro Gly Lys Glu Arg Glu Gly Val
            35                  40                  45

Ser Cys Ile Arg Asp Gly Thr Thr Tyr Tyr Ala Asp Ser Val Lys Gly
 50                  55                  60

Arg Phe Thr Ile Ser Ser Asp Asn Ala Asn Asn Thr Val Tyr Leu Gln
 65                  70                  75                  80

Thr Asn Ser Leu Lys Pro Glu Asp Thr Ala Val Tyr Tyr Cys Ala Ala
                85                  90                  95

Pro Ser Gly Pro Ala Thr Gly Ser Ser His Thr Phe Gly Ile Tyr Trp
                100                 105                 110

Asn Leu Arg Asp Asp Tyr Asp Asn Trp Gly Gln Gly Thr Gln Val Thr
            115                 120                 125

Val Ser Ser
    130
```

<210> SEQ ID NO 93
<211> LENGTH: 126
<212> TYPE: PRT
<213> ORGANISM: Lama glama

<400> SEQUENCE: 93

```
Glu Val Gln Leu Val Glu Ser Gly Gly Gly Leu Val Gln Ala Gly Gly
 1               5                   10                  15

Ser Leu Arg Leu Ser Cys Ala Ala Ser Gly Phe Thr Phe Asp His Tyr
            20                  25                  30

Thr Ile Gly Trp Phe Arg Gln Val Pro Gly Lys Glu Arg Glu Gly Val
            35                  40                  45

Ser Cys Ile Ser Ser Ser Asp Gly Ser Thr Tyr Tyr Ala Asp Ser Val
 50                  55                  60

Lys Gly Arg Phe Thr Ile Ser Ser Asp Asn Ala Lys Asn Thr Val Tyr
 65                  70                  75                  80
```

-continued

Leu Gln Met Asn Thr Leu Glu Pro Asp Asp Thr Ala Val Tyr Tyr Cys
                85                  90                  95

Ala Ala Gly Gly Leu Leu Leu Arg Val Glu Leu Gln Ala Ser Asp
            100                 105                 110

Tyr Asp Tyr Trp Gly Gln Gly Ile Gln Val Thr Val Ser Ser
        115                 120                 125

<210> SEQ ID NO 94
<211> LENGTH: 128
<212> TYPE: PRT
<213> ORGANISM: Lama glama

<400> SEQUENCE: 94

Ala Val Gln Leu Val Asp Ser Gly Gly Gly Leu Val Gln Pro Gly Gly
1               5                   10                  15

Ser Leu Arg Leu Ser Cys Thr Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ala Cys Ile Ser Asn Ser Asp Gly Ser Thr Tyr Tyr Gly Asp Ser Val
    50                  55                  60

Lys Gly Arg Phe Thr Ile Ser Arg Asp Asn Ala Lys Thr Thr Val Tyr
65                  70                  75                  80

Leu Gln Met Asn Ser Leu Lys Pro Glu Asp Thr Ala Val Tyr Tyr Cys
                85                  90                  95

Ala Thr Ala Asp Arg His Tyr Ser Ala Ser His His Pro Phe Ala Asp
            100                 105                 110

Phe Ala Phe Asn Ser Trp Gly Gln Gly Thr Gln Val Thr Val Ser Ser
        115                 120                 125

<210> SEQ ID NO 95
<211> LENGTH: 120
<212> TYPE: PRT
<213> ORGANISM: Lama glama

<400> SEQUENCE: 95

Glu Val Gln Leu Val Glu Ser Gly Gly Gly Leu Val Gln Ala Gly Gly
1               5                   10                  15

Ser Leu Arg Leu Ser Cys Ala Ala Tyr Gly Leu Thr Phe Trp Arg Ala
            20                  25                  30

Ala Met Ala Trp Phe Arg Arg Ala Pro Gly Lys Glu Arg Glu Leu Val
        35                  40                  45

Val Ala Arg Asn Trp Gly Asp Gly Ser Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Arg Thr Tyr Gly Ser Ala Thr Tyr Asp Ile Trp Gly Gln
            100                 105                 110

Gly Thr Gln Val Thr Val Ser Ser
        115                 120

<210> SEQ ID NO 96
<211> LENGTH: 123
<212> TYPE: PRT
<213> ORGANISM: Lama glama

<400> SEQUENCE: 96

Glu Val Gln Leu Val Glu Ser Gly Gly Gly Leu Val Gln Asp Gly Gly
1               5                   10                  15

Ser Leu Arg Leu Ser Cys Ile Phe Ser Gly Arg Thr Phe Ala Asn Tyr
            20                  25                  30

Ala Met Gly Trp Phe Arg Gln Ala Pro Gly Lys Glu Arg Glu Phe Val
        35                  40                  45

Ala Ala Ile Asn Arg Asn Gly Thr Thr Asn Tyr Ala Asp Ala Leu
    50                  55                  60

Lys Gly Arg Phe Thr Ile Ser Arg Asp Asn Lys Asn Thr Ala Phe
65                  70                  75                  80

Leu Gln Met Asn Ser Leu Lys Pro Asp Asp Thr Ala Val Tyr Tyr Cys
                85                  90                  95

Ala Ala Arg Glu Trp Pro Phe Ser Thr Ile Pro Ser Gly Trp Arg Tyr
            100                 105                 110

Trp Gly Gln Gly Thr Gln Val Thr Val Ser Ser
        115                 120

<210> SEQ ID NO 97
<211> LENGTH: 125
<212> TYPE: PRT
<213> ORGANISM: Lama glama

<400> SEQUENCE: 97

Asp Val Gln Leu Val Glu Ser Gly Gly Gly Trp Val Gln Pro Gly Gly
1               5                   10                  15

Ser Leu Arg Leu Ser Cys Ala Ala Ser Gly Pro Thr Ala Ser Ser His
            20                  25                  30

Ala Ile Gly Trp Phe Arg Gln Ala Pro Gly Lys Glu Arg Glu Phe Val
        35                  40                  45

Val Gly Ile Asn Arg Gly Gly Val Thr Arg Asp Tyr Ala Asp Ser Val
    50                  55                  60

Lys Gly Arg Phe Ala Val Ser Arg Asp Asn Val Lys Asn Thr Val Tyr
65                  70                  75                  80

Leu Gln Met Asn Arg Leu Lys Pro Glu Asp Ser Ala Ile Tyr Ile Cys
                85                  90                  95

Ala Ala Arg Pro Glu Tyr Ser Phe Thr Ala Met Ser Lys Gly Asp Met
            100                 105                 110

Asp Tyr Trp Gly Lys Gly Thr Leu Val Thr Val Ser Ser
        115                 120                 125

<210> SEQ ID NO 98
<211> LENGTH: 23
<212> TYPE: DNA
<213> ORGANISM: Lama glama

<400> SEQUENCE: 98
gaggtbcarc tgcaggastc ygg                                           23

<210> SEQ ID NO 99
<211> LENGTH: 53
<212> TYPE: DNA
<213> ORGANISM: Lama glama

<400> SEQUENCE: 99
aacagttaag cttccgcttg cggccgcgga gctggggtct tcgctgtggt gcg          53

<210> SEQ ID NO 100
<211> LENGTH: 53
<212> TYPE: DNA
<213> ORGANISM: Lama glama

<400> SEQUENCE: 100
aacagttaag cttccgcttg cggccgctgg ttgtggtttt ggtgtcttgg gtt      53

<210> SEQ ID NO 101
<211> LENGTH: 98
<212> TYPE: PRT
<213> ORGANISM: Homo sapiens

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 102
<211> LENGTH: 123
<212> TYPE: PRT
<213> ORGANISM: Lama glama

<400> SEQUENCE: 102

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Glu Phe Glu Asn His
            20                  25                  30

Trp Met Tyr Trp Val Arg Gln Ala Pro Gly Lys Gly Leu Glu Trp Val
        35                  40                  45

Ser Thr Val Asn Thr Asn Gly Leu Ile Thr Arg Tyr Ala Asp Ser Val
    50                  55                  60

Lys Gly Arg Phe Thr Ile Ser Arg Asp Asn Ala Lys Tyr Thr Leu Tyr
65                  70                  75                  80

Leu Gln Met Asn Ser Leu Lys Ser Glu Asp Thr Ala Val Tyr Tyr Cys
                85                  90                  95

Thr Lys Val Leu Pro Pro Tyr Ser Asp Asp Ser Arg Thr Asn Ala Asp
            100                 105                 110

Trp Gly Gln Gly Thr Gln Val Thr Val Ser Ser
        115                 120

<210> SEQ ID NO 103
<211> LENGTH: 23
<212> TYPE: DNA
<213> ORGANISM: Lama glama

<400> SEQUENCE: 103
cccctggccc cagtagttat acg      23

<210> SEQ ID NO 104
<211> LENGTH: 17
<212> TYPE: DNA
<213> ORGANISM: Lama glama

<400> SEQUENCE: 104
tgtgcagcaa gagacgg                                                     17

<210> SEQ ID NO 105
<211> LENGTH: 44
<212> TYPE: DNA
<213> ORGANISM: Lama glama

<400> SEQUENCE: 105
gtcctcgcaa ctgcggccca gccggcctgt gcagcaagag acgg                        44

<210> SEQ ID NO 106
<211> LENGTH: 45
<212> TYPE: DNA
<213> ORGANISM: Lama glama

<400> SEQUENCE: 106
gtcctcgcaa ctgcgcggcc gccccctggc cccagtagtt atacg                       45

<210> SEQ ID NO 107
<211> LENGTH: 60
<212> TYPE: DNA
<213> ORGANISM: Lama glama

<400> SEQUENCE: 107
agagacaact ccaagaacac gctgtatctg caaatgaaca gcctgagagc tgaggacacg       60

<210> SEQ ID NO 108
<211> LENGTH: 20
<212> TYPE: PRT
<213> ORGANISM: Lama glama

<400> SEQUENCE: 108

Arg Asp Asn Ser Lys Asn Thr Leu Tyr Leu Gln Met Asn Ser Leu Arg
1               5                   10                  15

Ala Glu Asp Thr
            20

<210> SEQ ID NO 109
<211> LENGTH: 30
<212> TYPE: DNA
<213> ORGANISM: Lama glama

<400> SEQUENCE: 109
catggctgag gtgcagctgc tcgagtctgg                                        30

<210> SEQ ID NO 110
<211> LENGTH: 9
<212> TYPE: PRT
<213> ORGANISM: Lama glama

<400> SEQUENCE: 110

Met Ala Glu Val Gln Leu Leu Glu Ser
1               5

<210> SEQ ID NO 111
<211> LENGTH: 35

<212> TYPE: DNA
<213> ORGANISM: Lama glama

<400> SEQUENCE: 111
ggacacggcc gtctattact gtgcaaaagt acttc                35

<210> SEQ ID NO 112
<211> LENGTH: 11
<212> TYPE: PRT
<213> ORGANISM: Lama glama

<400> SEQUENCE: 112

Asp Thr Ala Val Tyr Tyr Cys Ala Lys Val Leu
1               5                   10

<210> SEQ ID NO 113
<211> LENGTH: 30
<212> TYPE: DNA
<213> ORGANISM: Lama glama

<400> SEQUENCE: 113
acctatacca ttggctgggt ccgccaggct                30

<210> SEQ ID NO 114
<211> LENGTH: 10
<212> TYPE: PRT
<213> ORGANISM: Lama glama

<400> SEQUENCE: 114

Thr Tyr Thr Ile Gly Trp Val Arg Gln Ala
1               5                   10

<210> SEQ ID NO 115
<211> LENGTH: 30
<212> TYPE: DNA
<213> ORGANISM: Lama glama

<400> SEQUENCE: 115
cgccaggctc cagggaaggg gcgtgagttt                30

<210> SEQ ID NO 116
<211> LENGTH: 10
<212> TYPE: PRT
<213> ORGANISM: Lama glama

<400> SEQUENCE: 116

Arg Gln Ala Pro Gly Lys Gly Arg Glu Phe
1               5                   10

<210> SEQ ID NO 117
<211> LENGTH: 30
<212> TYPE: DNA
<213> ORGANISM: Lama glama

<400> SEQUENCE: 117
agggaaggag cttgagtttg tagcgcgtat                30

<210> SEQ ID NO 118
<211> LENGTH: 9
<212> TYPE: PRT
<213> ORGANISM: Lama glama

<400> SEQUENCE: 118

Gly Lys Glu Leu Glu Phe Val Ala Arg

```
<210> SEQ ID NO 119
<211> LENGTH: 29
<212> TYPE: DNA
<213> ORGANISM: Lama glama

<400> SEQUENCE: 119
gggaaggagc gtgagtgggt agcgcgtat                                29

<210> SEQ ID NO 120
<211> LENGTH: 9
<212> TYPE: PRT
<213> ORGANISM: Lama glama

<400> SEQUENCE: 120

Gly Lys Glu Arg Glu Trp Val Ala Arg
1               5

<210> SEQ ID NO 121
<211> LENGTH: 136
<212> TYPE: PRT
<213> ORGANISM: Lama glama

<400> SEQUENCE: 121

Gln Val Gln Leu Gln Asp Ser Gly Gly Gly Leu Val Gln Ala Gly Gly
1               5                   10                  15

Ser Leu Arg Leu Ser Cys Ala Val Ser Gly Arg Thr Phe Ser Ala His
            20                  25                  30

Ser Val Tyr Thr Met Gly Trp Phe Arg Gln Ala Pro Gly Lys Glu Arg
        35                  40                  45

Glu Phe Val Ala Arg Ile Tyr Trp Ser Ala Asn Thr Tyr Tyr Ala
    50                  55                  60

Asp Ser Val Lys Gly Arg Phe Thr Ile Ser Arg Asp Asn Ala Lys Asn
65                  70                  75                  80

Thr Val Asp Leu Leu Met Asn Ser Leu Lys Pro Glu Asp Thr Ala Val
                85                  90                  95

Tyr Tyr Cys Ala Ala Arg Asp Gly Ile Pro Thr Ser Arg Thr Val Gly
            100                 105                 110

Ser Tyr Asn Tyr Trp Gly Gln Gly Thr Gln Val Thr Val Ser Ser Glu
        115                 120                 125

Pro Lys Thr Pro Lys Pro Gln Pro
    130                 135

<210> SEQ ID NO 122
<211> LENGTH: 138
<212> TYPE: PRT
<213> ORGANISM: Lama glama

<400> SEQUENCE: 122

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asp His
            20                  25                  30

Ser Gly Tyr Thr Tyr Thr Ile Gly Trp Phe Arg Gln Ala Pro Gly Lys
        35                  40                  45

Glu Arg Glu Phe Val Ala Arg Ile Tyr Trp Ser Ser Gly Asn Thr Tyr
    50                  55                  60

Tyr Ala Asp Ser Val Lys Gly Arg Phe Ala Ile Ser Arg Asp Ile Ala
```

```
              65                  70                  75                  80
Lys Asn Thr Val Asp Leu Thr Met Asn Asn Leu Glu Pro Glu Asp Thr
                    85                  90                  95

Ala Val Tyr Tyr Cys Ala Ala Arg Asp Gly Ile Pro Thr Ser Arg Ser
                100                 105                 110

Val Glu Ser Tyr Asn Tyr Trp Gly Gln Gly Thr Gln Val Thr Val Ser
            115                 120                 125

Ser Glu Pro Lys Thr Pro Lys Pro Gln Pro
        130                 135

<210> SEQ ID NO 123
<211> LENGTH: 124
<212> TYPE: PRT
<213> ORGANISM: Lama glama

<400> SEQUENCE: 123

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Asp Phe Ser Val Ser
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Ile Pro Glu Asp Thr Ala Leu Tyr Tyr Cys
                85                  90                  95

Ala Arg Ser Pro Ser Gly Ser Phe Arg Gly Gln Gly Thr Gln Val Thr
            100                 105                 110

Val Ser Ser Glu Pro Lys Thr Pro Lys Pro Gln Pro
        115                 120

<210> SEQ ID NO 124
<211> LENGTH: 132
<212> TYPE: PRT
<213> ORGANISM: Lama glama

<400> SEQUENCE: 124

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Thr Val Asn Thr Asn Gly Leu Ile Thr Arg Tyr Ala Asp Ser Val
    50                  55                  60

Lys Gly Arg Phe Thr Ile Ser Arg Asp Asn Ala Lys Tyr Thr Leu Tyr
65                  70                  75                  80

Leu Gln Met Asn Ser Leu Lys Ser Glu Asp Thr Ala Val Tyr Tyr Cys
                85                  90                  95

Thr Lys Val Val Pro Pro Tyr Ser Asp Asp Ser Arg Thr Asn Ala Asp
            100                 105                 110

Trp Gly Gln Gly Thr Gln Val Thr Val Ser Ser Glu Pro Lys Thr Pro
        115                 120                 125

Lys Pro Gln Pro
```

```
<210> SEQ ID NO 125
<211> LENGTH: 132
<212> TYPE: PRT
<213> ORGANISM: Lama glama

<400> SEQUENCE: 125

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Glu Phe Glu Asn His
            20                  25                  30

Trp Met Tyr Trp Val Arg Gln Ala Pro Gly Lys Gly Leu Glu Trp Val
         35                  40                  45

Ser Thr Val Asn Thr Asn Gly Leu Ile Thr Arg Tyr Ala Asp Ser Val
 50                  55                  60

Lys Gly Arg Phe Thr Ile Ser Arg Asp Asn Ala Lys Tyr Thr Leu Tyr
 65                  70                  75                  80

Leu Gln Met Asn Ser Leu Lys Ser Glu Asp Thr Ala Val Tyr Tyr Cys
             85                  90                  95

Thr Lys Val Leu Pro Pro Tyr Ser Asp Asp Ser Arg Thr Asn Ala Asp
        100                 105                 110

Trp Gly Gln Gly Thr Gln Val Thr Val Ser Ser Glu Pro Lys Thr Pro
            115                 120                 125

Lys Pro Gln Pro
        130

<210> SEQ ID NO 126
<211> LENGTH: 130
<212> TYPE: PRT
<213> ORGANISM: Lama glama

<400> SEQUENCE: 126

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Ser Ile Phe Arg Val Asn
            20                  25                  30

Ala Met Gly Trp Tyr Arg Gln Val Pro Gly Asn Gln Arg Glu Phe Val
         35                  40                  45

Ala Ile Ile Thr Ser Gly Asp Asn Leu Asn Tyr Ala Asp Ala Val Lys
 50                  55                  60

Gly Arg Phe Thr Ile Ser Thr Asp Asn Val Lys Lys Thr Val Tyr Leu
 65                  70                  75                  80

Gln Met Asn Val Leu Lys Pro Glu Asp Thr Ala Val Tyr Tyr Cys Asn
             85                  90                  95

Ala Ile Leu Gln Thr Ser Arg Trp Ser Ile Pro Ser Asn Tyr Trp Gly
        100                 105                 110

Gln Gly Thr Gln Val Thr Val Ser Ser Glu Pro Lys Thr Pro Lys Pro
            115                 120                 125

Gln Pro
    130

<210> SEQ ID NO 127
<211> LENGTH: 133
<212> TYPE: PRT
<213> ORGANISM: Lama glama

<400> SEQUENCE: 127
```

-continued

Gln Val Gln Leu Gln Asp Ser Gly Gly Gly Leu Val Gln Ala Gly Gly
1               5                   10                  15

Ser Leu Arg Leu Ser Cys Ala Ala Ser Gly Gly Thr Phe Ser Ser Ile
            20                  25                  30

Ile Met Ala Trp Phe Arg Gln Ala Pro Gly Lys Glu Arg Glu Phe Val
        35                  40                  45

Gly Ala Val Ser Trp Ser Gly Gly Thr Thr Val Tyr Ala Asp Ser Val
    50                  55                  60

Leu Gly Arg Phe Glu Ile Ser Arg Asp Ser Ala Arg Lys Ser Val Tyr
65                  70                  75                  80

Leu Gln Met Asn Ser Leu Lys Pro Glu Asp Thr Ala Val Tyr Tyr Cys
                85                  90                  95

Ala Ala Arg Pro Tyr Gln Lys Tyr Asn Trp Ala Ser Ala Ser Tyr Asn
                100                 105                 110

Val Trp Gly Gln Gly Thr Gln Val Thr Val Ser Ser Glu Pro Lys Thr
            115                 120                 125

Pro Lys Pro Gln Pro
        130

<210> SEQ ID NO 128
<211> LENGTH: 132
<212> TYPE: PRT
<213> ORGANISM: Lama glama

<400> SEQUENCE: 128

Gln Val Gln Leu Gln Asp Ser Gly Gly Gly Leu Val Gln Ala Gly Gly
1               5                   10                  15

Ser Leu Arg Leu Ser Cys Gly Val Ser Gly Leu Ser Phe Ser Gly Tyr
            20                  25                  30

Thr Met Gly Trp Phe Arg Gln Ala Pro Gly Lys Glu Arg Glu Phe Ala
        35                  40                  45

Ala Ala Ile Gly Trp Asn Ser Gly Thr Thr Glu Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Pro Lys Tyr Met Thr Ala Tyr Glu Arg Ser Tyr Asp Phe
                100                 105                 110

Trp Gly Gln Gly Thr Gln Val Thr Val Ser Ser Glu Pro Lys Thr Pro
            115                 120                 125

Lys Pro Gln Pro
        130

<210> SEQ ID NO 129
<211> LENGTH: 124
<212> TYPE: PRT
<213> ORGANISM: Lama glama

<400> SEQUENCE: 129

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Ser Tyr
            20                  25                  30

Ile Thr Gly Trp Phe Arg Gln Ala Pro Gly Lys Glu Arg Glu Phe Val
        35                  40                  45

Gly Ala Val Ser Trp Ser Ser Thr Ile Val Tyr Ala Asp Ser Val
            50                  55                  60

Glu Gly Arg Phe Thr Ile Ser Arg Asp Asn His Gln Asn Thr Val Tyr
 65                  70                  75                  80

Leu Gln Met Asp Ser Leu Lys Pro Glu Asp Thr Ala Val Tyr Tyr Cys
                 85                  90                  95

Ala Ala Arg Pro Tyr Gln Lys Tyr Asn Trp Ala Ser Ala Ser Tyr Asn
                100                 105                 110

Val Trp Gly Gln Gly Thr Gln Val Thr Val Ser Ser
            115                 120

<210> SEQ ID NO 130
<211> LENGTH: 124
<212> TYPE: PRT
<213> ORGANISM: Lama glama

<400> SEQUENCE: 130

Gln Val Gln Leu Val Glu Ser Gly Gly Gly Leu Val Gln Ala Gly Gly
 1               5                  10                  15

Ser Leu Arg Leu Ser Cys Ala Ala Ser Glu Gly Thr Leu Ser Gly Tyr
             20                  25                  30

Ile Leu Gly Trp Phe Arg Gln Ala Pro Gly Lys Glu Arg Glu Phe Val
             35                  40                  45

Gly Ala Val Ser Trp Ser Gly Gly Thr Ile Val Tyr Ala Asp Ser Val
            50                  55                  60

Lys Gly Arg Phe Glu Ile Ser Arg Asp Asn Ala Arg Asn Thr Val Tyr
 65                  70                  75                  80

Leu Gln Met Asp Ser Leu Lys Ser Glu Asp Thr Ala Val Tyr Tyr Cys
                 85                  90                  95

Ala Ala Arg Pro Tyr Gln Arg Phe Asn Trp Ala Ser Ala Ser Tyr Asn
                100                 105                 110

Val Trp Gly Arg Gly Thr Gln Val Thr Val Ser Ser
            115                 120

<210> SEQ ID NO 131
<211> LENGTH: 253
<212> TYPE: DNA
<213> ORGANISM: Lama glama

<400> SEQUENCE: 131
aagcttgcat gcaaattcta tttcaaggag acagtcataa tgaaatacct attgcctacg      60
gcagccgctg gattgttatt actcgcggcc cagccggcca tggggcctaa taggcggccg     120
cacaggtgca gctgcaggag tcataatgag ggacccaggt caccgtctcc tcagaacaaa     180
aactcatctc agaagaggat ctgaatgggg ccgcacatca tcatcatcat cattaatgag     240
aattcactgg ccg                                                       253

<210> SEQ ID NO 132
<211> LENGTH: 61
<212> TYPE: PRT
<213> ORGANISM: Lama glama

<400> SEQUENCE: 132

Met Lys Tyr Leu Leu Pro Thr Ala Ala Ala Gly Leu Leu Leu Leu Ala
 1               5                  10                  15

Ala Gln Pro Ala Met Gly Pro Ala Ala Ala Gln Val Gln Leu Gln Glu
             20                  25                  30

```
Ser Gly Thr Gln Val Thr Val Ser Ser Glu Gln Lys Leu Ile Ser Glu
        35                  40                  45

Glu Asp Leu Asn Gly Ala Ala His His His His His His
    50                  55                  60
```

SINGLE DOMAIN ANTIBODIES DIRECTED AGAINST TUMOR NECROSIS FACTOR-ALPHA AND USES THEREFOR

RELATED APPLICATIONS

This application is a continuation of U.S. patent application Ser. No. 12/905,589 filed Oct. 15, 2010, which is a continuation of U.S. patent application Ser. No. 11/804,647 filed May 18, 2007, which is a continuation of U.S. patent application Ser. No. 11/788,832 filed Apr. 20, 2007, which is a continuation of U.S. patent application Ser. No. 11/636,300 filed Dec. 8, 2006, which is a continuation of U.S. patent application Ser. No. 10/534,348 filed May 9, 2005, which is a National Stage of PCT/BE03/00192, filed Nov. 7, 2003, which claims priority to PCT/EP03/06581, filed Jun. 23, 2003 and PCT/EP03/07313, filed Jul. 8, 2003; this application also claims the benefit of U.S. provisional application Ser. No. 60/425,073, filed Nov. 8, 2002 and U.S. provisional application Ser. No. 60/425,063, filed Nov. 8, 2002; all of the applications are incorporated herein by reference.

FIELD OF THE INVENTION

The present invention provides polypeptides comprising one or more single domain antibodies directed towards tumor necrosis factor alpha (TNF-alpha). The present invention further relates to their use in diagnosis and therapy. Such antibodies may have a framework sequence with high homology to the human framework sequences. Compositions comprising antibodies to tumor necrosis factor alpha (TNF-alpha) alone or in combination with other drugs are described.

BACKGROUND TO THE INVENTION

Tumor necrosis factor alpha (TNF-alpha) is believed to play an important role in various disorders, for example in inflammatory disorders such as rheumatoid arthritis, Crohn's disease, ulcerative colitis and multiple sclerosis. Both TNF-alpha and the receptors (CD120a, CD120b) have been studied in great detail. TNF-alpha in its bioactive form is a trimer and the groove formed by neighboring subunits is important for the cytokine-receptor interaction. Several strategies to antagonize the action of the cytokine have been developed and are currently used to treat various disease states.

A TNF-alpha inhibitor which has sufficient specificity and selectivity to TNF-alpha may be an efficient prophylactic or therapeutic pharmaceutical compound for preventing or treating disorders where TNF-alpha has been implicated as causative agent. Methods of treating toxic shock (EP 486526), tumor regression, inhibition of cytotoxicity (U.S. Pat. No. 6,448,380, U.S. Pat. No. 6,451,983, U.S. Pat. No. 6,498,237), autoimmune disease such as RA and Crohn's disease (EP 663836, U.S. Pat. No. 5,672,347, U.S. Pat. No. 5,656,272), graft versus host reaction (U.S. Pat. No. 5,672,347), bacterial meningitis (EP 585705) by means of an antibody to TNF-alpha have been described.

Yet none of the presently available drugs are completely effective for the treatment of autoimmune disease, and most are limited by severe toxicity. In addition, it is extremely difficult and a lengthy process to develop a new chemical entity (NCE) with sufficient potency and selectivity to such target sequence. Antibody-based therapeutics on the other hand have significant potential as drugs because they have exquisite specificity to their target and a low inherent toxicity. In addition, the development time can be reduced considerably when compared to the development of new chemical entities (NCE's). However, conventional antibodies are difficult to raise against multimeric proteins where the receptor-binding domain of the ligand is embedded in a groove, as is the case with TNF-alpha. Heavy chain antibodies described in the invention which are derived from *Camelidae*, are known to have cavity-binding propensity (WO97/49805; Lauwereys et al, EMBO J. 17, 5312, 1998)). Therefore, such heavy chain antibodies are inherently suited to bind to receptor binding domains of such ligands as TNF. In addition, such antibodies are known to be stable over long periods of time, therefore increasing their shelf-life (Perez et al, Biochemistry, 40, 74, 2001). Furthermore, such heavy chain antibody fragments can be produced 'en-masse' in fermentors using cheap expression systems compared to mammalian cell culture fermentation, such as yeast or other microorganisms (EP 0 698 097).

The use of antibodies derived from sources such as mouse, sheep, goat, rabbit etc., and humanised derivatives thereof as a treatment for conditions which require a modulation of inflammation is problematic for several reasons. Traditional antibodies are not stable at room temperature, and have to be refrigerated for preparation and storage, requiring necessary refrigerated laboratory equipment, storage and transport, which contribute towards time and expense. Refrigeration is sometimes not feasible in developing countries. Furthermore, the manufacture or small-scale production of said antibodies is expensive because the mammalian cellular systems necessary for the expression of intact and active antibodies require high levels of support in terms of time and equipment, and yields are very low.

Furthermore the large size of conventional antibodies, would restrict tissue penetration, for example, at the site of inflamed tissue. Furthermore, traditional antibodies have a binding activity which depends upon pH, and hence are unsuitable for use in environments outside the usual physiological pH range such as, for example, in treating gastric bleeding, gastric surgery. Furthermore, traditional antibodies are unstable at low or high pH and hence are not suitable for oral administration. However, it has been demonstrated that *camelidae* antibodies resist harsh conditions, such as extreme pH, denaturing reagents and high temperatures (Dumoulin et al, Protein Science 11, 500, 2002), so making them suitable for delivery by oral administration. Furthermore, traditional antibodies have a binding activity, which depends upon temperature, and hence are unsuitable for use in assays or kits performed at temperatures outside biologically active-temperature ranges (e.g. 37±20° C.).

Polypeptide therapeutics and in particular antibody-based therapeutics have significant potential as drugs because they have exquisite specificity to their target and a low inherent toxicity. However, it is known by the skilled addressee that an antibody which has been obtained for a therapeutically useful target requires additional modification in order to prepare it for human therapy, so as to avoid an unwanted immunological reaction in a human individual upon administration thereto. The modification process is commonly termed "humanisation". It is known by the skilled artisan that antibodies raised in species, other than in humans, require humanisation to render the antibody therapeutically useful in humans ((1) CDR grafting: Protein Design Labs: U.S. Pat. No. 6,180,370, U.S. Pat. No. 5,693,761; Genentech U.S. Pat. No. 6,054,297; Celltech: 460167, EP 626390, U.S. Pat. No. 5,859,205; (2) Veneering: Xoma: U.S. Pat. No. 5,869,619, U.S. Pat. No. 5,766,886, U.S. Pat. No. 5,821,123). There is a need for a method for producing antibodies which avoids the requirement for substantial humanisation, or which completely obviates the need for humanisation. There is a need for a new class of antibodies which have defined framework regions or amino acid residues and which can be administered to a human subject without the requirement for substantial humanisation, or the need for humanisation at all.

Another important drawback of conventional antibodies is that they are complex, large molecules and therefore relatively unstable, and they are sensitive to breakdown by proteases. This means that conventional antibody drugs cannot be administered orally, sublingually, topically, nasally, vaginally, rectally or by inhalation because they are not resistant to the low pH at these sites, the action of proteases at these sites and in the blood and/or because of their large size. They have to be administered by injection (intravenously, subcutaneously, etc.) to overcome some of these problems. Administration by injection requires specialist training in order to use a hypodermic syringe or needle correctly and safely. It further requires sterile equipment, a liquid formulation of the therapeutic polypeptide, vial packing of said polypeptide in a sterile and stable form and, of the subject, a suitable site for entry of the needle. Furthermore, subjects commonly experience physical and psychological stress prior to and upon receiving an injection. Therefore, there is need for a method for the delivery of therapeutic polypeptides which avoids the need for injection which is not only cost/time saving, but which would also be more convenient and more comfortable for the subject.

Single domain antibody-based therapeutics have significant potential as drugs because they have exquisite specificity to their target and a low inherent toxicity. However, improving further their intrinsic and functional affinity can lead to many benefits for a patient such as reduced dose of therapeutic, faster therapy, and reduced side effects.

THE AIMS OF THE PRESENT INVENTION

It is an aim of the present invention is to provide polypeptides comprising one or more single domain antibodies which bind to TNF-alpha, homologues of said polypeptides, functional portions of homologues of said polypeptides. Said polypeptides modify the biological activity of TNF-alpha upon binding. Such polypeptides might bind into the receptor-binding groove of TNF-alpha, or might not bind in the receptor binding groove. Such polypeptides are single domain antibodies.

It is a further aim of the present invention to provide single domain antibodies which may be any of the art, or any future single domain antibodies. Examples include, but are not limited to, heavy chain antibodies, antibodies naturally devoid of light chains, single domain antibodies derived from conventional 4-chain antibodies, engineered antibodies and single domain scaffolds other than those derived from antibodies. According to one aspect of the invention, a single domain antibody as used herein is a naturally occurring single domain antibody known as heavy chain antibody devoid of light chains (WO 9404678). For clarity reasons, this variable domain derived from a heavy chain antibody devoid of light chain will be called VHH or nanobody to distinguish it from the conventional VH of four chain immunoglobulins. Such a VHH molecule can be derived from antibodies raised in *Camelidae* species, for example in camel, llama, dromedary, alpaca and guanaco.

It is a further aim of the invention to provide a method of administering anti-TNF-alpha polypeptides intravenously, subcutaneously, orally, sublingually, topically, nasally, vaginally, rectally or by inhalation.

It is a further aim of the invention to enhance the binding affinity of monovalent single domain antibodies.

SUMMARY OF THE INVENTION

One embodiment of the present invention is an anti-TNF-alpha polypeptide comprising at least one anti-TNF-alpha single domain antibody.

Another embodiment of the present invention is an anti-TNF-alpha polypeptide as described above wherein a single domain antibody corresponds to a sequence represented by any of SEQ ID NOs: 1 to 16 and 79 to 84.

Another embodiment of the present invention is an anti-TNF-alpha polypeptide as described above further comprising at least one single domain antibody directed against a serum protein.

Another embodiment of the present invention is an anti-TNF-alpha polypeptide as described above wherein said serum protein is any of serum albumin, serum immunoglobulins, thyroxine-binding protein, transferring, or fibrinogen.

Another embodiment of the present invention is an anti-TNF-alpha polypeptide as described above wherein a single domain anti-serum protein single domain antibody correspond to a sequence represented by any of SEQ ID NOs: 26 to 29 and 85 to 97.

Another embodiment of the present invention is an anti-TNF-alpha polypeptide as described above corresponding to a sequence represented by any of SEQ ID NOs: 30 to 43.

Another embodiment of the present invention is an anti-TNF-alpha polypeptide as described above further comprising at least one single domain antibody selected from the group consisting of anti-IFN-gamma single domain antibody, anti-TNF-alpha receptor single domain antibody and anti-IFN-gamma receptor single domain antibody.

Another embodiment of the present invention is an anti-TNF-alpha polypeptide as described above, wherein the number of single domain antibodies directed against TNF-alpha is at least two.

Another embodiment of the present invention is an anti-TNF-alpha polypeptide as described above corresponding to a sequence represented by any of SEQ ID NOs: 73 to 76.

Another embodiment of the present invention is an anti-TNF-alpha polypeptide as described above, wherein at least one single domain antibody is a humanized *Camelidae* VHHs.

Another embodiment of the present invention is an anti-TNF-alpha polypeptide as described above wherein a humanized *Camelidae* VHH corresponds to a sequence represented by any of SEQ ID NOs: 17 to 19 and 21 to 24.

Another embodiment of the present invention is a composition comprising an anti-TNF-alpha polypeptide as described above and at least one single domain antibody from the group consisting of anti-IFN-gamma single domain antibody, anti-TNF-alpha receptor single domain antibody and anti-IFN-gamma receptor single domain antibody, for simultaneous, separate or sequential administration to a subject.

Another embodiment of the present invention is an anti-TNF-alpha polypeptide as described above, or a composition as described above wherein at least one anti-IFN-gamma single domain antibody correspond to a sequence represented by any of SEQ ID NOs: 44 to 72.

Another embodiment of the present invention is an anti-TNF-alpha polypeptide as described above, or a composition as described above, wherein said single domain antibody is an homologous sequence, a functional portion, or a functional portion of an homologous sequence of the full length single domain antibody.

Another embodiment of the present invention is an anti-TNF-alpha polypeptide as described above, or a composition as described above, wherein the anti-TNF-alpha polypeptide is an homologous sequence, a functional portion, or a functional portion of an homologous sequence of the full length anti-TNF-alpha polypeptide.

Another embodiment of the present invention is an anti-TNF-alpha polypeptide as described above, or a composition as described above wherein at least one single domain antibody is a *Camelidae* VHH.

Another embodiment of the present invention is a nucleic acid encoding an anti-TNF-alpha polypeptide as described above.

Another embodiment of the present invention is a method of identifying an agent that modulates the binding of an anti-TNF-alpha polypeptide as described above, to Tumor Necrosis Factor-alpha comprising the steps of:
(a) contacting an anti-TNF-alpha polypeptide as described above with a target that is Tumor Necrosis Factor alpha, in the presence and absence of a candidate modulator under conditions permitting binding between said polypeptide and target, and
(b) measuring the binding between the polypeptide and target of step (a), wherein a decrease in binding in the presence of said candidate modulator, relative to the binding in the absence of said candidate modulator identified said candidate modulator as an agent that modulates the binding of an anti-TNF-alpha polypeptide as described above and Tumor Necrosis Factor-alpha.

Another embodiment of the present invention is a method of identifying an agent that modulates Tumor Necrosis Factor-alpha-mediated disorders through the binding of an anti-TNF-alpha polypeptide as described above to Tumor Necrosis Factor-alpha comprising:
(a) contacting an anti-TNF-alpha polypeptide as described above with a target that is Tumor Necrosis Factor alpha, in the presence and absence of a candidate modulator under conditions permitting binding between said polypeptide and target, and
(b) measuring the binding between the polypeptide and target of step (a), wherein a decrease in binding in the presence of said candidate modulator, relative to the binding in the absence of said candidate modulator identified, said candidate modulator as an agent that modulates Tumor Necrosis Factor alpha-mediated disorders.

Another embodiment of the present invention is a method of identifying an agent that modulates the binding of Tumor Necrosis Factor alpha to its receptor through the binding of an anti-TNF-alpha polypeptide as described above to Tumor Necrosis Factor-alpha comprising:
(a) contacting an anti-TNF-alpha polypeptide as described above with a target that is Tumor Necrosis Factor-alpha, in the presence and absence of a candidate modulator under conditions permitting binding between said polypeptide and target, and
(b) measuring the binding between the polypeptide and target of step (a), wherein a decrease in binding in the presence of said candidate modulator, relative to the binding in the absence of said candidate modulator identified said candidate modulator as an agent that modulates the binding of Tumor Necrosis Factor-alpha to its receptor.

Another embodiment of the present invention is a kit for screening for agents that modulate Tumor Necrosis Factor-alpha-mediated disorders comprising an anti-TNF-alpha polypeptide as described above and Tumor Necrosis Factor-alpha.

Another embodiment of the present invention is an unknown agent that modulates the binding of an anti-TNF-alpha polypeptide as described above to Tumor Necrosis Factor-alpha, identified according to the method as described above.

Another embodiment of the present invention is an unknown agent that modulates Tumor Necrosis Factor-alpha-mediated disorders, identified according to the methods as described above.

Another embodiment of the present invention is an unknown agent as described above wherein said disorders are one or more of inflammation, rheumatoid arthritis, Crohn's disease, ulcerative colitis, inflammatory bowel syndrome and multiple sclerosis.

Another embodiment of the present invention is an anti-TNF-alpha polypeptide as described above, or a nucleic acid as described above, or a composition as described above, or an agent as described above for treating and/or preventing and/or alleviating disorders relating to inflammatory processes.

Another embodiment of the present invention is a use of an anti-TNF-alpha polypeptide as described above or a nucleic acid as described above, or a composition as described above, or an agent as described above for the preparation of a medicament for treating and/or preventing and/or alleviating disorders relating to inflammatory reactions.

Another embodiment of the present invention is an anti-TNF-alpha polypeptide as described above or a composition as described above, for treating and/or preventing and/or alleviating disorders susceptible to modulation by a TNF-alpha modulating substance which is able pass through the gastric environment without the substance being inactivated.

Another embodiment of the present invention is an use of an anti-TNF-alpha polypeptide as described above or a composition as described above, for the preparation of a medicament for treating, preventing and/or alleviating the symptoms of disorders susceptible to modulation by a TNF-alpha modulating substance which is able pass through the gastric environment without the substance being inactivated.

Another embodiment of the present invention is an anti-TNF-alpha polypeptide as described above or a composition as described above, for treating and/or preventing and/or alleviating disorders susceptible to modulation by a TNF-alpha modulating substance delivered to the vaginal and/or rectal tract.

Another embodiment of the present invention is a use of an anti-TNF-alpha polypeptide as described above or a composition as described above, for the preparation of a medicament for treating, preventing and/or alleviating the symptoms of disorders susceptible to modulation by a TNF-alpha modulating substance delivered to the vaginal and/or rectal tract.

Another embodiment of the present invention is an anti-TNF-alpha polypeptide as described above or a composition as described above, for treating and/or preventing and/or alleviating disorders susceptible to modulation by a TNF-alpha modulating substance delivered to the nose, upper respiratory tract and/or lung.

Another embodiment of the present invention is a use of an anti-TNF-alpha polypeptide as described above or a composition as described above, for the preparation of a medicament for treating, preventing and/or alleviating the symptoms of disorders susceptible to modulation by a TNF-alpha modulating substance delivered to the nose, upper respiratory tract and/or lung.

Another embodiment of the present invention is an anti-TNF-alpha polypeptide as described above or a composition as described above, for treating and/or preventing and/or alleviating disorders susceptible to modulation by a TNF-alpha modulating substance delivered to the intestinal mucosa, wherein said disorder increases the permeability of the intestinal mucosa.

Another embodiment of the present invention is a use of an anti-TNF-alpha polypeptide as described above or a composition as described above, for the preparation of a medicament for treating, preventing and/or alleviating the symptoms of disorders susceptible to modulation by a TNF-alpha modulating substance delivered to the intestinal mucosa, wherein said disorder increases the permeability of the intestinal mucosa.

Another embodiment of the present invention is an anti-TNF-alpha polypeptide as described above or a composition as described above, for treating and/or preventing and/or alleviating disorders susceptible to modulation by a TNF-alpha modulating substance which is able pass through the tissues beneath the tongue effectively.

Another embodiment of the present invention is a use of an anti-TNF-alpha polypeptide as described above or a composition as described above, for the preparation of a medicament for treating, preventing and/or alleviating the symptoms of disorders susceptible to modulation by a TNF-alpha modulating substance which is able pass through the tissues beneath the tongue effectively.

Another embodiment of the present invention is an anti-TNF-alpha polypeptide as described above or a composition as described above, for treating and/or preventing and/or alleviating disorders susceptible to modulation by a TNF-alpha modulating substance which is able pass through the skin effectively.

Another embodiment of the present invention is a use of an anti-TNF-alpha polypeptide as described above or a composition as described above, for the preparation of a medicament for treating, preventing and/or alleviating the symptoms of disorders susceptible to modulation by a TNF-alpha modulating substance which is able pass through the skin effectively.

Another embodiment of the present invention is a method as described above, a kit as described above, a nucleic acid or agent as described above, use of a nucleic acid or agent as described above, a composition as described above, use of a composition as described above, an anti-TNF-alpha polypeptide as described above, use of an anti-TNF-alpha polypeptide as described above wherein said disorders are any of inflammation, rheumatoid arthritis, Crohn's disease, ulcerative colitis, inflammatory bowel syndrome, multiple sclerosis, Addison's disease, Autoimmune hepatitis, Autoimmune parotitis, Diabetes Type I, Epididymitis, Glomerulonephritis, Graves' disease, Guillain-Barre syndrome, Hashimoto's disease, Hemolytic anemia, Systemic lupus erythematosus, Male infertility, Multiple sclerosis, Myasthenia Gravis, Pemphigus, Psoriasis, Rheumatic fever, Rheumatoid arthritis, Sarcoidosis, Scleroderma, Sjogren's syndrome, Spondyloarthropathies, Thyroiditis, and Vasculitis.

Another embodiment of the present invention is a composition comprising a nucleic acid or agent as described above, an anti-TNF-alpha polypeptide as described above, or a composition as described above, and a suitable pharmaceutical vehicle.

Another embodiment of the present invention is a method of diagnosing a disorder characterised by the dysfunction of Tumor Necrosis Factor-alpha comprising:
(a) contacting a sample with an anti-TNF-alpha polypeptide as described above,
(b) detecting binding of said polypeptide to said sample, and
(c) comparing the binding detected in step (b) with a standard, wherein a difference in binding relative to said sample is diagnostic of a disorder characterised by dysfunction of Tumor Necrosis Factor-alpha.

Another embodiment of the present invention is a kit for screening for a disorder as cited above, using a method as described above.

Another embodiment of the present invention is a kit for screening for a disorder as cited above comprising an isolated anti-TNF-alpha polypeptide as described above.

Another embodiment of the present invention is a use of an anti-TNF-alpha polypeptide as described above for the purification of said Tumor Necrosis Factor-alpha.

Another embodiment of the present invention is a use of an anti-TNF-alpha polypeptide as described above for inhibiting the interaction between Tumor Necrosis Factor-alpha and one or more Tumor Necrosis Factor-alpha receptors.

Another embodiment of the present invention is a method for producing an anti-TNF-alpha polypeptide as described above comprising the steps of:
(a) obtaining double stranded DNA encoding a *Camelidae* VHH directed to Tumor Necrosis Factor alpha,
(b) cloning and expressing the DNA selected in step (b).

Another embodiment of the present invention is a method of producing an anti-TNF-alpha polypeptide as described above comprising:
(a) culturing host cells comprising nucleic acid capable of encoding an anti-TNF-alpha polypeptide as described above, under conditions allowing the expression of the polypeptide, and,
(b) recovering the produced polypeptide from the culture.

Another embodiment of the present invention is a method as described above, wherein said host cells are bacterial or yeast.

Another embodiment of the present invention is a kit for screening for any of inflammation, rheumatoid arthritis, Crohn's disease, ulcerative colitis, inflammatory bowel syndrome or multiple sclerosis comprising an anti-TNF-alpha polypeptide as described above.

BRIEF DESCRIPTION OF FIGURES AND TABLES

FIG. 1 Alignment of anti-human TNF VHH's as described in Example 1: VHH#3G (SEQ ID NO:121), VHH#3E (SEQ ID NO:122), VHH#1A (SEQ ID NO:123), VHH#2B (SEQ ID NO:124), VHH#12B (SEQ ID NO:125), VHH#7B (SEQ ID NO:126).

FIG. 2 Dilution series of anti-human TNF-alpha VHHs as tested in ELISA according to Example 1.

Figure 3:
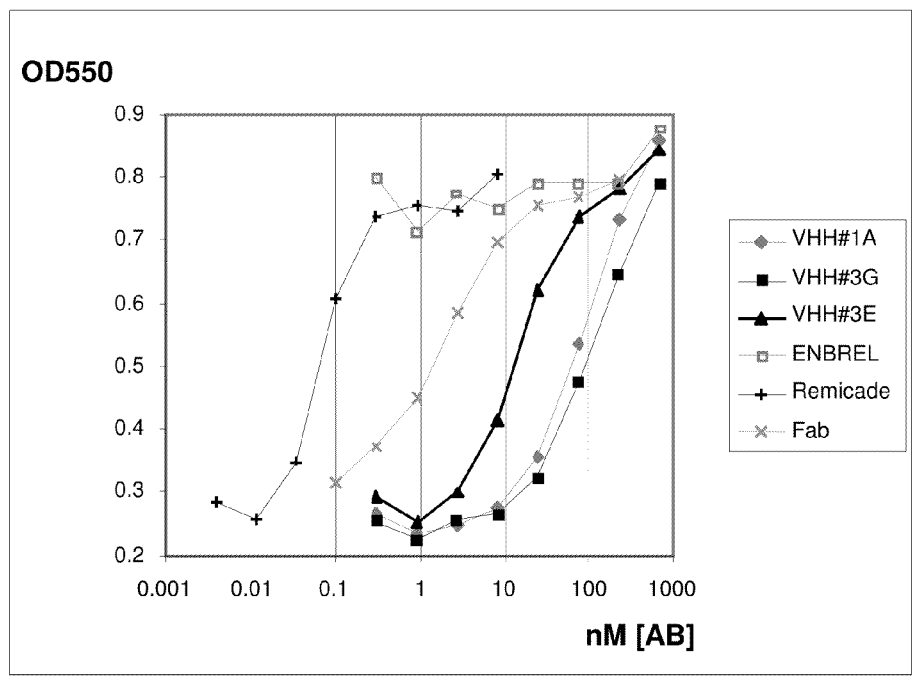

FIG. 3 Antagonistic effect of VHH as determined in cytotoxicity assay using human cell line KYM according to Example 1.

Figure 4:
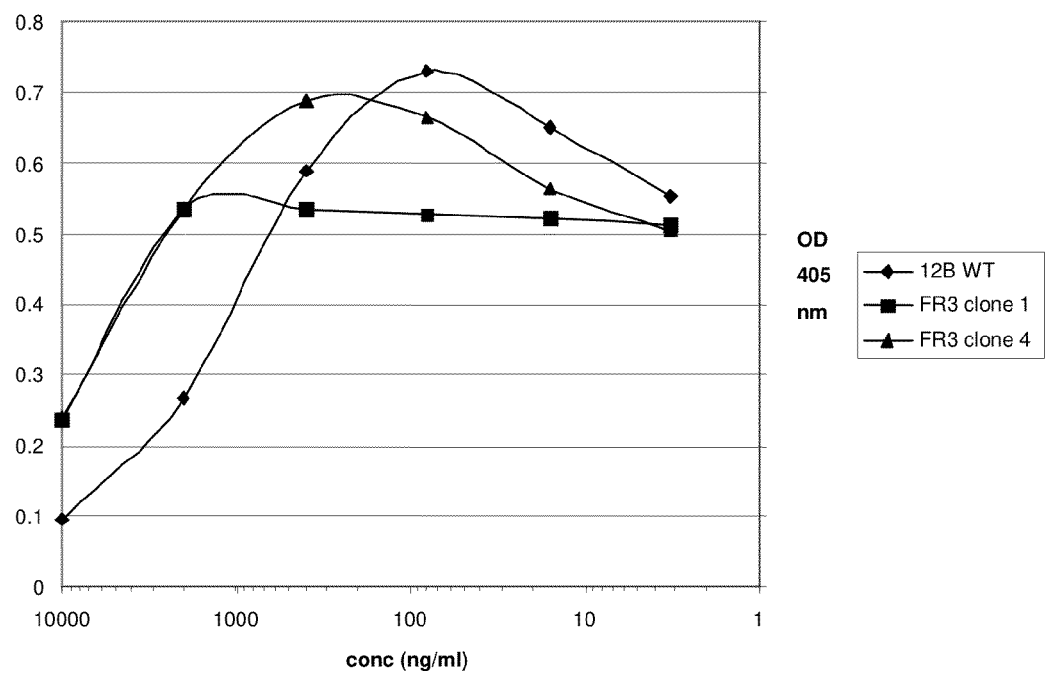

FIG. 4 In vitro receptor binding assay of wild type VHH#12B and mutant A74S+Y76N+K83R+P84A.

Figure 5:
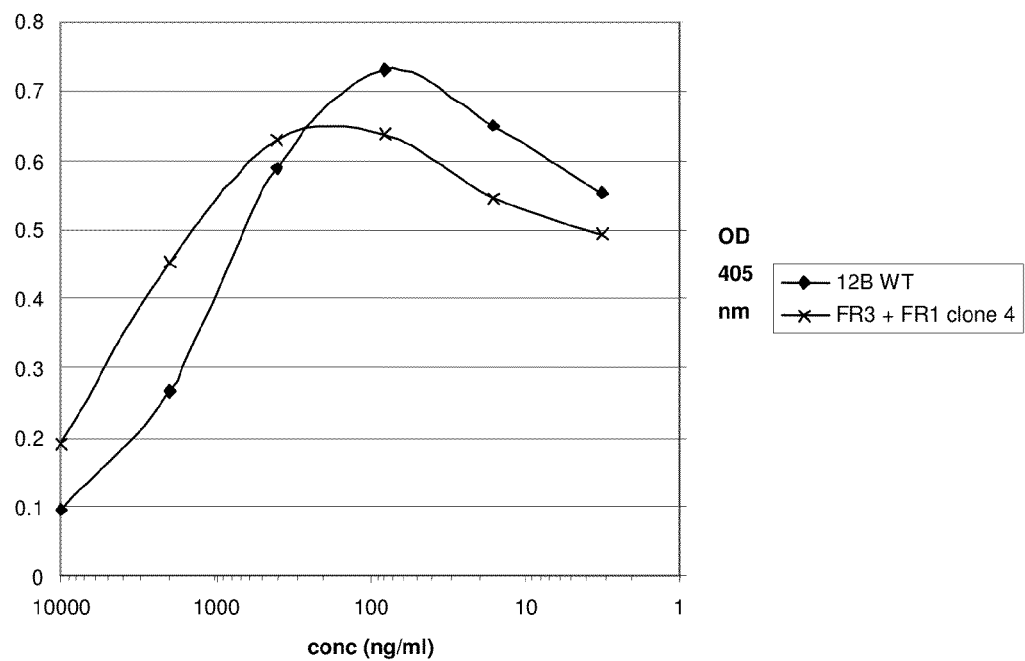

FIG. 5 In vitro receptor binding assay of wild type VHH#12B and mutant 1E+Q5LA74S+Y76N+K83R+P84A.

Figure 6:
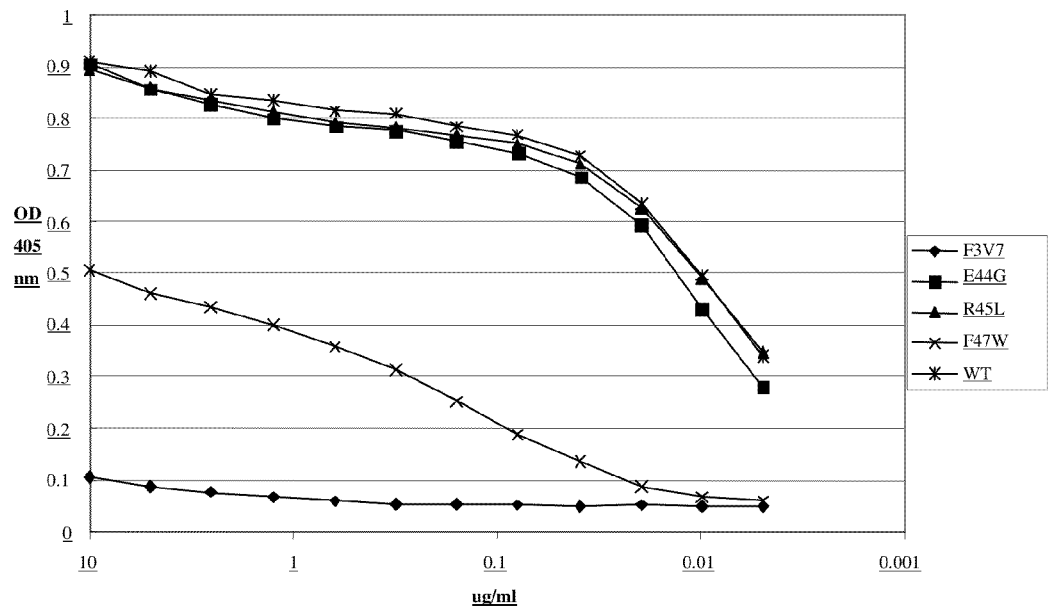

FIG. 6 Binding in ELISA of wild type VHH#3E and mutant VHH's.

Figure 7:
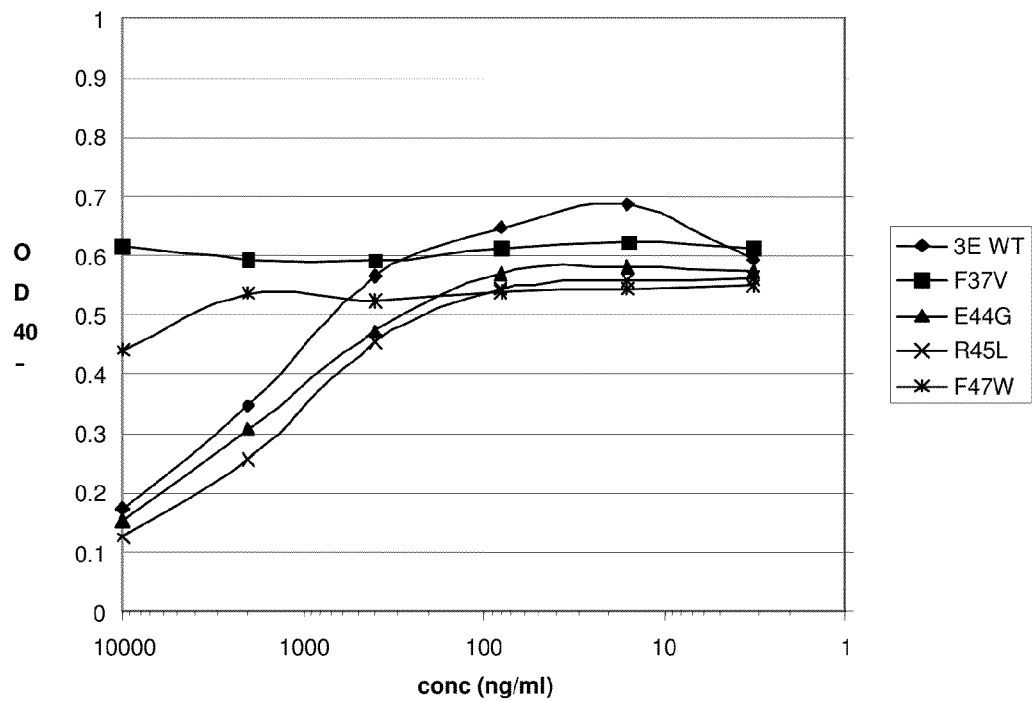

FIG. 7 In vitro receptor binding assay of wild type VHH#3E and mutant VHH's.

FIG. 8 Alignment of antagonistic anti-mouse TNF's as described in Example 3: VHH#m3F (SEQ ID NO:127), VHH#m4B (SEQ ID NO:128), VHH#m9A (SEQ ID NO:129), VHH#m9E (SEQ ID NO:130).

FIG. 9 Antagonistic effect of anti-mouse TNF VHH as determined in cytotoxicity assay using murine cell line L929 according to Example 3.

FIG. 10 EcoRI-HindIII insert (SEQ ID NOs:131, 132) of vector pAX11 (pUC119 backbone) for production of bi-valent or bispecific VHH.

FIG. 11 Coomassie-stained PAGE (15%) of IMAC-purified mono-(lane 8), bi-(lane 1), tri-(lanes 2, 3 and 5) and tetravalent (lanes 4, 6 and 7) anti-TNFα VHH.

Figure 12:
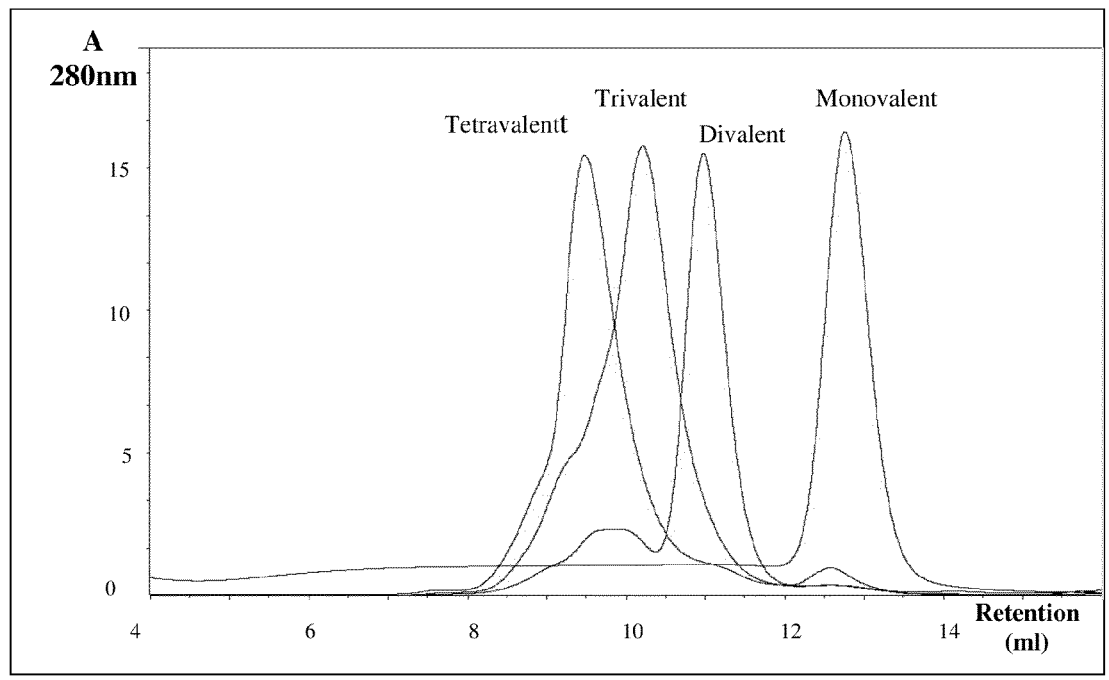

FIG. 12 Chromatogram of the analysis by gel filtration on Superdex 75HR of the mono-, bi-, tri and tetravalent VHH.

Figure 13:
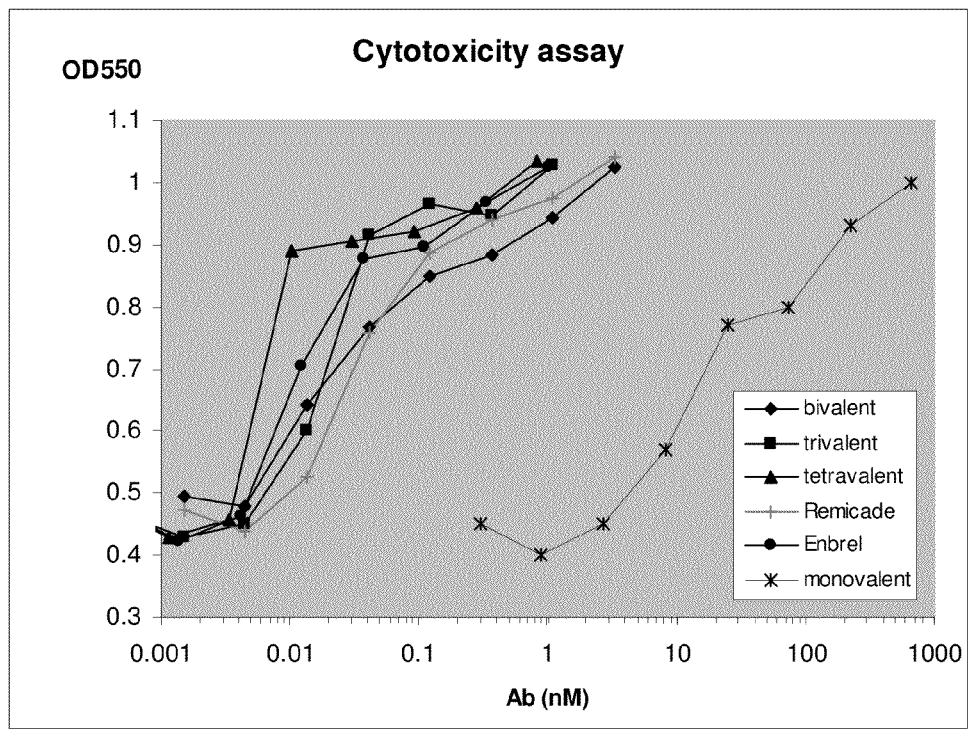

FIG. 13 Comparison of the antagonistic characteristics of the mono-, bi-, tri- and tetravalent form of the anti-human TNF VHH with the clinically used products Remicade and Enbrel.

Figure 14:
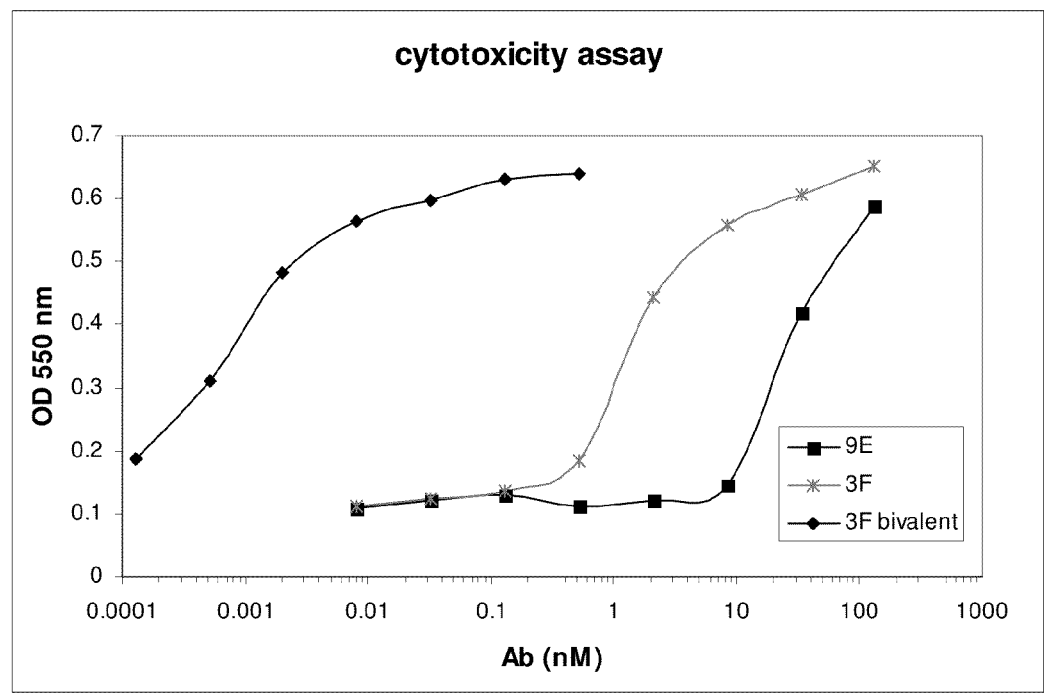

FIG. 14 Antagonistic behaviour of the mono- and bivalent VHH's directed against mouse TNFalpha.

Figure 15:
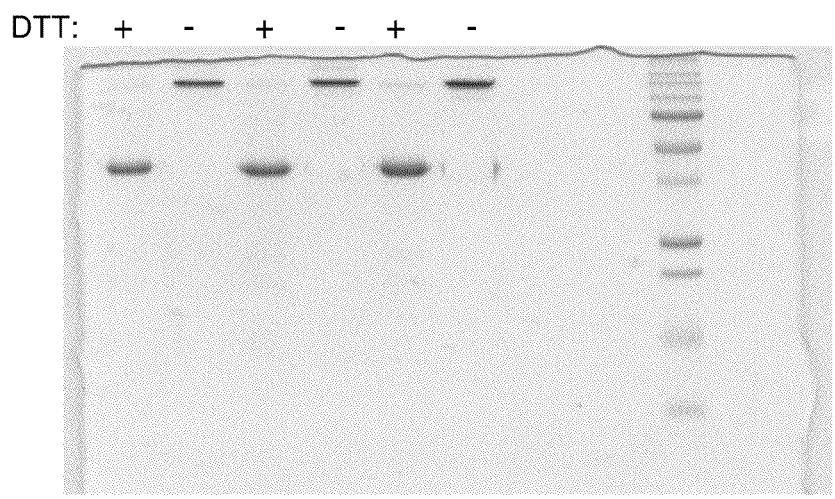

FIG. 15 Coomassie stained PAGE of VHH-Fc-fusion derived from human IgG1 described in Example 4.

Figure 16:
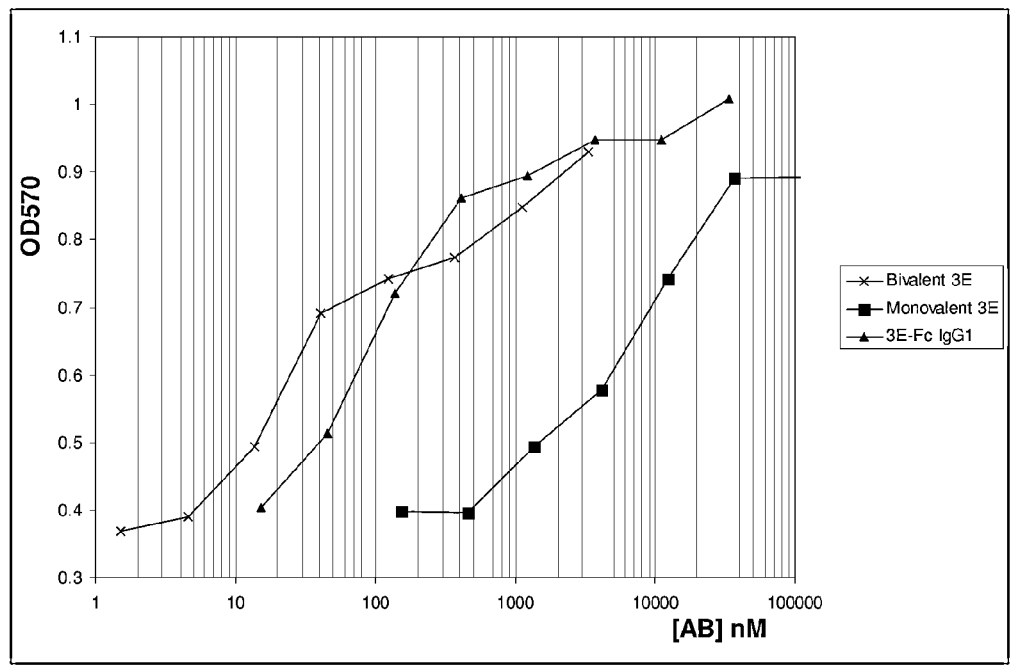

FIG. 16 Antagonistic efficacy of VHH-Fc fusion derived from VHH#3E compared with bivalent format of VHH#3E as determined in bioassay.

Figure 17:
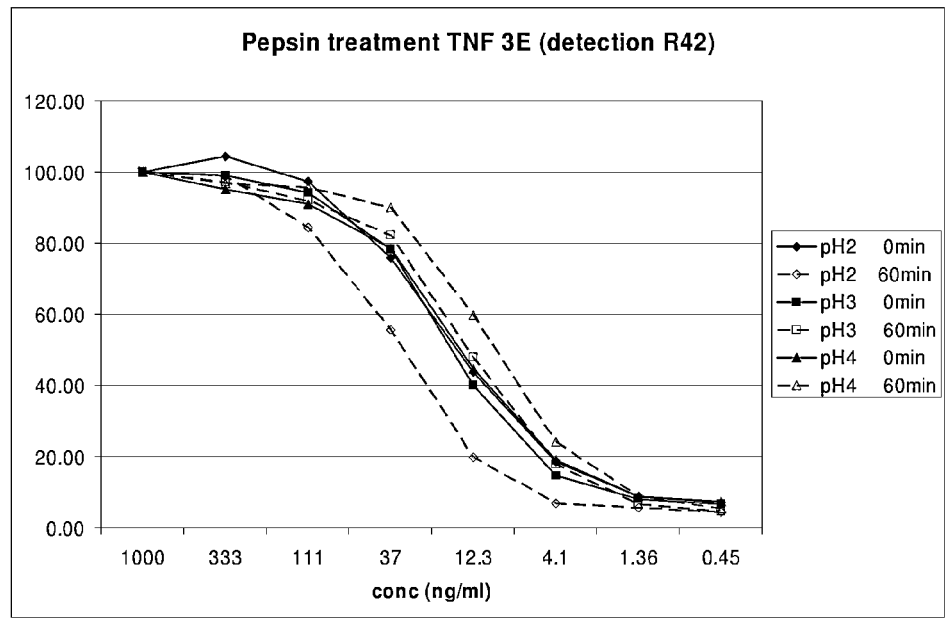

FIG. 17 ELISA of reference and pepsin-treated TNF3E at pH2.2, pH3.2 and pH4.2 (100% is the signal measured at a 1/100 dilution).

Figure 18:
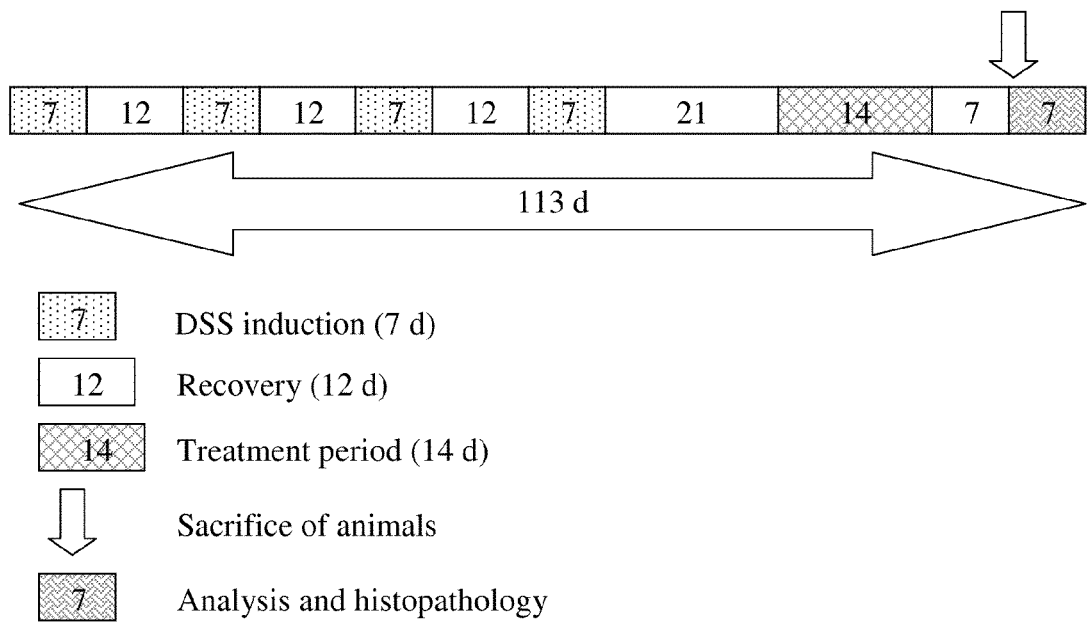

FIG. 18 Experimental setting.

Table 1 Amino acid sequence listing of the peptides of aspects of present invention directed against TNF-alpha.

Table 2 List of mutagenesis reactions, mutagenic primers and templates used for mutagenesis of VHH#12B: mutation A74S+Y76N+K83R+P84A (SEQ ID NOs: 107, 108); mutation Q1E+Q5L+A74S+Y76N+K83R+P84A (SEQ ID NOs: 109, 110); mutation Q1E+Q5L+A74S+Y76N+K83R+P84A+T93A (SEQ ID NOs:111, 112).

Table 3 List of mutagenesis reactions, mutagenic primers and templates used for mutagenesis of VHH#3E: mutation F37V (SEQ ID NOs: 113, 114); mutation E44G (SEQ ID NOs: 115, 116); mutation R45L (SEQ ID NOs: 117, 118); mutation F47W (SEQ ID NOs: 119, 120).

Table 4 Overview of humanised and wild type VHH.

Table 5 Anti-mouse serum albumin/anti TNF-alpha

Table 6 Amino acid sequence listing of VHH's directed against human IFN-gamma.

Table 7 Sequences of bivalent (BIV 3E, BIV#m3F), trivalent (TRI3E) or tetravalent (TETRA 3E) VHH directed against TNF-alpha.

Table 8 Fractional homologies between the amino acid sequences of anti-mouse serum albumin VHHs of the invention.

Table 9 Fractional homologies between anti-TNF-alpha VHHs of the invention.

Table 10 Percentage homologies between anti-IFN-gamma VHHs of the invention.

Table 11 Treatment schedule.

DETAILED DESCRIPTION

The present invention relates to an anti-tumour necrosis factor-alpha (TNF-alpha) polypeptide, comprising one or more single domain antibodies which are directed against TNF-alpha. The invention also relates to nucleic acids capable of encoding said polypeptides.

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibodies as used herein is a naturally occurring single domain antibody known as heavy chain antibody devoid of light chains. Such single domain antibodies are disclosed in WO 94/04678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in *Camelidae* species, for example in camel, dromedary, llama, alpaca and guanaco. Other species besides *Camelidae* may produce heavy chain antibodies naturally devoid of light chain; such VHHs are within the scope of the invention.

VHHs, according to the present invention, and as known to the skilled addressee are heavy chain variable domains derived from immunoglobulins naturally devoid of light chains such as those derived from *Camelidae* as described in WO 94/04678 (and referred to hereinafter as VHH domains or nanobodies). VHH molecules are about 10× smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in *Camelids* will recognize epitopes other than those recognised by antibodies generated in vitro through the use of antibody libraries or via immunisation of mammals other than *Camelids* (WO 9749805). As such, anti-TNF-alpha VHH's may interact more efficiently with TNF-alpha than conventional antibodies, thereby blocking its interaction with the TNF-alpha receptor more efficiently.

According to the invention, TNF-alpha is derived from any species. Examples of species relevant to the invention include as rabbits, goats, mice, rats, cows, calves, camels, llamas, monkeys, donkeys, guinea pigs, chickens, sheep, dogs, cats, horses, and preferably humans.

TNF-alpha is also a fragment of TNF-alpha, capable of eliciting an immune response. TNF-alpha is also a fragment of TNF-alpha, capable of binding to a single domain antibody raised against the full length TNF-alpha.

A single domain antibody directed against TNF-alpha means single domain antibody that it is capable of binding to TNF-alpha with an affinity of better than $10^{-6}$ M.

One embodiment of the present invention is an anti-TNF polypeptide, wherein the single domain antibodies comprise *Camelidae* VHH directed against TNF-alpha.

The one or more single domain antibodies of the anti-TNF polypeptide which are directed against a TNF-alpha may be of the same sequence. Alternatively they may not all have the same sequence. It is within the scope of the invention that an anti-TNF polypeptide comprises anti-TNF-alpha single domain antibodies which do not all share the same sequence, but which are directed against the same target, one or more antigens thereof.

Another embodiment of the present invention is an anti-TNF-alpha polypeptide, wherein a single domain antibody corresponds to a sequence represented by any of SEQ ID NOs: 1 to 16 and 79 to 84 as shown in Table 1. Said sequences are derived from *Camelidae* heavy chain antibodies (VHHs) which are directed against TNF-alpha.

The present invention further relates to an anti-TNF-alpha polypeptide, wherein said single domain antibody is a VHH directed against TNF-alpha, wherein the VHH belongs to a class having human-like sequences. The class is characterised in that the VHHs carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. The new class of *Camelidae* single-domain antibodies described in this invention (Table 1, Example 1) is represented by VHH#2B (SEQ ID NO: 3) and VHH#12B (SEQ ID No. 14) containing the hydrophobic residues in FR2 in combination with the hydrophobic residue tryptophan at position 103.

Another human-like class of *Camelidae* single domain antibodies represented by sequences VHH#1A (SEQ ID NO. 1), VHH#4B (SEQ ID NO. 12), VHH#8-29 (SEQ ID NO. 81), VHH#8-41 (SEQ ID NO. 82), VHH#8-42 (SEQ ID NO. 83) and VHH#8-44 (SEQ ID NO. 84) (Table 1, Example 1) have been described in WO03035694 and contain the hydrophobic FR2 residues typically found in conventional antibodies of human origin or from other species, but compensating this loss in hydrophilicity by the charged arginine residue on position 103 that substitutes the conserved tryptophan residue present in VH from double-chain antibodies. As such, peptides belonging to these two classes show a high amino acid sequence homology to human VH framework regions and said peptides might be administered to a human directly without expectation of an unwanted immune response therefrom, and without the burden of further humanisation. The invention also relates to nucleic acids capable of encoding said polypeptides.

Therefore, one aspect of the present invention allows for the direct administration of an anti-TNF-alpha polypeptide, wherein the single domain antibodies belong to the humanized class of VHH, and comprise a sequence represented by any of SEQ ID NO:1, 3, 12, 14, 81, 82, 83, and 84 to a patient in need of the same.

Any of the VHHs as used by the invention may be of the traditional class or of the classes of human-like *Camelidae* antibodies. Said antibodies may be directed against whole TNF-alpha or a fragment thereof, or a fragment of a homologous sequence thereof. These polypeptides include the full length *Camelidae* antibodies, namely Fc and VHH domains, chimeric versions of heavy chain *Camelidae* antibodies with a human Fc domain or VHH's by themselves or derived fragments.

Anti-serum albumin VHH's may interact in a more efficient way with serum albumin than conventional antibodies which is known to be a carrier protein. As a carrier protein some of the epitopes of serum albumin may be inaccessible by bound proteins, peptides and small chemical compounds. Since VHH's are known to bind into 'unusual' or non-conventional epitopes such as cavities (WO 97/49805), the affinity of such VHH's to circulating albumin may be increased.

The present invention also relates to the finding that an anti-TNF polypeptide as described herein further comprising one or more single domain antibodies directed against one or more serum proteins of a subject, surprisingly has significantly prolonged half-life in the circulation of said subject compared with the half-life of the anti-TNF-alpha single domain antibody when not part of said construct. Examples of such polypeptides are represented in Table 5 by SEQ ID NOs: 30 to 43. Furthermore, the said polypeptides were found to exhibit the same favourable properties of single domain antibodies such as high stability remaining intact in mice, extreme pH resistance, high temperature stability and high target affinity.

Another embodiment of the present invention is an anti-TNF-alpha polypeptide further comprising one or more single domain antibodies directed against one or more serum proteins, said anti-TNF alpha polypeptide comprising a sequence corresponding to any represented by SEQ ID NOs: 30 to 43 (Table 5).

Another embodiment of the present invention is an anti-TNF-alpha polypeptide, wherein an anti-serum protein single domain antibody corresponds to a sequence represented by any of SEQ ID NOs: 26 to 29 and 85 to 97 as shown in Table 5.

The serum protein may be any suitable protein found in the serum of subject. In one aspect of the invention, the serum protein is serum albumin, serum immunoglobulins, thyroxine-binding protein, transferrin, or fibrinogen. Depending on the intended use such as the required half-life for effective treatment and/or compartimentalisation of the target antigen, the VHH-partner can be directed to one of the above serum proteins.

Another aspect of the invention is an anti-TNF-alpha polypeptide as disclosed herein further comprising at least one polypeptide selected from the group consisting of an anti-IFN-gamma polypeptide, an anti-TNF-alpha receptor polypeptide and anti-IFN-gamma receptor polypeptide.

It is an embodiment of the invention that a single domain antibody directed against IFN-gamma corresponds to a sequence represented by any of SEQ ID NOs: 44 to 72 as shown in Table 6.

According to one aspect of the invention, a single domain antibody is directed against TNF-alpha receptor. Said single domain antibody may be a *Camelidae* VHH.

According to one aspect of the invention, a single domain antibody is directed against IFN-gamma receptor. Said single domain antibody may be a *Camelidae* VHH.

Another aspect of the invention is a method of treating an autoimmune disease or condition as cited herein, comprising administering to a patient an effective amount of an anti-TNF-alpha polypeptide further comprising a least one polypeptide selected from the group consisting of anti-IFN-gamma polypeptide, anti-TNF-alpha receptor polypeptide and anti-IFN-gamma receptor polypeptide, such polypeptides joined to each other as described below.

Such multi-specific constructs may have improved potency as inflammatory therapeutic compound over mono-specific constructs.

One aspect of the invention is a composition comprising an anti-TNF-alpha polypeptide as disclosed herein and at least one polypeptide selected from the group consisting of anti-IFN-gamma polypeptide, anti-TNF-alpha receptor polypeptide and anti-IFN-gamma receptor polypeptide, for simultaneous, separate or sequential administration to a subject.

One aspect of the invention is a method for treating autoimmune disease comprising administering to an individual an effective amount of an anti-TNF-alpha polypeptide and a least one polypeptide selected from the group consisting of anti-IFN-gamma polypeptide, anti-TNF-alpha receptor polypeptide and anti-IFN-gamma receptor polypeptide, simultaneously, separately or sequentially.

Another aspect of the invention is a kit containing an anti-TNF-alpha polypeptide and a least one polypeptide selected from the group consisting of anti-IFN-gamma polypeptide, anti-TNF-alpha receptor polypeptide and anti-IFN-gamma receptor polypeptide for simultaneous, separate or sequential administration to a subject. It is an aspect of the invention that the kit may be used according to the invention. It is an aspect of the invention that the kit may be used to treat the diseases as cited herein.

By simultaneous administration means the polypeptides are administered to a subject at the same time. For example, as a mixture of the polypeptides or a composition comprising said polypeptides. Examples include, but are not limited to a solution administered intraveneously, a tablet, liquid, topical cream, etc., wherein each preparation comprises the polypeptides of interest.

By separate administration means the polypeptides are administered to a subject at the same time or substantially the same time. The polypeptides are present in the kit as separate, unmixed preparations. For example, the different polypeptides may be present in the kit as individual tablets. The tablets may be administered to the subject by swallowing both tablets at the same time, or one tablet directly following the other.

By sequential administration means the polypeptides are administered to a subject sequentially. The polypeptides are present in the kit as separate, unmixed preparations. There is a time interval between doses. For example, one polypeptide might be administered up to 336, 312, 288, 264, 240, 216, 192, 168, 144, 120, 96, 72, 48, 24, 20, 16, 12, 8, 4, 2, 1, or 0.5 hours after the other component.

In sequential administration, one polypeptide may be administered once, or any number of times and in various doses before and/or after administration of another polypeptide. Sequential administration may be combined with simultaneous or sequential administration.

The medical uses of the anti-TNF-alpha polypeptide described below, also apply to the composition comprising an anti-TNF-alpha polypeptide as disclosed herein and at least one polypeptide selected from the group consisting of anti-IFN-gamma polypeptide, anti-TNF-alpha receptor polypeptide and anti-IFN-gamma receptor polypeptide, for simultaneous, separate or sequential administration to a subject as disclosed here above.

According to one aspect of the invention, an anti-IFN-gamma polypeptide anti-TNF-alpha a single domain antibody directed against IFN-gamma. Said single domain antibody may be a *Camelidae* VH H.

It is an embodiment of the invention that a single domain antibody directed against IFN-gamma corresponds to a sequence represented by any of SEQ ID NOs: 44 to 72 as shown in Table 6.

According to one aspect of the invention, anti-TNF-alpha a single domain antibody directed against TNF-alpha receptor. Said single domain antibody may be a *Camelidae* VHH.

According to one aspect of the invention, an anti-IFN-gamma receptor polypeptide anti-TNF-alpha a single domain antibody directed against IFN-gamma receptor. Said single domain antibody may be a *Camelidae* VHH.

Another embodiment of the present invention is an anti-TNF-alpha polypeptide as disclosed herein, wherein the number of single domain antibodies directed against TNF-alpha is two or more. Such multivalent anti-TNF-alpha polypeptides have the advantage of unusually high functional affinity for the target, displaying much higher than expected inhibitory properties compared to their monovalent counterparts.

The multivalent anti-TNF-alpha polypeptides have functional affinities that are several orders of magnitude higher than the monovalent parent anti-TNF-alpha polypeptides. The inventors have found that the functional affinities of these multivalent polypeptides are much higher than those reported in the prior art for bivalent and multivalent antibodies. Surprisingly, anti-TNF-alpha polypeptides of the present invention linked to each other directly (SEQ ID No. 77 and 78) or via a short linker sequence show the high functional affinities expected theoretically with multivalent conventional four-chain antibodies.

The inventors have found that such large increased functional activities can be detected preferably with antigens composed of multidomain and multimeric proteins, either in straight binding assays or in functional assays, e.g. cytotoxicity assays.

Another embodiment of the present invention is an anti-TNF-alpha polypeptide as disclosed herein, wherein the number of single domain antibodies directed against TNF-alpha is two or more, said anti-TNF-alpha polypeptide comprising a sequence corresponding to any represented by SEQ ID NOs: 73 to 76.

The single domain antibodies may be joined to form any of the polypeptides disclosed herein comprising more than one single domain antibody using methods known in the art or any future method. For example, they may be fused by chemical cross-linking by reacting amino acid residues with an organic derivatising agent such as described by Blattler et al, Biochemistry 24, 1517-1524; EP294703. Alternatively, the single domain antibody may be fused genetically at the DNA level i.e. a polynucleotide construct formed which encodes the complete polypeptide construct comprising one or more anti-target single domain antibodies and one or more anti-serum protein single domain antibodies. A method for producing bivalent or multivalent VHH polypeptide constructs is disclosed in PCT patent application WO 96/34103. One way of joining multiple single domain antibodies is via the genetic route by linking single domain antibody coding sequences either directly or via a peptide linker. For example, the C-terminal end of the first single domain antibody may be linked to the N-terminal end of the next single domain antibody. This linking mode can be extended in order to link additional single domain antibodies for the construction and production of tri-, tetra-, etc. functional constructs.

According to one aspect of the present invention, the single domain antibodies are linked to each other directly, without use of a linker. Contrary to joining bulky conventional antibodies where a linker sequence is needed to retain binding activity in the two subunits, polypeptides of the invention can be linked directly (SEQ ID No. 77 and 78) thereby avoiding potential problems of the linker sequence, such as antigenicity when administered to a human subject, instability of the linker sequence leading to dissociation of the subunits.

According to another aspect of the present invention, the single domain antibodies are linked to each other via a peptide linker sequence. Such linker sequence may be a naturally occurring sequence or a non-naturally occurring sequence. The linker sequence is expected to be non-immunogenic in the subject to which the anti-TNF-alpha polypeptide is administered. The linker sequence may provide sufficient flexibility to the multivalent anti-TNF-alpha polypeptide, at the same time being resistant to proteolytic degradation. A non-limiting example of a linker sequences is one that can be derived from the hinge region of VHHs described in WO 96/34103.

According to another aspect of the invention, multivalent single domain antibodies comprising more than two single domain antibodies can be linked to each other either directly or via a linker sequence. Such constructs are difficult to produce with conventional antibodies and due to steric hindrance of the bulky subunits, functionality will be lost or greatly diminished rather than increased considerably as seen with VHH's of the invention compared to the monovalent construct (see FIG. 12 for gel filtration analyses of such multivalent VHH constructs).

The polypeptide constructs disclosed herein may be made by the skilled artisan according to methods known in the art or any future method. For example, VHHs may be obtained using methods known in the art such as by immunising a camel and obtaining hybridomas therefrom, or by cloning a library of single domain antibodies using molecular biology techniques known in the art and subsequent selection by using phage display.

According to an aspect of the invention an anti-TNF-alpha polypeptide may be a homologous sequence of a full-length anti-TNF-alpha polypeptide. According to another aspect of the invention, an anti-TNF-alpha polypeptide may be a functional portion of a full-length anti-TNF-alpha polypeptide. According to another aspect of the invention, an anti-TNF-alpha polypeptide may be a homologous sequence of a full-length anti-TNF-alpha polypeptide. According to another aspect of the invention, an anti-TNF-alpha polypeptide may be a functional portion of a homologous sequence of a full-length anti-TNF-alpha polypeptide. According to an aspect of the invention an anti-TNF-alpha polypeptide may comprise a sequence of an anti-TNF-alpha polypeptide.

According to an aspect of the invention a single domain antibody used to form an anti-TNF-alpha polypeptide may be a complete single domain antibody (e.g. a VHH) or a homologous sequence thereof. According to another aspect of the invention, a single domain antibody used to form the polypeptide construct may be a functional portion of a complete single domain antibody. According to another aspect of the invention, a single domain antibody used to form the polypeptide construct may be a homologous sequence of a complete single domain antibody. According to another aspect of the invention, a single domain antibody used to form the polypeptide construct may be a functional portion of a homologous sequence of a complete single domain antibody.

As used herein, an homologous sequence of the present invention may comprise additions, deletions or substitutions of one or more amino acids, which do not substantially alter the functional characteristics of the polypeptides of the invention. The number of amino acid deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A homologous sequence according to the present invention may a polypeptide modified by the addition, deletion or substitution of amino acids, said modification not substantially altering the functional characteristics compared with the unmodified polypeptide.

A homologous sequence according to the present invention may be a polypeptide modified by the addition, deletion or substitution of amino acids, said modification not substantially altering the functional characteristics compared with the unmodified polypeptide.

A homologous sequence according to the present invention may be a sequence which exists in other *Camelidae* species such as, for example, camel, dromedary, llama, alpaca, guanaco etc.

Where homologous sequence indicates sequence identity, it means a sequence which presents a high sequence identity (more than 70%, 75%, 80%, 85%, 90%, 95% or 98% sequence identity) with the parent sequence and is preferably characterised by similar properties of the parent sequence, namely affinity, said identity calculated using known methods.

Alternatively, an homologous sequence may also be any amino acid sequence resulting from allowed substitutions at any number of positions of the parent sequence according to the formula below:
Ser substituted by Ser, Thr, Gly, and Asn;
Arg substituted by one of Arg, His, Gln, Lys, and Glu;
Leu substituted by one of Leu, Ile, Phe, Tyr, Met, and Val;
Pro substituted by one of Pro, Gly, Ala, and Thr;
Thr substituted by one of Thr, Pro, Ser, Ala, Gly, His, and Gln;
Ala substituted by one of Ala, Gly, Thr, and Pro;
Val substituted by one of Val, Met, Tyr, Phe, Ile, and Leu;
Gly substituted by one of Gly, Ala, Thr, Pro, and Ser;
Ile substituted by one of Ile, Met, Tyr, Phe, Val, and Leu;
Phe substituted by one of Phe, Trp, Met, Tyr, Ile, Val, and Leu;
Tyr substituted by one of Tyr, Trp, Met, Phe, Ile, Val, and Leu;
His substituted by one of His, Glu, Lys, Gln, Thr, and Arg;
Gln substituted by one of Gln, Glu, Lys, Asn, His, Thr, and Arg;
Asn substituted by one of Asn, Glu, Asp, Gln, and Ser;
Lys substituted by one of Lys, Glu, Gln, His, and Arg;
Asp substituted by one of Asp, Glu, and Asn;
Glu substituted by one of Glu, Asp, Lys, Asn, Gln, His, and Arg;
Met substituted by one of Met, Phe, Ile, Val, Leu, and Tyr.

A homologous nucleotide sequence according to the present invention may refer to nucleotide sequences of more than 50, 100, 200, 300, 400, 500, 600, 800 or 1000 nucleotides able to hybridize to the reverse-complement of the nucleotide sequence capable of encoding the patent sequence, under stringent hybridisation conditions (such as the ones described by Sambrook et al., Molecular Cloning, Laboratory Manuel, Cold Spring, Harbor Laboratory press, New York).

As used herein, a functional portion refers to a sequence of a single domain antibody that is of sufficient size such that the interaction of interest is maintained with affinity of $1 \times 10^{-6}$ M or better.

Alternatively, a functional portion comprises a partial deletion of the complete amino acid sequence and still maintains the binding site(s) and protein domain(s) necessary for the binding of and interaction with the target.

As used herein, a functional portion refers to less than 100% of the complete sequence (e.g., 99%, 90%, 80%, 70%, 60% 50%, 40%, 30%, 20%, 10%, 5%, 1% etc.), but comprises 5 or more amino acids or 15 or more nucleotides.

Targets as mentioned herein such as TNF-alpha, TNF-alpha receptor, serum proteins (e.g. serum albumin, serum immunoglobulins, thyroxine-binding protein, transferrin, fibrinogen) and IFN-gamma, IFN-gamma receptor may be fragments of said targets. Thus a target is also a fragment of said target, capable of eliciting an immune response. A target is also a fragment of said target, capable of binding to a single domain antibody raised against the full length target.

A fragment as used herein refers to less than 100% of the sequence (e.g., 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more amino acids. A fragment is of sufficient length such that the interaction of interest is maintained with affinity of 1×10-6 M or better.

A fragment as used herein also refers to optional insertions, deletions and substitutions of one or more amino acids which do not substantially alter the ability of the target to bind to a single domain antibody raised against the wild-type target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A homologous sequence of the present invention may include an anti-TNF-alpha polypeptide which has been humanised. The humanisation of antibodies of the new class of VHHs would further reduce the possibility of unwanted immunological reaction in a human individual upon administration.

One embodiment of the present invention relates to a method for preparing modified polypeptides based upon llama antibodies by determining the amino acid residues of the antibody variable domain (VHH) which may be modified without diminishing the native affinity of the domain for antigen and while reducing its immunogenicity with respect to a heterologous species; the use of VHHs having modifications at the identified residues which are useful for administration to heterologous species; and to the VHH so modified.

More specifically, the invention relates to the preparation of modified VHHs, which are modified for administration to humans, the resulting VHH themselves, and the use of such "humanized" VHHs in the treatment of diseases in humans. By humanised is meant mutated so that immunogenicity upon administration in human patients is minor or nonexistent. Humanising a polypeptide, according to the present invention, comprises a step of replacing one or more of the *Camelidae* amino acids by their human counterpart as found in the human consensus sequence, without that polypeptide losing its typical character, i.e. the humanisation does not significantly affect the antigen binding capacity of the resulting polypeptide. Such methods are known by the skilled addressee.

Humanization of *Camelidae* single domain antibodies requires the introduction and mutagenesis of a limited amount of amino acids in a single polypeptide chain. This is in contrast to humanization of scFv, Fab, (Fab)2 and IgG, which requires the introduction of amino acid changes in two chains, the light and the heavy chain and the preservation of the assembly of both chains.

As a non-limited example, the polypeptide of VHH#12B containing human-like residues in FR2 was humanized. Humanization required mutagenesis of residues in FR1 at position 1 and 5 which were introduced by the primer used for repertoire cloning and do not occur naturally in the llama sequence. Mutagenesis of those residues did not result in loss of binding and/or inhibition activity. Humanization also required mutagenesis of residues in FR3 at position 74, 76, 83, 84, 93. Mutagenesis of those residues did not result in a dramatic loss of binding and/or inhibition activity (see FIG. 4). Combining the mutations of FR1 and FR3 therefore did not affect the binding and/or inhibition activity (FIG. 5).

Humanization also required mutagenesis of residues in FR4 at position 108. Mutagenesis of Q108L resulted in lower production level in *Escherichia coli*. Position 108 is solvent exposed in camelid VHH, while in human antibodies this position is buried at the VH-VL interface (Spinelli, 1996; Nieba, 1997). In isolated VHs position 108 is solvent exposed. The introduction of a non-polar hydrophobic Leu instead of polar uncharged Gln can have a drastic effect on the intrinsic folding/stability of the molecule.

As a non-limited example, the polypeptide represented in the VHH#3E containing camelid hallmark residues at position 37, 44, 45 and 47 with hydrophilic characteristics, was humanized. Replacement of the hydrophilic residues by human hydrophobic residues at positions 44 and 45 (E44G and R45L), did not have an effect on binding and/or inhibition. However, loss of binding and/or inhibition activity was observed when F37V and F47W were introduced. Modeling data confirmed the critical residue 37 to preserve the integrity of the CDR3 loop conformation and hence on activity (see FIG. 6)(all numbering according to the Kabat).

SEQ ID NO: 3 and 14 display more than 90% amino acid sequence homology to human VH framework regions and therefore said VHH might be administered to patients directly without expectation of an immune response therefrom, and without the additional burden of humanisation. Therefore, one aspect of the present invention allows for the direct administration of the polypeptide comprising SEQ ID NO: 3 and 14, homologous sequence thereof, or a functional portion of an homologous sequence thereof to a patient in need of the same.

One embodiment of the present invention is a method for humanizing a VHH comprising the steps of replacing of any of the following residues either alone or in combination:
FR1 position 1, 5, 28 and 30,
the hallmark amino acid at position 44 and 45 in FR2,
FR3 residues 74, 75, 76, 83, 84, 93 and 94,
and positions 103, 104, 108 and 111 in FR4;
numbering according to the Kabat numbering.

One embodiment of the present invention is an anti-TNF-alpha polypeptide, or a nucleic acid capable of encoding said polypeptide for use in treating, preventing and/or alleviating the symptoms of disorders relating to inflammatory processes. TNF-alpha is involved in inflammatory processes, and the blocking of TNF-alpha action can have an anti-inflammatory effect, which is highly desirable in certain disease states such as, for example, Crohn's disease. Our Examples demonstrate VHHs according to the invention which bind TNF-alpha and moreover, block its binding to the TNF-alpha receptor.

The anti-TNF-alpha polypeptides of the present invention are applicable to autoimmune diseases, such as Addison's disease (adrenal), Autoimmune diseases of the ear (ear), Autoimmune diseases of the eye (eye), Autoimmune hepatitis (liver), Autoimmune parotitis (parotid glands), Crohn's disease (intestine), Diabetes Type I (pancreas), Epididymitis (epididymis), Glomerulonephritis (kidneys), Graves' disease (thyroid), Guillain-Barre syndrome (nerve cells), Hashimoto's disease (thyroid), Hemolytic anemia (red blood cells), Systemic lupus erythematosus (multiple tissues), Male infertility (sperm), Multiple sclerosis (nerve cells), Myasthenia Gravis (neuromuscular junction), Pemphigus (primarily skin), Psoriasis (skin), Rheumatic fever (heart and joints), Rheumatoid arthritis (joint lining), Sarcoidosis (multiple tissues and organs), Scleroderma (skin and connective tissues), Sjogren's syndrome (exocrine glands, and other tissues), Spondyloarthropathies (axial skeleton, and other tissues), Thyroiditis (thyroid), Vasculitis (blood vessels). Within parenthesis is the tissue affected by the disease. This listing of autoimmune diseases is intended to be exemplary rather than inclusive.

Autoimmune conditions for which the anti-TNF-alpha polypeptides of the present invention is applicable include, for example, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, and alcohol and drug addiction. In the above-identified autoimmune conditions, the tissue affected is the primary target, in other cases it is the secondary target. These conditions are partly or mostly autoimmune syndromes. Therefore, in treating them, it is possible to use the same methods, or aspects of the same methods that are herein disclosed, sometimes in combination with other methods.

Another embodiment of the present invention is a use of an anti-TNF-alpha polypeptide according to the invention, or a nucleic acid capable of encoding said polypeptide for the preparation of a medicament for treating a disorder relating to inflammatory processes. Examples of disorders include rheumatoid arthritis, Crohn's disease, ulcerative colitis, inflammatory bowel syndrome and multiple sclerosis Polypeptides and nucleic acids according to the present invention may be administered to a subject by conventional routes, such as intravenously. However, a special property of the anti-TNF-alpha polypeptides of the invention is that they penetrate barriers such as tissue membranes and/or tumours and act locally and act locally thereon, and they are sufficiently stable to withstand extreme environments such as in the stomach. Therefore, another aspect of the present invention relates to the delivery of anti-TNF-alpha polypeptides.

A subject according to the invention can be any mammal susceptible to treatment by therapeutic polypeptides.

Oral delivery of anti-TNF-alpha polypeptides of the invention results in the provision of such molecules in an active form in the colon at local sites that are affected by the disorder. These sites may be highly inflamed and contain TNF-alpha-producing cells. The anti-TNF-alpha polypeptides of the invention which bind to TNF-alpha can neutralise the TNF-alpha locally, avoiding distribution throughout the whole body and thus limiting negative side-effects. Genetically modified microorganisms such as *Micrococcus lactis* are able to secrete antibody or functional portions thereof. Such modified microorganisms can be used as vehicles for local production and delivery of antibodies or functional portions thereof in the intestine. By using a strain which produces an anti-TNF-alpha polypeptide, inflammatory bowel syndrome could be treated.

Another aspect of the invention involves delivering anti-TNF polypeptides by using surface expression on or secretion from non-invasive bacteria, such as Gram-positive host organisms like *Lactococcus* spec. using a vector such as described in WO00/23471.

One embodiment of the present invention is an anti-TNF-alpha polypeptide as disclosed herein for use in treating, preventing and/or alleviating the symptoms of disorders susceptible to modulation by a TNF-alpha modulating substance which is able pass through the gastric environment without the substance being inactivated.

Examples of disorders are any that cause inflammation, including, but not limited to rheumatoid arthritis, Crohn's disease, ulcerative colitis, inflammatory bowel syndrome, and multiple sclerosis. As known by persons skilled in the art, once in possession of said polypeptide construct, formulation technology may be applied to release a maximum amount of polypeptide in the right location (in the stomach, in the colon, etc.). This method of delivery is important for treating, prevent and/or alleviate the symptoms of disorders whose targets are located in the gut system.

An aspect of the invention is a method for treating, preventing and/or alleviating the symptoms of a disorder susceptible to modulation by a TNF-alpha modulating substance which is able pass through the gastric environment without being inactivated, by orally administering to a subject an anti-TNF-alpha polypeptide as disclosed herein.

Another embodiment of the present invention is a use of an anti-TNF-alpha polypeptide as disclosed herein for the preparation of a medicament for treating, preventing and/or alleviating the symptoms of disorders susceptible to modulation by a TNF-alpha modulating substance which is able pass through the gastric environment without being inactivated.

An aspect of the invention is a method for delivering a TNF-alpha modulating substance to the gut system without said substance being inactivated, by orally administering to a subject an anti-TNF-alpha polypeptide as disclosed herein.

An aspect of the invention is a method for delivering a TNF-alpha modulating substance to the bloodstream of a subject without the substance being inactivated, by orally administering to a subject an anti-TNF-alpha polypeptide as disclosed herein.

Another embodiment of the present invention is an anti-TNF-alpha polypeptide as disclosed herein for use in treating, preventing and/or alleviating the symptoms or disorders susceptible to modulation by a TNF-alpha modulating substance delivered to the vaginal and/or rectal tract.

Examples of disorders are any that cause inflammation, including, but not limited to rheumatoid arthritis, Crohn's disease, ulcerative colitis, inflammatory bowel syndrome, and multiple sclerosis. In a non-limiting example, a formulation according to the invention comprises an anti-TNF-alpha polypeptide as disclosed herein, in the form of a gel, cream, suppository, film, or in the form of a sponge or as a vaginal ring that slowly releases the active ingredient over time (such formulations are described in EP 707473, EP 684814, U.S. Pat. No. 5,629,001).

An aspect of the invention is a method for treating, preventing and/or alleviating the symptoms of disorders susceptible to modulation by a TNF-alpha modulating substance delivered to the vaginal and/or rectal tract, by vaginally and/or rectally administering to a subject an anti-TNF-alpha polypeptide as disclosed herein.

Another embodiment of the present invention is a use of an anti-TNF-alpha polypeptide as disclosed herein for the preparation of a medicament for treating, preventing and/or alleviating the symptoms of disorders susceptible to modulation by a TNF-alpha modulating substance delivered to the vaginal and/or rectal tract.

An aspect of the invention is a method for delivering a TNF-alpha modulating substance to the vaginal and/or rectal tract without being said substance being inactivated, by administering to the vaginal and/or rectal tract of a subject an anti-TNF-alpha polypeptide as disclosed herein.

An aspect of the invention is a method for delivering a TNF-alpha modulating substance to the bloodstream of a subject without said substance being inactivated, by administering to the vaginal and/or rectal tract of a subject an anti-TNF-alpha polypeptide as disclosed herein.

Another embodiment of the present invention is an anti-TNF-alpha polypeptide as disclosed herein, for use in treating, preventing and/or alleviating the symptoms of disorders susceptible to modulation by a TNF-alpha modulating substance delivered to the nose, upper respiratory tract and/or lung.

Examples of disorders are any that cause inflammation, including, but not limited to rheumatoid arthritis, Crohn's disease, ulcerative colitis, inflammatory bowel syndrome, and multiple sclerosis. In a non-limiting example, a formulation according to the invention, comprises an anti-TNF-alpha polypeptide as disclosed herein in the form of a nasal spray (e.g. an aerosol) or inhaler. Since the polypeptide construct is small, it can reach its target much more effectively than therapeutic IgG molecules.

An aspect of the invention is a method for treating, preventing and/or alleviating the symptoms of disorders susceptible to modulation by a TNF-alpha modulating substance delivered to the upper respiratory tract and lung, by administering to a subject an anti-TNF-alpha polypeptide as disclosed herein, by inhalation through the mouth or nose.

Another embodiment of the present invention is a use of an anti-TNF-alpha polypeptide as disclosed herein for the preparation of a medicament for treating, preventing and/or alleviating the symptoms of disorders susceptible to modulation by a TNF-alpha modulating substance delivered to the nose, upper respiratory tract and/or lung, without said polypeptide being inactivated.

An aspect of the invention is a method for delivering a TNF-alpha modulating substance to the nose, upper respiratory tract and lung without inactivation, by administering to the nose, upper respiratory tract and/or lung of a subject an anti-TNF-alpha polypeptide as disclosed herein.

An aspect of the invention is a method for delivering a TNF-alpha modulating substance to the bloodstream of a subject without inactivation by administering to the nose, upper respiratory tract and/or lung of a subject an anti-TNF-alpha polypeptide as disclosed herein.

One embodiment of the present invention is an anti-TNF-alpha polypeptide as disclosed herein for use in treating, preventing and/or alleviating the symptoms of disorders susceptible to modulation by a TNF-alpha modulating substance delivered to the intestinal mucosa, wherein said disorder increases the permeability of the intestinal mucosa. Because of their small size, an anti-TNF-alpha polypeptide as disclosed herein can pass through the intestinal mucosa and reach the bloodstream more efficiently in subjects suffering from disorders which cause an increase in the permeability of the intestinal mucosa, for example Crohn's disease.

An aspect of the invention is a method for treating, preventing and/or alleviating the symptoms of disorders susceptible to modulation by a TNF-alpha modulating substance delivered to the intestinal mucosa, wherein said disorder increases the permeability of the intestinal mucosa, by orally administering to a subject an anti-TNF-alpha polypeptide as disclosed herein.

This process can be even further enhanced by an additional aspect of the present invention—the use of active transport carriers. In this aspect of the invention, VHH is fused to a carrier that enhances the transfer through the intestinal wall into the bloodstream. In a non-limiting example, this "carrier" is a second VHH which is fused to the therapeutic VHH. Such fusion constructs are made using methods known in the art. The "carrier" VHH binds specifically to a receptor on the intestinal wall which induces an active transfer through the wall.

Another embodiment of the present invention is a use of an anti-TNF-alpha polypeptide as disclosed herein for the preparation of a medicament for treating, preventing and/or alleviating the symptoms of disorders susceptible to modulation by a TNF-alpha modulating substance delivered to the intestinal mucosa, wherein said disorder increases the permeability of the intestinal mucosa.

An aspect of the invention is a method for delivering a TNF-alpha modulating substance to the intestinal mucosa without being inactivated, by administering orally to a subject an anti-TNF-alpha polypeptide of the invention.

An aspect of the invention is a method for delivering a TNF-alpha modulating substance to the bloodstream of a subject without being inactivated, by administering orally to a subject an anti-TNF-alpha polypeptide of the invention.

This process can be even further enhanced by an additional aspect of the present invention—the use of active transport carriers. In this aspect of the invention, an anti-TNF-alpha polypeptide as described herein is fused to a carrier that enhances the transfer through the intestinal wall into the bloodstream. In a non-limiting example, this "carrier" is a VHH which is fused to said polypeptide. Such fusion constructs made using methods known in the art. The "carrier" VHH binds specifically to a receptor on the intestinal wall which induces an active transfer through the wall.

One embodiment of the present invention is an anti-TNF-alpha polypeptide as disclosed herein for use in treating, preventing and/or alleviating the symptoms of disorders susceptible to modulation by a TNF-alpha modulating substance which is able pass through the tissues beneath the tongue effectively.

Examples of disorders are any that cause inflammation, including, but not limited to rheumatoid arthritis, Crohn's disease, ulcerative colitis, inflammatory bowl syndrome, and multiple sclerosis. A formulation of said polypeptide construct as disclosed herein, for example, a tablet, spray, drop is placed under the tongue and adsorbed through the mucus membranes into the capillary network under the tongue.

An aspect of the invention is a method for treating, preventing and/or alleviating the symptoms of disorders susceptible to modulation by a TNF-alpha modulating substance which is able pass through the tissues beneath the tongue effectively, by sublingually administering to a subject an anti-TNF-alpha polypeptide as disclosed herein.

Another embodiment of the present invention is a use of an anti-TNF-alpha polypeptide as disclosed herein for the preparation of a medicament for treating, preventing and/or alleviating the symptoms of disorders susceptible to modulation by a TNF-alpha modulating substance which is able to pass through the tissues beneath the tongue.

An aspect of the invention is a method for delivering a TNF-alpha modulating substance to the tissues beneath the tongue without being inactivated, by administering sublingually to a subject an anti-TNF-alpha polypeptide as disclosed herein.

An aspect of the invention is a method for delivering a TNF-alpha modulating substance to the bloodstream of a subject without being inactivated, by administering orally to a subject an anti-TNF-alpha polypeptide as disclosed herein.

One embodiment of the present invention is an anti-TNF-alpha polypeptide as disclosed herein for use in treating, preventing and/or alleviating the symptoms of disorders susceptible to modulation by a TNF-alpha modulating substance which is able pass through the skin effectively.

Examples of disorders are any that cause inflammation, including, but not limited to rheumatoid arthritis, Crohn's disease, ulcerative colitis, inflammatory bowl syndrome, and multiple sclerosis. A formulation of said polypeptide construct, for example, a cream, film, spray, drop, patch, is placed on the skin and passes through.

An aspect of the invention is a method for treating, preventing and/or alleviating the symptoms of disorders susceptible to modulation by a TNF-alpha modulating substance which is able pass through the skin effectively, by topically administering to a subject an anti-TNF-alpha polypeptide as disclosed herein.

Another embodiment of the present invention is a use of an anti-TNF-alpha polypeptide as disclosed herein for the preparation of a medicament for treating, preventing and/or alleviating the symptoms of disorders susceptible to modulation by a TNF-alpha modulating substance which is able pass through the skin effectively.

An aspect of the invention is a method for delivering a TNF-alpha modulating substance to the skin without being inactivated, by administering topically to a subject an anti-TNF-alpha polypeptide as disclosed herein.

An aspect of the invention is a method for delivering a TNF-alpha modulating substance to the bloodstream of a subject, by administering topically to a subject an anti-TNF-alpha polypeptide as disclosed herein.

In another embodiment of the present invention, an anti-TNF-alpha polypeptide further comprises a carrier single domain antibody (e.g. VHH) which acts as an active transport carrier for transport said anti-TNF-alpha polypeptide, from the lung lumen to the blood.

An anti-TNF-alpha polypeptide further comprising a carrier binds specifically to a receptor present on the mucosal surface (bronchial epithelial cells) resulting in the active transport of the polypeptide from the lung lumen to the blood. The carrier single domain antibody may be fused to the polypeptide construct. Such fusion constructs may be made using methods known in the art and are describe herein. The "carrier" single domain antibody binds specifically to a receptor on the mucosal surface which induces an active transfer through the surface.

Another aspect of the present invention is a method to determine which single domain antibodies (e.g. VHHs) are actively transported into the bloodstream upon nasal administration. Similarly, a naïve or immune VHH phage library can be administered nasally, and after different time points after administration, blood or organs can be isolated to rescue phages that have been actively transported to the bloodstream. A non-limiting example of a receptor for active transport from the lung lumen to the bloodstream is the Fc receptor N (FcRn). One aspect of the invention includes the VHH molecules identified by the method. Such VHH can then be used as a carrier VHH for the delivery of a therapeutic VHH to the corresponding target in the bloodstream upon nasal administration.

In one aspect of the invention, one can use an anti-TNF-alpha polypeptide as disclosed herein, in order to screen for agents that modulate the binding of the polypeptide to TNF-alpha. When identified in an assay that measures binding or said polypeptide displacement alone, agents will have to be subjected to functional testing to determine whether they would modulate the action of the antigen in vivo. Examples of screening assays are given below primarily in respect of SEQ ID NO: 3, though any anti-TNF-alpha polypeptide as disclosed herein as disclosed herein may be appropriate.

In an example of a displacement experiment, phage or cells expressing TNF-alpha or a fragment thereof are incubated in binding buffer with, for example, a polypeptide represented by SEQ ID NO: 3 which has been labeled, in the presence or absence of increasing concentrations of a candidate modulator. To validate and calibrate the assay, control competition reactions using increasing concentrations of said polypeptide and which is unlabeled, can be performed. After incubation, cells are washed extensively, and bound, labeled polypeptide is measured as appropriate for the given label (e.g., scintillation counting, fluorescence, etc.). A decrease of at least 10% in the amount of labeled polypeptide bound in the presence of candidate modulator indicates displacement of binding by the candidate modulator. Candidate modulators are considered to bind specifically in this or other assays described herein if they displace 50% of labeled polypeptide (sub-saturating polypeptide dose) at a concentration of 1 μM or less.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of, for example, the polypeptide represented by SEQ ID NO: 3 from the aqueous phase to TNF-alpha immobilized in a membrane on the sensor. This change in mass is measured as resonance units versus time after injection or removal of the said polypeptide or candidate modulator and is measured using a Biacore Biosensor (Biacore AB). TNF-alpha can be for example immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for the binding of SEQ ID NO:3 to TNF-alpha in an SPR assay can be fine-tuned by one of skill in the art using the conditions reported by Sarrio et al. as a starting point.

SPR can assay for modulators of binding in at least two ways. First, a polypeptide represented by SEQ ID NO: 3, for example, can be pre-bound to immobilized TNF-alpha followed by injection of candidate modulator at a concentration ranging from 0.1 nM to 1 μM. Displacement of the bound polypeptide can be quantitated, permitting detection of modulator binding. Alternatively, the membrane-bound TNF-alpha can be pre-incubated with a candidate modulator and challenged with, for example, a polypeptide represented by SEQ ID NO: 3. A difference in binding affinity between said polypeptide and TNF-alpha pre-incubated with the modulator, compared with that between said polypeptide and TNF-alpha in absence of the modulator will demonstrate binding or displacement of said polypeptide in the presence of modulator. In either assay, a decrease of 10% or more in the amount of said polypeptide bound in the presence of candidate modulator, relative to the amount of said polypeptide bound in the absence of candidate modulator indicates that the candidate modulator inhibits the interaction of TNF-alpha and said polypeptide.

Another method of detecting inhibition of binding of, for example, a polypeptide represented by SEQ ID NO: 3, to TNF-alpha uses fluorescence resonance energy transfer (FRET). FRET is a quantum mechanical phenomenon that occurs between a fluorescence donor (D) and a fluorescence acceptor (A) in close proximity to each other (usually <100 Å of separation) if the emission spectrum of D overlaps with the excitation spectrum of A. The molecules to be tested, e.g. a polypeptide represented by SEQ ID NO: 3 and a TNF-alpha are labelled with a complementary pair of donor and acceptor fluorophores. While bound closely together by the TNF-alpha: polypeptide interaction, the fluorescence emitted upon excitation of the donor fluorophore will have a different wavelength from that emitted in response to that excitation wavelength when the said polypeptide and TNF-alpha are not bound, providing for quantitation of bound versus unbound molecules by measurement of emission intensity at each wavelength. Donor fluorophores with which to label the TNF-alpha are well known in the art. Of particular interest are variants of the A. Victoria GFP known as Cyan FP (CFP, Donor (D)) and Yellow FP (YFP, Acceptor (A)). As an example, the YFP variant can be made as a fusion protein with TNF-alpha. Vectors for the expression of GFP variants as fusions (Clontech) as well as fluorophore-labeled reagents (Molecular Probes) are known in the art. The addition of a candidate modulator to the mixture of fluorescently-labelled polypeptide and YFP-TNF-alpha will result in an inhibition of energy transfer evidenced by, for example, a decrease in YFP fluorescence relative to a sample without the candidate modulator. In an assay using FRET for the detection of TNF-alpha: polypeptide interaction, a 10% or greater decrease in the intensity of fluorescent emission at the acceptor wavelength in samples containing a candidate modulator, relative to samples without the candidate modulator, indicates that the candidate modulator inhibits the TNF-alpha:polypeptide interaction.

A sample as used herein may be any biological sample containing TNF-alpha such as clinical (e.g. cell fractions, whole blood, plasma, serum, tissue, cells, etc.), derived from clinical, agricultural, forensic, research, or other possible samples. The clinical samples may be from human or animal origin. The sample analysed can be both solid or liquid in nature. It is evident when solid materials are used, these are first dissolved in a suitable solution.

A variation on FRET uses fluorescence quenching to monitor molecular interactions. One molecule in the interacting pair can be labelled with a fluorophore, and the other with a molecule that quenches the fluorescence of the fluorophore when brought into close apposition with it. A change in fluorescence upon excitation is indicative of a change in the association of the molecules tagged with the fluorophore: quencher pair. Generally, an increase in fluorescence of the labelled TNF-alpha is indicative that anti-TNF-alpha polypeptide bearing the quencher has been displaced. For quenching assays, a 10% or greater increase in the intensity of fluorescent emission in samples containing a candidate modulator, relative to samples without the candidate modulator, indicates that the candidate modulator inhibits TNF-alpha: anti-TNF-alpha polypeptide interaction.

In addition to the surface plasmon resonance and FRET methods, fluorescence polarization measurement is useful to quantitate binding. The fluorescence polarization value for a fluorescently-tagged molecule depends on the rotational correlation time or tumbling rate. Complexes, such as those formed by TNF-alpha associating with a fluorescently labelled anti-TNF-alpha polypeptide, have higher polarization values than uncomplexed, labelled polypeptide. The inclusion of a candidate inhibitor of the TNF-alpha:anti-TNF-alpha polypeptide interaction results in a decrease in fluorescence polarization, relative to a mixture without the candidate inhibitor, if the candidate inhibitor disrupts or inhibits the interaction of TNF-alpha with said polypeptide. Fluorescence polarization is well suited for the identification of small molecules that disrupt the formation of TNF-alpha: anti-TNF-alpha polypeptide complexes. A decrease of 10% or more in fluorescence polarization in samples containing a candidate modulator, relative to fluorescence polarization in a sample lacking the candidate modulator, indicates that the candidate modulator inhibits the TNF-alpha: anti-TNF-alpha polypeptide interaction.

Another alternative for monitoring TNF-alpha: anti-TNF-alpha polypeptide interactions uses a biosensor assay. ICS biosensors have been described in the art (Australian Membrane Biotechnology Research Institute; Cornell B, Braach-Maksvytis V, King L, Osman P, Raguse B, Wieczorek L, and Pace R. "A biosensor that uses ion-channel switches" Nature 1997, 387, 580). In this technology, the association of TNF-alpha and a anti-TNF-alpha polypeptide is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of TNF-alpha and said polypeptide. It is important to note that in assays testing the interaction of TNF-alpha with an anti-TNF-alpha polypeptide, it is possible that a modulator of the interaction need not necessarily interact directly with the domain(s) of the proteins that physically interact with said polypeptide. It is also possible that a modulator will interact at a location removed from the site of interaction and cause, for example, a conformational change in the TNF-alpha. Modulators (inhibitors or agonists) that act in this manner are nonetheless of interest as agents to modulate the binding of TNF-alpha to its receptor.

Any of the binding assays described can be used to determine the presence of an agent in a sample, e.g., a tissue sample, that binds to TNF-alpha, or that affects the binding of, for example, a polypeptide represented by SEQ ID NO: 3 to the TNF-alpha. To do so a TNF-alpha is reacted with said polypeptide in the presence or absence of the sample, and polypeptide binding is measured as appropriate for the binding assay being used. A decrease of 10% or more in the binding of said polypeptide indicates that the sample contains an agent that modulates the binding of said polypeptide to the TNF-alpha. Of course, the above-generalized method might easily be applied to screening for candidate modulators which alter the binding between any anti-TNF-alpha polypeptide of the invention, an homologous sequence thereof, a functional portion thereof or a functional portion of an homologous sequence thereof, and TNF-alpha or a fragment thereof.

One embodiment of the present invention is an unknown agent identified by the method disclosed herein.

One embodiment of the present invention is an unknown agent identified by the method disclosed herein for use in treating, preventing and/or alleviating the symptoms of disorders relating to inflammatory processes.

Another embodiment of the present invention is a use of an unknown agent identified by the method disclosed herein for use in treating, preventing and/or alleviating the symptoms of disorders relating to inflammatory processes.

Examples of disorders include rheumatoid arthritis, Crohn's disease, ulcerative colitis, inflammatory bowel syndrome and multiple sclerosis A cell that is useful according to the invention is preferably selected from the group consisting of bacterial cells such as, for example, *E. coli*, yeast cells such as, for example, *S. cerevisiae*, *P. pastoris*, insect cells or mammal cells.

A cell that is useful according to the invention can be any cell into which a nucleic acid sequence encoding a polypeptide comprising an anti-TNF-alpha of the invention, an homologous sequence thereof, a functional portion thereof or a functional portion of an homologous sequence thereof according to the invention can be introduced such that the polypeptide is expressed at natural levels or above natural levels, as defined herein. Preferably a polypeptide of the invention that is expressed in a cell exhibits normal or near normal pharmacology, as defined herein. Most preferably a polypeptide of the invention that is expressed in a cell comprises the nucleotide sequence capable of encoding any one of the amino acid sequences presented in Table 1 or capable of encoding an amino acid sequence that is at least 70% identical to the amino acid sequence presented in Table 1.

According to a preferred embodiment of the present invention, a cell is selected from the group consisting of COS7-cells, a CHO cell, a LM (TK-) cell, a NIH-3T3 cell, HEK-293 cell, K-562 cell or a 1321N1 astrocytoma cell but also other transfectable cell lines.

In general, "therapeutically effective amount", "therapeutically effective dose" and "effective amount" means the amount needed to achieve the desired result or results (modulating TNF-alpha binding; treating or preventing inflammation). One of ordinary skill in the art will recognize that the potency and, therefore, an "effective amount" can vary for the various compounds that modulate TNF-alpha binding used in the invention. One skilled in the art can readily assess the potency of the compound.

As used herein, the term "compound" refers to an anti-TNF-alpha polypeptide of the present invention, a composition, or a nucleic acid capable of encoding said polypeptide or an agent identified according to the screening method described herein or said polypeptide comprising one or more derivatised amino acids.

By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained.

Anti-TNF-alpha polypeptides as disclosed herein is useful for treating or preventing conditions in a subject and comprises administering a pharmaceutically effective amount of a compound or composition.

Anti-TNF polypeptides of the present invention are useful for treating or preventing conditions relating to rheumatoid arthritis, Crohn's disease, ulcerative colitis, inflammatory bowel syndrome and multiple sclerosis in a subject and comprises administering a pharmaceutically effective amount of a compound or composition that binds TNF-alpha.

Anti-TNF-alpha polypeptides as disclosed here in are useful for treating or preventing conditions in a subject and comprises administering a pharmaceutically effective amount of a compound combination with another, such as, for example, aspirin.

The anti-TNF-alpha polypeptides as disclosed here in are useful for treating or preventing conditions relating to rheumatoid arthritis, Crohn's disease, ulcerative colitis, inflammatory bowel syndrome and multiple sclerosis in a subject and comprises administering a pharmaceutically effective amount of a compound combination with another, such as, for example, aspirin.

The present invention is not limited to the administration of formulations comprising a single compound of the invention. It is within the scope of the invention to provide combination treatments wherein a formulation is administered to a patient in need thereof that comprises more than one compound of the invention.

Conditions mediated by TNF-alpha include, but are not limited rheumatoid arthritis, Crohn's disease, ulcerative colitis, inflammatory bowel syndrome and multiple sclerosis.

A compound useful in the present invention can be formulated as pharmaceutical compositions and administered to a mammalian host, such as a human patient or a domestic animal in a variety of forms adapted to the chosen route of administration, i.e., orally or parenterally, by intranasally by inhalation, intravenous, intramuscular, topical or subcutaneous routes.

A compound of the present invention can also be administered using gene therapy methods of delivery. See, e.g., U.S. Pat. No. 5,399,346, which is incorporated by reference in its entirety. Using a gene therapy method of delivery, primary cells transfected with the gene for the compound of the present invention can additionally be transfected with tissue specific promoters to target specific organs, tissue, grafts, tumors, or cells.

Thus, the present compound may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compound may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the present compound can be dissolved or dispersed at effective levels, optionally with the aid of non-toxic surfactants. Adjuvants such as fragrances and additional antimicrobial agents can be added to optimize the properties for a given use.

The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compound to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. Also the dosage of the compound varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

The invention provides for an agent that is a modulator of TNF-alpha/TNF-alpha-receptor interactions.

The candidate agent may be a synthetic agent, or a mixture of agents, or may be a natural product (e.g. a plant extract or culture supernatant). A candidate agent according to the invention includes a small molecule that can be synthesized, a natural extract, peptides, proteins, carbohydrates, lipids etc.

Candidate modulator agents from large libraries of synthetic or natural agents can be screened. Numerous means are currently used for random and directed synthesis of saccharide, peptide, and nucleic acid based agents. Synthetic agent libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural agents in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and agents are readily modified through conventional chemical, physical, and biochemical means.

Useful agents may be found within numerous chemical classes. Useful agents may be organic agents, or small organic agents. Small organic agents have a molecular weight of more than 50 yet less than about 2,500 daltons, preferably less than about 750, more preferably less than about 350 daltons. Exemplary classes include heterocycles, peptides, saccharides, steroids, and the like. The agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

For primary screening, a useful concentration of a candidate agent according to the invention is from about 10 mM to about 100 μM or more (i.e. 1 mM, 10 mM, 100 mM, 1 M etc.). The primary screening concentration will be used as an upper limit, along with nine additional concentrations, wherein the additional concentrations are determined by reducing the primary screening concentration at half-log intervals (e.g. for 9 more concentrations) for secondary screens or for generating concentration curves.

High Throughput Screening Kit

A high throughput screening kit according to the invention comprises all the necessary means and media for performing the detection of an agent that modulates TNF-alpha/TNFalpha receptor interactions by interacting with TNF-alpha in the presence of a polypeptide, preferably at a concentration in the range of 1 µM to 1 mM.

The kit comprises the following. Recombinant cells of the invention, comprising and expressing the nucleotide sequence encoding TNF-alpha, which are grown according to the kit on a solid support, such as a microtiter plate, more preferably a 96 well microtiter plate, according to methods well known to the person skilled in the art especially as described in WO 00/02045. Alternatively TNF-alpha is supplied in a purified form to be immobilized on, for example, a 96 well microtiter plate by the person skilled in the art. Alternatively TNF-alpha is supplied in the kit pre-immobilized on, for example, a 96 well microtiter plate. The TNF-alpha may be whole TNF-alpha or a fragment thereof.

Modulator agents according to the invention, at concentrations from about 1 µM to 1 mM or more, are added to defined wells in the presence of an appropriate concentration of anti-TNF-alpha polypeptide, an homologous sequence thereof, a functional portion thereof or a functional portion of an homologous sequence thereof, said concentration of said polypeptide preferably in the range of 1 µM to 1 mM. Kits may contain one or more anti-TNF-alpha polypeptide (e.g. one or more of a polypeptide represented by any of the SEQ ID NOs: 1 to 15 or other anti-TNF-alpha polypeptides, an homologous sequence thereof, a functional portion thereof or a functional portion of an homologous sequence thereof).

Binding assays are performed as according to the methods already disclosed herein and the results are compared to the baseline level of, for example TNF-alpha binding to an anti-TNF-alpha polypeptide, an homologous sequence thereof, a functional portion thereof or a functional portion of an homologous sequence thereof, but in the absence of added modulator agent. Wells showing at least 2 fold, preferably 5 fold, more preferably 10 fold and most preferably a 100 fold or more increase or decrease in TNF-alpha-polypeptide binding (for example) as compared to the level of activity in the absence of modulator, are selected for further analysis.

Other Kits Useful According to the Invention

The invention provides for kits useful for screening for modulators of TNF-alpha/TNF-alpha receptor binding, as well as kits useful for diagnosis of disorders characterised by dysfunction of TNF-alpha. The invention also provides for kits useful for screening for modulators of disorders as well as kits for their diagnosis, said disorders characterised by one or more process involving TNF-alpha. Kits useful according to the invention can include an isolated TNF-alpha. Alternatively, or in addition, a kit can comprise cells transformed to express TNF-alpha. In a further embodiment, a kit according to the invention can comprise a polynucleotide encoding TNF-alpha. In a still further embodiment, a kit according to the invention may comprise the specific primers useful for amplification of TNF-alpha. Kits useful according to the invention can comprise an isolated TNF-alpha polypeptide, a homologue thereof, or a functional portion thereof. A kit according to the invention can comprise cells transformed to express said polypeptide. Kits may contain more than one polypeptide. In a further embodiment, a kit according to the invention can comprise a polynucleotide encoding TNF-alpha. In a still further embodiment, a kit according to the invention may comprise the specific primers useful for amplification of a macromolecule such as, for example, TNF-alpha. All kits according to the invention will comprise the stated items or combinations of items and packaging materials therefore. Kits will also include instructions for use.

EXAMPLES

The invention is illustrated by the following non-limiting examples.

Example 1

Example of *Camelidae* Antibodies Against Human Tumor Necrosis Factor Alpha

1) Immunization and Library Constructions

A llama (*Llama glama*) was immunized with human TNF-alpha. For immunization, the cytokine was formulated as an emulsion with an appropriate, animal-friendly adjuvant (Specoll, CEDI Diagnostics B.V.). The antigen cocktail was administered by double-spot injections intramuscularly in the neck. The animal received 6 injections of the emulsion, containing 100 µg of TNF-alpha at weekly intervals. At different time points during immunization, 10-ml blood samples were collected from the animal and sera were prepared. The induction of an antigen specific humoral immune response was verified using the serum samples in an ELISA experiment with TNF (data not shown). Five days after the last immunization, a blood sample of 150 ml was collected. From this sample, conventional and heavy-chain antibodies (HcAbs) were fractionated (Lauwereys et al. 1998) and used in an ELISA, which revealed that the HcAbs were responsible for the antigen specific humoral immune response (data not shown). Peripheral blood lymphocytes (PBLs), as the genetic source of the llama heavy chain immunoglobulins (HcAbs), were isolated from the 150-ml blood sample using a Ficoll-Paque gradient (Amersham Biosciences) yielding $5 \times 10^8$ PBLs. The maximal diversity of antibodies is expected to be equal to the number of sampled B-lymphocytes, which is about 10% of the number of PBLs ($5 \times 10^7$). The fraction of heavy-chain antibodies in llama is up to 20% of the number of B-lymphocytes. Therefore, the maximal diversity of HcAbs in the 150 ml blood sample is calculated as $10^7$ different molecules. Total RNA (around 400 µg) was isolated from these cells using an acid guanidinium thiocyanate extraction (Chomczynski and Sacchi, 1987).

cDNA was prepared on 100 µg total RNA with M-MLV Reverse Transcriptase (Gibco BRL) and oligo-dT-primer or hexanucleotide random primers (Amersham Biosciences) as described before (de Haard et al., 1999). The cDNA was purified with a phenol/chloroform extraction combined with an ethanol precipitation and subsequently used as template to specifically amplify the VHH repertoire.

The VHH repertoire was amplified using oligo-dT primed cDNA as template with a single degenerated framework) (FR1) primer ABL013 (5'-GAGGTBCARCTGCAGGAST-CYGG-3') (SEQ ID NO:98), introducing a PstI restriction site (in bold), in combination with the oligo-dT primer as is described in EP01205100.9. This amplification yields two fragments of 1650 bp and 1300 bp, the latter being the product derived from the CH1-deleted HcAb genes. The smaller PCR-product was gel purified and subsequently digested with PstI and BstEII. The BstEII-site frequently occurs within the FR4 of heavy-chain derived VHH encoding DNA-fragments.

Alternatively, the VHH-repertoire was amplified in a hinge-dependent approach using two IgG specific oligonucleotide primers. In a single PCR reaction a short (5'-AACAGTTAAGCTTCCGCTT GCGGCCGCGGAGCTGGGGTCTTCGCTGTGGTGCG-3') (SEQ ID NO:99) or long (5'-AACAGTTAAGCTTCCGCTT GCGGCCGCTGGTTGTGG TTTTGGTGTCTTGGGTT-3') (SEQ ID NO:100) hinge primer known to be specific for HcAbs was combined with the FR1-primer ABL013 (see above). A PstI and NotI (bold underlined) restriction site was introduced within the FR1 and hinge primers respectively, to allow cloning. Subsequently, the DNA fragments were ligated into PstI-BstEII or PstI-NotI digested phagemid vector pAX004, which is identical to pHEN1 (Hoogenboom et al., 1991), but encodes a carboxyterminal $(His)_6$- and c-myc-tag for purification and detection, respectively. The ligation mixture was desalted on a Microcon filter (YM-50, Millipore) and electroporated into E. coli TG1 cells to obtain a library containing $1.8 \times 10^7$ clones. The transformed cells were grown overnight at 37° C. on a single 20×20 cm plate with LB containing 100 µg/ml ampicillin and 2% glucose. The colonies were scraped from plates using 2×TY medium and stored at −80° C. in 20% glycerol.

As quality control the percentage of insert containing clones was verified on 24 clones for each library by PCR using a combination of vector based primers. This analysis revealed that 95% of the clones contained a VHH encoding insert. The variability was examined by HinfI fingerprint analysis of the amplified VHH fragment of these 24 clones, thereby showing that all clones were indeed different (data not shown).

2) Selection of Antagonistic Anti-TNF VHH's

From both libraries phage was prepared. To rescue the polyclonal phage repertoire, libraries were grown to logarithmic phase (OD600=0.5) at 37° C. in 2×TY containing 100 µg/ml ampicillin and 2% glucose and subsequently superinfected with M13K07 helper phage for 30 minutes at 37° C. Infected cells were pelleted for 5 minutes at 4000 rpm and resuspended in 2×TY containing 100 µg/ml ampicillin and 25 µg/ml kanamycin. Bacteriophage was propagated by overnight growth at 37° C. and 250 rpm. Overnight cultures were centrifuged for 15 minutes at 4500 rpm and phage was precipitated with one fifth volume of a [20% polyethyleneglycol 6000, 1.5 M NaCl]-solution by incubation for 30 minutes on ice. Phage was pelleted by centrifugation for 15 minutes at 4000×g and 4° C. After resuspension of the phages in PBS, cell debris was pelleted by centrifugation for 1 minute at maximal speed (15000×g) in microcentrifuge tubes. The supernatant containing the phage particles was transferred to a new tube and again phage was precipitated as described above. Phage was dissolved in PBS and separated from remaining cell debris as mentioned above. The titer of phage was determined by infection of logarithmic TG1 cells followed by plating on selective medium.

The library was selected using in vitro biotinylated TNF-alpha. The biotinylation was carried out as described by Magni et al (Anal Biochem 2001, 298, 181-188). The incorporation of biotin in TNF was evaluated by SDS-PAGE analysis and detection with Extravidin-alkaline phosphatase conjugate (Sigma). The functionality of the modified protein was evaluated for its ability to bind to the solid phase coated recombinant a p75 receptor.

VHH were selected by capturing biotinylated TNF-alpha (10 to 400 ng per well during 2 hours at room temperature) on streptavidin coated microtiter plates (coated with 100 µl of 10 µg/ml streptavidin during 16 hours at +4° C.). Antagonistic VHH were obtained by elution with an excess of receptor, either the extracellular ligand binding domain or with cells expressing the receptor. After 2 hours incubation of phage with captured cytokine, the non-specific phage was washed away, while specific phage displaying antagonistic VHH was eluted for 30 minutes with receptor (extracellular domain of CD120b or p75; 10 µM) or with receptor displaying cells ($>10^5$ KYM cells per well). High enrichments, i.e. the ratio of the number of phage eluted with receptor and those eluted by serum albumin (50 µg per well), of more than a factor of 20 suggested the successful selection of TNF-alpha specific clones. Alternatively, instead of elution with receptor a standard procedure was applied, in which a low pH causes the denaturation of VHH and/or antigen (0.1 M glycine buffer pH 2.5). Log phase growing E. coli cells were infected with the eluted and neutralized phage and plated on selective medium.

Individual clones were picked and grown in microtiter plate for the production of VHH in culture supernatant. ELISA screening with TNF-alpha captured on Extravidin coated plates revealed about 50% positive clones. HinfI-fingerprint analysis showed that 13 different clones were selected, which were grown and induced on 50 ml scale. The sequences of said clones are shown in Table 1.

Five clones, coded VHH#1A, #2B, #3E, #3G, #7B and #12B, with different sequences (FIG. 1) were characterized in more detail. VHH#3E, #3G and #7B are single-domain antibody fragments carrying the typical hydrophilic residue at position 45 (arginine) and the phenylalanine to tryptophan substitution in position 47 in FR2 thereby conferring the advantageous characteristics in terms of solubility. VHH#1A contains the hydrophobic FR2 residues typically found in double-chain antibodies of human origin or from other species, but compensating this loss in hydrophilicity by the charged arginine residue on position 103 that substitutes the conserved tryptophan residue present in VH from double-chain antibodies (PCT/EP02/07804). A new class of humanised Camelidae single-domain antibodies described in this invention is represented by VHH#2B and VHH#12B, which contains the hydrophobic residues in FR2 in combination with the hydrophobic residue tryptophan at position 103. Larger amounts of antibody fragments were expressed by cultivation on 50 ml scale and purified by IMAC using TALON resin (Clontech). After dialysis against PBS to remove the eluent imidazol the amount of VHH was determined by OD280; approximately 300 µg of VHH was obtained from each clone.

This material was used for determining the sensitivity of detection of (biotinylated) TNF in ELISA. For this purpose a streptavidin (10 µg/ml) coated microtiterplate was employed for capture of biotinylated TNF (1 µg/ml), VHH was diluted in 0.2% casein/PBS and incubated for 2 hours at room temperature. Bound VHH was detected with anti-MYC mAB 9E10 (0.5 µg/ml) and anti-mouse AP conjugate (1000-fold diluted, Sigma). The results are shown in FIG. 2.

3) Determination of Antagonistic Effect in Cytotoxicity Assay with KYM Cell Line TNF-alpha-induced cytostasis/cytotoxicity was determined by the colorimetric MTT assay as described by Vandenabeele and colleagues (Vandenabeele, P., Declercq, W., Vercammen, D., Van de Craen, M., Grooten, J., Loetscher, H., Brockhaus, M., Lesslauer, W., Fiers, W. (1992) Functional characterization of the human tumor necrosis factor receptor p75 in a transfected rat/mouse T cell hybridoma. J. Exp. Med. 176, 1015-1024.). MTT (3-(4,5-cimethylthiazol-2-yl)-2,5-diphenyl tetrazolium bromide) is a pale yellow substrate that is cleaved by living cells to yield a dark blue formazan product. This process requires active mitochondria, and even freshly dead cells do not cleave significant amounts of MTT. KYM cells (Sekiguchi M, Shiroko Y, Suzuki T, Imada M, Miyahara M, Fujii G. (1985) Characterization of a human rhabdomyosarcoma cell strain in tissue culture. Biomed. Pharmacother. 39, 372-380.) were seeded in 96 well microtiterplates and cultured in the presence or absence of TNF-alpha (0.216 ng/ml or approx. 5 pM of trimer). In addition to TNF variable amounts of antibody (VHH or Remicade) were included during cultivation. For the assay MTT was added to the culture medium at a final concentration of 500 µg/ml and as represented in the following sequence alignment in which DP-47 is SEQ ID NO:101 and VHH#12B is SEQ ID NO:102:

```
DP-47    EVQLLESGGGLVQPGGSLRLSCAASGFTFS SYAMS      WVRQAPGKGLEWVS AISGSGGSTYY
VHH#12B  QVQLQESGGGLVQPGGSLRLSCAASGFEFE NHWMY      WVRQAPGKGLEWVS TVNTNGLITRY

DP-47    ADSVKG RFTISRDNSKNTLYLQMNSLRAEDTAVYYCAK ------------- -----------
VHH#12B  ADSVKG RFTISRDNAKYTLYLQMNSLKSEDTAVYYCTK VLPPYSDDSRTNAD WGQGTQVTVSS
``` the plates were incubated at 37° C. to achieve cleavage of MTT by mitochondrial enzymes. The formed formazon product, which appear as black, fuzzy crystals on the bottom of the well were dissolved by addition of acid isopropanol (40 nM HCl in isopropanol) or DMSO. The absorbance is measured at 570 nm.

The MTT assay (FIG. 3) shows that VHH#1A, which has arginine on position 103 in combination with the human-like hydrophobic residues in FR2, has a moderate antagonistic effect (1050~100 nM). VHH#7B with the characteristic hydrophilic residues in FR2 does not prevent binding of TNF-α to its ligand in spite of its sensitive detection of the cytokine in ELISA (curve not sh A microtiter plate was coated overnight at 4° C. with Enbrel (Wyeth) at 2 μg/ml in PBS. The plate was washed five times with PBS-Tween and blocked for 1 hour at room temperature with PBS containing 1% casein. The plate was washed five times with PBS-Tween. Biotinylated human TNF-alpha (80 μg/ml) was pre-incubated with a dilution series of mutant or wild type VHH#12B for 1 hr at RT and the mixture was incubated for 1 hr at room temperature in the wells of the microtiterplate. The plate was washed five times with PBS-Tween. Bound human TNF-α was detected using Extravidin-AP (1/1,000 dilution) and paranitrophenylphosphate (pNPP). Signals were measured after 30 minutes at 405 nm. The results are presented in FIGS. 4 and 5. The IC50 increased 3-fold from 66 nM (wild type) to 200 nM (mutant Q1E+Q5L+A74S+Y76N+K83R+P84A). Mutation of position T93A resulted in loss of inhibition (data not shown). The positions that still need to be humanized are: E28, E30 and Q108. However, E28 and E30 are part of the H1 canonical structure and thus part of the CDR1 according to Chothia numbering system.

The amino acid sequences of mutant VHHs are presented in Table 4 SEQ ID NOs: 17 to 19.

3) Mutagenesis of VHH#3E

VHH#3E was mutated by using a non-PCR based site-directed mutagenesis method as described above. The obtained mutant VHH's and the mutagenic primers are listed in Table 3.

All mutant VHH's expressed comparable to the wild type. The purified mutant VHH's were analyzed for binding in ELISA and inhibition capacity in receptor binding assay identical to the method described above.

The results of the ELISA are shown in FIG. 6, those from the receptor binding assay in FIG. 7.

The amino acid sequences of mutant VHHs are presented in Table 4 SEQ ID NOs 21 to 24.

Example 3

Isolation of Antagonistic VHH Against Mouse TNF-Alpha

1) Selection of Anti-Mouse TNF-Alpha VHH

In order to perform efficacy studies in mouse models for IBD or Crohn's disease mouse TNF specific VHH were selected. Therefore a llama was immunized with mouse TNF-alpha as described in Example 1. RNA was extracted from PBL's sampled 4 and 10 days after the last immunization, as well as from a biopsy taken from a lymph node after day 4. Total RNA was converted in either random primed or oligo-dT primed cDNA and used as template for the amplification of the VHH encoding gene segments using Ig derived primers or a combination of oligo-dT primer and a single Ig primer (see example 1). With the Ig primers a library containing $8.5 \times 10^7$ clones was generated from the first PBL's, and a library with $7 \times 10^6$ clones for the second PBL sample and $5.8 \times 10^8$ clones for the lymph node. Using the combination of the oligo-dT primer and the Ig primer libraries from the first PBL sample were made containing $1.2 \times 10^8$ clones, from the second sample of PBL's a library of $5.7 \times 10^7$ clones and the lymph node derived library contained $2 \times 10^8$ clones. The libraries were pooled dependent on the used combination of primers and the resulting two libraries were grown for propagation of phage as was described before. Selections were performed on biotinylated mouse TNF-alpha captured on coated streptavidin, bound phage was eluted by competition with the human receptor p75, which is known to cross-react with mouse TNF-alpha. Two distinct mouse TNF-alpha specific VHH (VHH#m3F and VHH#m9E) were selected from the library obtained by amplification with Ig derived primers, while two closely related VHH's were retrieved from the library constructed by PCR with oligo-dT primer and Ig-primer (FIG. 8).

2) Determination Antagonistic Efficacy in Cytotoxicity Assay with L929 Cell Line (FIG. 9)

The same type of assay was applied as described in Example 1, but with the murine cell line L929. VHH#m3F and VHH#m4B (FIG. 9) turned out to be 10-fold more potent then the other two VHH's.

Example 4

Enhancing the Antagonistic Efficacy by Increasing the Avidity Using Multivalent *Camelidae* Antibodies 1) Antagonistic Efficacy of Bi-, Tri- and Tetravalent VHH Against Human and Mouse TNF-Alpha The *E. coli* production vector pAX11 (FIG. 10) was designed, which allows the two-step cloning of bivalent or bispecific VHH. The carboxy terminal VHH is cloned first with PstI and BstEII, while in the second step the other VHH is inserted by SfiI and NotI, which do not cut within the first gene fragment. The procedure avoids the enforcement of new sites by amplification and thus the risk of introducing PCR errors.

With this vector the bivalent derivative of the antagonistic anti-human TNF-alpha VHH#3E was generated. The plasmid vector encoding the bivalent VHH was used to generate a tri- and tetrameric derivative, which was accomplished by partial digestion of the plasmid with BstEII, which occurs in both VHH gene segments. The linearized vector was purified from gel, subsequently de-phosphorylated and used as acceptor for cloning of the BstEII fragment of approx. 350 bp that was obtained by complete digestion of the same plasmid. Ligation of the BstEII fragment alone prior to addition to the vector enhances the insertion of multimeric VHH encoding gene segments. After transformation in *E. coli* TG1 the resulting clones were screened by PCR with M13Rev and M13Fwd primers; since BstEII is an a-symmetric cutter (5 nt overhang) only correctly oriented inserts were obtained as was confirmed by digesting the plasmids with PstI alone (350 bp) or double digesting with EcoRI and HindIII (1000 bp for bivalent (BIV 3E, SEQ ID NO: 73), 1350 bp for trivalent (TRI 3E, SEQ ID NO: 74) and 1700 bp for tetravalent (TETRA 3E, SEQ ID NO: 75), data not shown). The sequences are listed in Table 7.

The clones were grown and induced on 50 ml scale, periplasmic fractions prepared and used for IMAC purification with TALON resin. Analysis of the purified products on Coomassie stained PAGE revealed good production levels (between 2 and 10 mg per liter cell culture) of intact multivalent VHH (see FIG. 11). The molecular appearance of the IMAC purified VHH was determined by gel filtration on a Superdex 75HR column and as expected the molecules with higher avidities came earlier from the column (see FIG. 12).

The antagonistic efficacy was analyzed with the cell based assay using KYM cells. The cells were seeded in microtiter-plates and cultured in the presence or absence of TNF-alpha (1.29 ng/ml or approx. 25 pM of trimer). The assays (FIG. 13) revealed that the monovalent molecules used in this study had the poorest antagonistic characteristics, what is reflected by their 1050 values: the Fab derived from the chimeric antibody Remicade has an 1050 of 2 nM and for VHH#3E it is 12 nM (see also FIG. 3). The avidity of the used molecules turned out to have a dramatic influence on the antagonistic efficacy as was observed with the bivalent IgG molecule Remicade, which is 40-fold more effective (IC50 50 pM) than the Fab. TNF-alpha is a trimeric molecule, which interacts to a dimeric receptor and therefore it can be expected that the avidity of the IgG permits the mutual binding to two epitopes on the cytokine and supports the formation of large complexes as has been described before (Santora et al, Anal. Biochem. 299, 119-129). Surprisingly, increasing the avidity of the VHH from monomer to dimer has a far more spectacular effect than observed with Remicade, since the 1050 of the dimer (30 pM) is 400 fold lower than of the monomer. Increasing the avidity even more leads to a still better antagonistic behaviour: the trimeric VHH has an 1050 of 20 pM and the tetravalent format 6 pM. All higher avidity formats of the VHH are more efficient than Remicade, while the tetravalent format is even better than Enbrel, which consists of the extracellular domain of the receptor p75 fused to the Fc of an IgG and therefore has a bivalent binding mode.

The same unexpected effect of avidity on antagonistic behaviour was observed with VHH generated against mouse TNF (FIG. 14). The same type of cytotoxicity assay was performed using MTT as substrate and mouse TNF-alpha (65 pg/ml or 1.3 pM), but with the murine cell line L929, which expresses the mouse specific receptor. Three different antagonistic (monovalent) VHH were identified coded 9E and 3F, of which the first two have IC50's of 25 nM and the latter 2 nM (see also Example 3). Conversion of 3F into the bivalent format (BIV#m3F, SEQ ID NO: 76) yielded a 1000 fold increase in 1050 (2 pM), thereby demonstrating once more that the increased avidity of the antibody leads to an unexpected improvement of the antagonistic characteristics.

2) Comparison with VHH-Fc Fusion

VHH#3E, directed against human TNF, was cloned via PstI and BstEII in an adapted vector derived from pCDNA3, thereby generating a genetic fusion to the CH1 deleted Fc portion of human IgG1. After confirmation by sequencing, the plasmid construct was transfected to the myeloma cell line NS0. The obtained cell line was grown and the VHH-Fc fusion was secreted into the culture supernatant. The product was purified with an anti-human Fc VHH resin and analyzed on a Coomassie stained gel (FIG. 15). In the presence of DTT the fusion was visible as a 45 kDa protein, in the absence of DTT the dimeric molecule with a molecular weight of 90 kDa could be observed. This dimeric product results from the linkage of two chains by two disulfide bridges, which originate from cysteine residues located in the hinge region.

The VHH-fusion was tested in the bioassay with the human cell line KYM and turned out to be 5-fold less effective than the bivalent VHH in spite of the fact that both molecules have the same avidity and that they both originate from VHH#3E (FIG. 16). Probably steric hindrance by the bulky Fc tail might cause this discrepancy.

Example 5

Calculation of Homologies Between Anti-Target-Single Domain Antibodies of the Invention The degree of amino acid sequence homology between anti-target single domain antibodies of the invention was calculated using the Bioedit Sequence Alignment Editor. The calculations indicate the proportion of identical residues between all of the sequences as they are aligned by ClustalW. (Thompson, J. D., Higgins, D. G. and Gibson, T. J. (1994) CLUSTAL W: improving the sensitivity of progressive multiple sequence alignment through sequence weighting, position specific gap penalties and weight matrix choice. Nucleic Acids Research, submitted, June 1994). Table 8 indicates the fraction homology between anti-serum albumin VHHs of the invention. Table 9 indicates the fraction homology between anti-TNF-alpha VHHs of the invention. Table 10 indicates the percentage homology between anti-IFN-gamma VHHs of the invention.

Example 6

Expression of a VHH-CDR3 Fragment of VHH#3E

The CDR3 region of VHH#3E was amplified by using a sense primer located in the framework 4 region (Forward: CCCCTGGCCCCAGTAGTTATACG) (SEQ ID NO:103) and an anti-sense primer located in the framework 3 region (Reverse: TGTGCAGCAAGAGACGG) (SEQ ID NO:104).

In order to clone the CDR-3 fragment in pAX10, a second round PCR amplification was performed with following primers introducing the required restriction sites:

```
Reverse primer Sfi1:
                                      (SEQ ID NO: 105)
GTCCTCGCAACTGCGGCCCAGCCGGCCTGTGCAGCAAGAGACGG Forward primer Not1:
                                      (SEQ ID NO: 106)
GTCCTCGCAACTGCGCGGCCGCCCCCTGGCCCCAGTAGTTATACG
```

The PCR reactions were performed in 50 ml reaction volume using 50 pmol of each primer. The reaction conditions for the primary PCR were 11 min at 94° C., followed by 30/60/120 sec at 94/55/72° C. for 30 cycles, and 5 min at 72° C. All reaction were performed with 2.5 mM MgCl2, 200 mM dNTP and 1.25 U AmpliTaq God DNA Polymerase (Roche Diagnostics, Brussels, Belgium).

After cleavage with Sfi1 and Not1 the PCR product was cloned in pAX10.

Example 7

Stability Testing of Antibody Fragments Specific for Human TNFα

Orally administered proteins are subject to denaturation at the acidic pH of the stomach and as well to degradation by pepsin. We have selected conditions to study the resistance of the VHH#3E to pepsin which are supposed to mimic the gastric environment. VHH#3E a VHH specific to human TNFα was produced as recombinant protein in E. coli and purified to homogeneity by IMAC and gel filtration chromatography. The protein concentration after purification was determined spectrophotometrically by using the calculated molar extinction coefficient at 280 nm. Diluted solutions at 100 microgram/ml were prepared in McIlvaine buffer (J. Biol. Chem. 49, 1921, 183) at pH 2, pH3 and 4 respectively. These solutions were subsequently incubated for 15 minutes at 37° C., prior the addition of porcine gastric mucosa pepsin at a 1/30 w/w ratio. Sixty minutes after adding the protease a sample was collected and immediately diluted 100-fold in PBS pH7.4 containing 0.1% casein to inactivate the pepsin. Seven additional 3-fold dilutions were prepared from this sample for assessing the presence of functional antibody fragment by ELISA. Identical dilutions prepared from an aliquot collected prior the addition of the protease served as a reference. In the ELISA assay biotinylated TNFα was captured in wells of a microtiter plate coated with neutravidin. For both the pepsin-treated and reference samples similar serial dilutions of the samples were prepared and 100 microliter of those dilutions were added to the wells. After incubation for 1 hour the plates were washed. For the detection of VHH binding to of the captured TNFα a polyclonal rabbit anti-VHH antiserum (R42) and an anti-rabbit IgG alkaline phosphatase conjugate was used. After washing, the plates were developed with paranitrophenyl phosphate. The data plotted in FIG. 17 shows similar curves for all of the samples exposed to digestive conditions as well as for the reference samples. This indicates that the VHH#3E essentially retains its functional activity under all of the chosen conditions.

Example 8

Oral Administration of an Anti-Human TNFα Specific VHH in Mice

An antibody solution containing the anti-human TNFα specific VHH#3E (100 microgram per milliliter in 100-fold diluted PBS) was prepared. Three mice which were first deprived from drinking water for 12 hours and subsequently allowed to freely access the antibody solution during the next two hours. Afterwards the mice were sacrificed and their stomachs were dissected. Immediately the content of the stomachs was collected by flushing the stomach with 500 microliter PBS containing 1% BSA. This flushed material was subsequently used to prepare serial three-fold dilutions, starting at a 1/5 dilution from the undiluted material. One hundred microliter of these samples was transferred to individual wells of a microtiter plate coated with human TNFα. After incubation for 1 hour and following extensive washing the presence of immuno-reactive material was assessed with a polyclonal rabbit anti-VHH antiserum (R42) followed by incubation with an anti-rabbit alkaline-phosphatase conjugate. The ELISA was developed with paranitrophenyl acetate. The ELISA signals obtained after 10 minutes clearly demonstrated the presence of functional VHH#3E in the gastric flushings of these mice. By comparing to the standard curve we determined the concentration of the functional antibody fragment in the gastric flushing fluid to be 1.5, 12.6 and 8.6 microgram/ml for the three mice tested.

Example 9

Efficacy in an Animal Model for IBD

1) Animal Model of Chronic Colitis

The efficacy of bivalent VHH constructs applied via various routes of administration was assessed in a DSS (dextran sodium sulfate) induced model of chronic colitis in BALB/c mice. This model was originally described by Okayasu et al. [Okayasu et al. Gastroenterology 1990; 98: 694-702] and modified by Kojouharoff et. al. [G. Kojouharoff et al. Clin. Exp. Immunol. 1997; 107: 353-8]. The animals were obtained from Charles River Laboratories, Germany, at an age of 11 weeks and kept in the animal facility until they reached a body weight between 21 and 22 g. Chronic colitis was induced in the animals by four DSS treatment cycles. Each cycle consisted of a DSS treatment interval (7 days) where DSS was provided with the drinking water at a concentration of 5% (w/v) and a recovery interval (12 days) with no DSS present in the drinking water. The last recovery period was prolonged from 12 to 21 days to provide for an inflammation status rather representing a chronic than an acute inflammation at the time of the treatment. Subsequent to the last recovery interval the mice were randomly assigned to groups of 8 mice and treatment with the VHH-constructs was started. The treatment interval was 2 weeks. One week after the end of the treatment interval the animals were sacrificed, the intestine was dissected and histologically examined. The experimental setting is shown schematically in FIG. 18.

2) VHH Treatment Schedule

During the VHH treatment period the mice (8 animals per group) were treated daily for 14 consecutive days with bivalent VHH#3F (VHH#m3F-VHH#m3F; SEQ ID No. 76) by intra-gastric or intra-venous application of 100 µg bivalent VHH 3F. An additional group of animals was treated rectally with the bivalent VHH#3F every other day for a period of 14 days. In all treatment groups a dose of 100 µg of the bivalent VHH#3F was applied at a concentration of 1 mg/ml in a buffered solution. The negative control groups received 100 µl of PBS under otherwise identical conditions. The treatment schedule is shown in Table 11.

3) Results

After the mice were sacrificed the body weight was determined and the colon was dissected. The length of the dissected colon was determined and the histology of the colon was assessed by Haematoxilin-Eosin (HE) stain (standard conditions). As compared to the negative controls (PBS treatment) the groups treated with bivalent nanobody 3F showed a prorogued colon length as well as an improved histological score [G. Kojouharoff et al. Clin. Exp. Immunol. 1997; 107: 353-8] thereby demonstrating efficacy of the treatment.

TABLE 1

Amino acid sequence listing of the peptides of aspects of present invention directed against TNF-alpha.

| NAME | SEQ ID NO | SEQUENCE |
|---|---|---|
| VHH#1A | 1 | QVQLQESGGGLVQPGGSLRLSCATSGFDFSVSWMYWVRQAPGKGLEWVS EINTNGLITKYVDSVKGRFTISRDNAKNTLYLQMDSLIPEDTALYYCAR SPSGSFRGQGTQVTVSS |
| VHH#7B | 2 | QVQLQESGGGLVQPGGSLRLSCAASGSIFRVNAMGWYRQVPGNQREFVA IITSGDNLNYADAVKGRFTISTDNVKKTVYLQMNVLKPEDTAVYYCNAI LQTSRWSIPSNYWGQGTQVTVSS |

TABLE 1-continued

Amino acid sequence listing of the peptides of aspects of present invention directed against TNF-alpha.

| NAME | SEQ ID NO | SEQUENCE |
|---|---|---|
| VHH#2B | 3 | QVQLQESGGGLVQPGGSLRLSCATSGFTFSDYWMYWVRQAPGKGLEWVSTVNTNGLITRYADSVKGRFTISRDNAKYTLYLQMNSLKSEDTAVYYCTKVVPPYSDDSRTNADWGQGTQVTVSS |
| VHH#3E | 4 | QVQLQESGGGLVQPGGSLRLSCAASGRTFSDHSGYTYTIGWFRQAPGKEREFVARIYWSSGNTYYADSVKGRFAISRDIAKNTVDLTMNNLEPEDTAVYYCAARDGIPTSRSVESYNYWGQGTQVTVSS |
| VHH#3G | 5 | QVQLQDSGGGLVQAGGSLRLSCAVSGRTFSAHSVYTMGWFRQAPGKEREFVARIYWSSANTYYADSVKGRFTISRDNAKNTVDLLMNSLKPEDTAVYYCAARDGIPTSRTVGSYNYWGQGTQVTVSS |
| VHH#10A | 6 | QVQLQESGGGLVQPGGSLRLSCAASGSIFRVNAMGWYRQVPGNQREFVAIITSSDTNDTTNYADAVKGRFTISTDNVKKTVYLQMNVLKPEDTAVYYCNAVLQTSRWSIPSNYWGQGTQVTVSS |
| VHH#2G | 7 | QVQLQDSGGGLVQAGGSLRLSCTTSGRTISVYAMGWFRQAPGKEREFVASISGSGAITPYADSVKGRFTISRDNAKNTVYLQMNSLNPEDTAVYYCAASRYARYRDVHAYDYWGQGTQVTVSS |
| VHH#1F | 8 | QVQLQDSGGGLVQAGGSLRLSCAASTRTFSRYVVGWFRQAPGKEREFVATISWNGEHTYYADSVKGRYTISRDNAKNTVYLQMGSLKPEDTAVYYCAARSFWGYNVEQRDFGSWGQGTPVTVSS |
| VHH#9C | 9 | QVQLQESGGGLVQPGGSLRLSCAASGSIFRVNAMGWYRQVPGNQREFVAIITNDTTNYADAVKGRFTISTDNVKKTVYLQMNVLKPEDTAVYYCNTVLQTSRWNIPTNYWGQGTQVTVSS |
| VHH#11E | 10 | QVQLQESGGGLVQPGGSLRLSCAASGSIFRVNAMGWYRQVPGNQREFVAIISGDTTNYADAVKGRFTISTDNVKKTVYLQMNVLESEDTAVYYCNAVLQTSRWSIPSNYWGQGTQVTVSS |
| VHH#10C | 11 | QVQLQDSGGGLVQPGGSLRLACVASGSIFSIDVMGWYRQAPGQQRELVATITNSWTTNYADSVKGRFTISRDNAKNVVYLQMNSLKLEDTAVYYCNARRWYQPEAWGQGTQVTVSS |
| VHH#4B | 12 | QVQLQDSGGGLVQPGGSLRLSCAASGFTFSTHWMYWVRQAPGKGLEWVSTINTNGLITDYIHSVKGRFTISRDNAKNTLYLQMNSLKSEDTAVYYCALNQAGLSRGQGTQVTVSS |
| VHH#10D | 13 | QVQLQESGGGLVQAGGSLRLSCAASRRTFSGYAMGWFRQAPGKEREFVAVVSGTGTIAYYADSVKGRFTISRDNAENTVYLQMNSLKPEDTGLYYCAVGPSSSRWYYRGASLVDYWGKGTLVTVSS |
| VHH#12B | 14 | QVQLQESGGGLVQPGGSLRLSCAASGFEFENHWMYWVRQAPGKGLEWVSTVNTNGLITRYADSVKGRFTISRDNAKYTLYLQMNSLKSEDTAVYYCTKVLPPYSDDSRTNADWGQGTQVTVSS |
| VHH#m9A | 79 | EVQLVESGGGLVQAGGSLRLSCAASGGTLSSYITGWFRQAPGKEREFVGAVSWSSSTIVYADSVEGRFTISRDNHQNTVYLQMDSLKPEDTAVYYCAARPYQKYNWASASYNVWGQGTQVTVSS |
| VHH#m9E | 15 | EVQLVESGGGLVQAGGSLRLSCAASGGTLSSYITGWFRQAPGKEREFVGAVSWSSSTIVYADSVEGRFTISRDNHQNTVYLQMDSLKPEDTAVYYCAARPYQKYNWASASYNVWGQGTQVTVSS |
| VHH#m3F | 16 | QVQLQDSGGGLVQAGGSLRLSCAASGGTFSSIIMAWFRQAPGKEREFVGAVSWSGGTTVYADSVLGRFEISRDSARKSVYLQMNSLKPEDTAVYYCAARPYQKYNWASASYNVWGQGTQVTVSS |
| VHH#m4B | 80 | QVQLQDSGGGLVQAGGSLRLSCGVSGLSFSGYTMGWFRQAPGKEREFAAAIGWNSGTTEYRNSVKGRFTISRDNAKNTVYLQMNSLKPEDTAVYYCAASPKYMTAYERSYDFWGQGTQVTVSS |
| VHH#8-29 | 81 | QVQLVESGGGLVQPGGSLRLSCAASGFAFGDSWMYWVRQAPGKGLEWVSEINTNGLITKYKDSVTGRFTISRDNAKNTLHLEMNRLKPEDTALYYCARDPSGKLRGPGTQVTVSS |
| VHH#8-41 | 82 | QVQLVESGGGLVQPGGPLRLSCAASGFAFGDSWMYWVRQAPGKGLEWVSEINTNGLITKYKDSVTGRFTISRDNAKNTLHLEMNRLKPEDTALYYCARDPSGKLRGPGTQVTVSS |

TABLE 1-continued

Amino acid sequence listing of the peptides of aspects of present invention directed against TNF-alpha.

| NAME | SEQ ID NO | SEQUENCE |
|---|---|---|
| VHH#8-42 | 83 | QVQLVESGGGLVQPGGSLRLSCAASGFAFGDSWMYWVRQAPGKGLEWVS EINTNGLITKYKDSVTGRFTISRDNAKNTLHLEMNRLKPEDTALYYCAR DPSGKLRGPGTQVTVSS |
| VHH#8-44 | 84 | QVQLVESGGGLVQPGGSLRLSCAASGFTFSDHWMYWVRQAPGKGLEWVS TINTNGLITNYIHSVKGRFTISRDNAKNTLYLQMNSLKSEDTAVYYCAL NQAGLSRGQGTQVTVSS |

TABLE 2

List of mutagenesis reactions, mutagenic primers and templates used for mutagenesis of VHH#12B

| Mutation | Template | Primer sequence |
|---|---|---|
| A74S + Y76N + K83R + P84A | Wild type | 5'-AGA GAC AAC TCC AAG AAC ACG CTG TAT CTG CAA ATG AAC AGC CTG AGA GCT GAG GAC ACG-3' <br> Arg Asp Asn Ser Lys Asn Thr Leu Tyr Leu Gln Met Asn Ser Leu Arg Ala Glu Asp Thr |
| Q1E + Q5L + A74S + Y76N + K83R + P84A | A74S + Y76N + K83R + P84A | 5'-C ATG GCT GAG GTG CAG CTG CTC GAG TCT GG-3' <br> Met Ala Glu Val Gln Leu Leu Glu Ser |
| Q1E + Q5L + A74S + Y76N + K83R + P84A + T93A | Q1E + Q5L + A74S + Y76N + K83R + P84A | 5'-G GAC ACG GCC GTC TAT TAC TGT GCA AAA GTA CTT C-3' <br> Asp Thr Ala Val Tyr Tyr Cys Ala Lys Val Leu |

TABLE 3

List of mutagenesis reactions, mutagenic primers and templates used for mutagenesis of VHH#3E

| Mutation | Template | Primer sequence |
|---|---|---|
| F37V | Wild type | 5'-ACC TAT ACC ATT GGC TGG GTC CGC CAG GCT-3' <br> Thr Tyr Thr Ile Gly Trp Val Arg Gln Ala |
| E44G | Wild type | 5'-CGC CAG GCT CCA GGG AAG GGG CGT GAG TTT-3' <br> Arg Gln Ala Pro Gly Lys Gly Arg Glu Phe |
| R45L | Wild type | 5'-A GGG AAG GAG CTT GAG TTT GTA GCG CGT AT-3' <br> Gly Lys Glu Leu Glu Phe Val Ala Arg |
| F47W | Wild type | 5'-A GGG AAG GAG CGT GAG TGG GTA GCG CGT AT-3' <br> Gly Lys Glu Arg Glu Trp Val Ala Arg |

TABLE 4

Overview of humanized and wild type anti-TNF-alpha VHH

| SEQ ID | Name | Sequence |
|---|---|---|
| 17 | VHH#12B A74S + Y76N + K83R + P84A | QVQLQESGGGLVQPGGSLRLSCAASGFEFENHWMYWVRQAPGKGLEW VSTVNTNGLITRYADSVKGRFTISRDNSKNTLYLQMNSLRAEDTAVY YCTKVLPPYSDDSRTNADWGQGTQVTVSS |
| 18 | VHH#12B Q1E + Q5L + A74S + Y76N + K83R + P84A | EVQLLESGGGLVQPGGSLRLSCAASGFEFENHWMYWVRQAPGKGLEW VSTVNTNGLITRYADSVKGRFTISRDNSKNTLYLQMNSLRAEDTAVY YCTKVLPPYSDDSRTNADWGQGTQVTVSS |
| 19 | VHH#12B Q1E + Q5L + A74S + Y76N + K83R + P84A + T93A | EVQLLESGGGLVQPGGSLRLSCAASGFEFENHWMYWVRQAPGKGLEW VSTVNTNGLITRYADSVKGRFTISRDNSKNTLYLQMNSLRAEDTAVY YCAKVLPPYSDDSRTNADWGQGTQVTVSS |
| 20 | VHH#12B Wild type | QVQLQESGGGLVQPGGSLRLSCAASGFEFENHWMYWVRQAPGKGLEW VSTVNTNGLITRYADSVKGRFTISRDNAKYTLYLQMNSLKSEDTAVY YCTKVLPPYSDDSRTNADWGQGTQVTVSS |
| 21 | VHH#3E F37V | QVQLQESGGGLVQPGGSLRLSCAASGRTFSDHSGYTYTIGWVRQAPG KEREFVARIYWSSGNTYYADSVKGRFAISRDIAKNTVDLTMNNLEPE DTAVYYCAARDGIPTSRSVESYNYWGQGTQVTVSS |

TABLE 4-continued

Overview of humanized and wild type anti-TNF-alpha VHH

| SEQ ID | Name | Sequence |
|---|---|---|
| 22 | VHH#3E E44G | QVQLQESGGGLVQPGGSLRLSCAASGRTFSDHSGYTYTIGWFRQAPG KGREFVARIYWSSGNTYYADSVKGRFAISRDIAKNTVDLTMNNLEPE DTAVYYCAARDGIPTSRSVESYNYWG QGTQVTVSS |
| 23 | VHH#3E R45L | QVQLQESGGGLVQPGGSLRLSCAASGRTFSDHSGYTYTIGWFRQAPG KELEFVARIYWSSGNTYYADSVKGRFAISRDIAKNTVDLTMNNLEPE DTAVYYCAARDGIPTSRSVESYNYWGQGTQVTVSS |
| 24 | VHH#3E F47W | QVQLQESGGGLVQPGGSLRLSCAASGRTFSDHSGYTYTIGWFRQAPG KEREWVARIYWSSGNTYYADSVKGRFAISRDIAKNTVDLTMNNLEPE DTAVYYCAARDGIPTSRSVESYNYWGQGTQVTVSS |
| 25 | VHH#3E Wild type | QVQLQESGGGLVQPGGSLRLSCAASGRTFSDHSGYTYTIGWFRQAPG KEREFVARIYWSSGNTYYADSVKGRFAISRDIAKNTVDLTMNNLEPE DTAVYYCAARDGIPTSRSVESYNYWGQGTQVTVSS |

TABLE 5

Anti-mouse serum albumin, and anti-mouse serum albumin + anti TNF-alpha VHH

| Name | SEQ ID | Sequence |
|---|---|---|
| | | Anti-mouse serum albumin |
| MSA21 | 26 | QVQLQESGGGLVQPGGSLRLSCEASGFTFSRFGMTWVRQAPGKGVEWV SGISSLGDSTLYADSVKGRFTISRDNAKNTLYLQMNSLKPEDTAVYYC TIGGSLNPGGQGTQVTVSS |
| MSA24 | 27 | QVQLQESGGGLVQPGNSLRLSCAASGFTFRNFGMSWVRQAPGKEPEWV SSISGSGSNTIYADSVKDRFTISRDNAKSTLYLQMNSLKPEDTAVYYC TIGGSLSRSSQGTQVTVSS |
| MSA210 | 28 | QVQLQESGGGLVQPGGSLRLTCTASGFTFSSFGMSWVRQAPGKGLEWV SAISSDSGTKNYADSVKGRFTISRDNAKKMLFLQMNSLRPEDTAVYYC VIGRGSPSSQGTQVTVSS |
| MSA212 | 29 | QVQLQESGGGLVQPGGSLRLTCTASGFTFRSFGMSWVRQAPGKGLEWV SAISADGSDKRYADSVKGRFTISRDNGKKMLTLDMNSLKPEDTAVYYC VIGRGSPASQGTQVTVSS |
| MSAc16 | 85 | AVQLVESGGGLVQAGDSLRLSCVVSGTTFSSAAMGWFRQAPGKEREFV GAIKWSGTSTYYTDSVKGRFTISRDNVKNTVYLQMNNLKPEDTGVYTC AADRDRYRDRMGPMTTTDFRFWGQGTQVTVSS |
| MSAc112 | 86 | QVKLEESGGGLVQTGGSLRLSCAASGRTFSSFAMGWFRQAPGREREFV ASIGSSGITTNYADSVKGRFTISRDNAKNTVYLQMNSLKPEDTGLCYC AVNRYGIPYRSGTQYQNWGQGTQVTVSS |
| MSAc110 | 87 | EVQLEESGGGLVQPGGSLRLSCAASGLTFNDYAMGWYRQAPGKERDMV ATISIGGRTYYADSVKGRFTISRDNAKNTVYLQMNSLKPEDTAIYYCV AHRQTVVRGPYLLWGQGTQVTVSS |
| MSAc114 | 88 | QVQLVESGGKLVQAGGSLRLSCAASGRTFSNYAMGWFRQAPGKEREFV AGSGRSNSYNYYSDSVKGRFTISRDNAKNTVYLQMNSLKPEDTAVYYC AASTNLWPRDRNLYAYWGQGTQVTVSS |
| MSAc116 | 89 | EVQLVESGGGLVQAGDSLRLSCAASGRSLGIYRMGWFRQVPGKEREFV AAISWSGGTTRYLDSVKGRFTISRDSTKNAVYLQMNSLKPEDTAVYYC AVDSSGRLYWTLSTSYDYWGQGTQVTVSS |
| MSAc119 | 90 | QVQLVEFGGGLVQAGDSLRLSCAASGRSLGIYKMAWFRQVPGKEREFV AAISWSGGTTRYIDSVKGRFTLSRDNTKNMVYLQMNSLKPDDTAVYYC AVDSSGRLYWTLSTSYDYWGQGTQVTVSS |
| MSAc15 | 91 | EVQLVESGGGLVQAGGSLSLSCAASGRTFSPYTMGWFRQAPGKEREFL AGVTWSGSSTFYGDSVKGRFTASRDSAKNTVTLEMNSLNPEDTAVYYC AAAYGGGLYRDPRSYDYWGRGTQVTVSS |

TABLE 5-continued

Anti-mouse serum albumin, and anti-mouse serum albumin + anti TNF-alpha VHH

| Name | SEQ ID | Sequence |
|------|--------|----------|
| MSc111 | 92 | AVQLVESGGGLVQAGGSLRLSCAASGFTLDAWPIAWFRQAPGKEREGV<br>SCIRDGTTYYADSVKGRFTISSDNANNTVYLQTNSLKPEDTAVYYCAA<br>PSGPATGSSHTFGIYWNLRDDYDNWGQGTQVTVSS |
| MSAc115 | 93 | EVQLVESGGGLVQAGGSLRLSCAASGFTFDHYTIGWFRQVPGKEREGV<br>SCISSSDGSTYYADSVKGRFTISSDNAKNTVYLQMNTLEPDDTAVYYC<br>AAGGLLLRVEELQASDYDYWGQGIQVTVSS |
| MSAc18 | 94 | AVQLVDSGGGLVQPGGSLRLSCTASGFTLDYYAIGWFRQAPGKEREGV<br>ACISNSDGSTYYGDSVKGRFTISRDNAKTTVYLQMNSLKPEDTAVYYC<br>ATADRHYSASHHPFADFAFNSWGQGTQVTVSS |
| MSAc17 | 95 | EVQLVESGGGLVQAGGSLRLSCAAYGLTFWRAAMAWFRRAPGKERELV<br>VARNWGDGSTRYADSVKGRFTISRDNAKNTVYLQMNSLKPEDTAVYYC<br>AAVRTYGSATYDIWGQGTQVTVSS |
| MSAc120 | 96 | EVQLVESGGGLVQDGGSLRLSCIFSGRTFANYAMGWFRQAPGKEREFV<br>AAINRNGGTTNYADALKGRFTISRDNTKNTAFLQMNSLKPDDTAVYYC<br>AAREWPFSTIPSGWRYWGQGTQVTVSS |
| MSAc14 | 97 | DVQLVESGGGWVQPGGSLRLSCAASGPTASSHAIGWFRQAPGKEREFV<br>VGINRGGVTRDYADSVKGRFAVSRDNVKNTVYLQMNRLKPEDSAIYIC<br>AARPEYSFTAMSKGDMDYWGKGTLVTVSS |

Anti-mouse serum albumin/anti TNF-alpha

| Name | SEQ ID | Sequence |
|------|--------|----------|
| MSA21/<br>VHH#3E | 30 | QVQLQESGGGLVQPGGSLRLSCEASGFTFSRFGMTWVRQAPGKGVEWV<br>SGISSLGDSTLYADSVKGRFTISRDNAKNTLYLQMNSLKPEDTAVYYC<br>TIGGSLNPGGQGTQVTVSSEPKTPKPQPAAAQVQLQESGGGLVQPGGS<br>LRLSCAASGRTFSDHSGYTYTIGWFRQAPGKEREFVARIYWSSGNTYY<br>ADSVKGRFAISRDIAKNTVDLTMNNLEPEDTAVYYCAARDGIPTSRSV<br>ESYNYWGQGTQVTVSS |
| MSA24/<br>VHH#3E | 31 | QVQLQESGGGLVQPGNSLRLSCAASGFTFRNFGMSWVRQAPGKEPEWV<br>SSISGSGSNTIYADSVKDRFTISRDNAKSTLYLQMNSLKPEDTAVYYC<br>TIGGSLSRSSQGTQVTVSSEPKTPKPQPAAAQVQLQESGGGLVQPGGS<br>LRLSCAASGRTFSDHSGYTYTIGWFRQAPGKEREFVARIYWSSGNTYY<br>ADSVKGRFAISRDIAKNTVDLTMNNLEPEDTAVYYCAARDGIPTSRSV<br>ESYNYWGQGTQVTVSS |
| MSA210/<br>VHH#3E | 32 | QVQLQESGGGLVQPGGSLRLTCTASGFTFSSFGMSWVRQAPGKGLEWV<br>SAISSDSGTKNYADSVKGRFTISRDNAKKMLFLQMNSLRPEDTAVYYC<br>VIGRGSPSSQGTQVTVSSEPKTPKPQPAAAQVQLQESGGGLVQPGGSL<br>RLSCAASGRTFSDHSGYTYTIGWFRQAPGKEREFVARIYWSSGNTYYA<br>DSVKGRFAISRDIAKNTVDLTMNNLEPEDTAVYYCAARDGIPTSRSVE<br>SYNYWGQGTQVTVSS |
| MSA212/<br>VHH#3E | 33 | QVQLQESGGGLVQPGGSLRLTCTASGFTFRSFGMSWVRQAPGKGLEWV<br>SAISADGSDKRYADSVKGRFTISRDNGKKMLTLDMNSLKPEDTAVYYC<br>VIGRGSPASQGTQVTVSSEPKTPKPQPAAAQVQLQESGGGLVQPGGSL<br>RLSCAASGRTFSDHSGYTYTIGWFRQAPGKEREFVARIYWSSGNTYYA<br>DSVKGRFAISRDIAKNTVDLTMNNLEPEDTAVYYCAARDGIPTSRSVE<br>SYNYWGQGTQVTVSS |
| MSA21/<br>MSA21/<br>VHH#3E | 34 | QVQLQESGGGLVQPGGSLRLSCEASGFTFSRFGMTWVRQAPGKGVEWV<br>SGISSLGDSTLYADSVKGRFTISRDNAKNTLYLQMNSLKPEDTAVYYC<br>TIGGSLNPGGQGTQVTVSSEPKTPKPQPAAAQVQLQESGGGLVQPGGS<br>LRLSCEASGFTFSRFGMTWVRQAPGKGVEWVSGISSLGDSTLYADSVK<br>GRFTISRDNAKNTLYLQMNSLKPEDTAVYYCTIGGSLNPGGQGTQVTV<br>SSEPKTPKPQPAAAQVQLQESGGGLVQPGGSLRLSCAASGRTFSDHSG<br>YTYTIGWFRQAPGKEREFVARIYWSSGNTYYADSVKGRFAISRDIAKN<br>TVDLTMNNLEPEDTAVYYCAARDGIPTSRSVESYNYWGQGTQVTVSS |
| MSA210/<br>VHH#1A | 35 | QVQLQESGGGLVQPGGSLRLTCTASGFTFSSFGMSWVRQAPGKGLEWV<br>SAISSDSGTKNYADSVKGRFTISRDNAKKMLFLQMNSLRPEDTAVYYC<br>VIGRGSPSSQGTQVTVSSEPKTPKPQPAAAQVQLQESGGGLVQPGGSL<br>RLSCATSGFDFSVSWMYWVRQAPGKGLEWVSEINTNGLITKYVDSVKG<br>RFTISRDNAKNTLYLQMDSLIPEDTALYYCARSPSGSFRGQGTQVTVS<br>S |
| MSA210/<br>VHH#7B | 36 | QVQLQESGGGLVQPGGSLRLTCTASGFTFSSFGMSWVRQAPGKGLEWV<br>SAISSDSGTKNYADSVKGRFTISRDNAKKMLFLQMNSLRPEDTAVYYC<br>VIGRGSPSSQGTQVTVSSEPKTPKPQPAAAQVQLQESGGGLVQPGGSL |

TABLE 5-continued

Anti-mouse serum albumin, and anti-mouse serum albumin + anti TNF-alpha VHH

| Name | SEQ ID | Sequence |
|---|---|---|
| | | RLSCAASGSIFRVNAMGWYRQVPGNQREFVAIITSGDNLNYADAVKGR FTISTDNVKKTVYLQMNVLKPEDTAVYYCNAILQTSRWSIPSNYWGQG TQVTVSS |
| MSA210/ VHH#2B | 37 | QVQLQESGGGLVQPGGSLRLTCTASGFTFSSFGMSWVRQAPGKGLEWV SAISSDSGTKNYADSVKGRFTISRDNAKKMLFLQMNSLRPEDTAVYYC VIGRGSPSSQGTQVTVSSEPKTPKPQPAAAQVQLQESGGGLVQPGGSL RLSCATSGFTFSDYWMYWVRQAPGKGLEWVSTVNTNGLITRYADSVKG RFTISRDNAKYTLYLQMNSLKSEDTAVYYCTKVVPPYSDDSRTNADWG QGTQVTVSS |
| MSA210/ VHH#3E | 38 | QVQLQESGGGLVQPGGSLRLTCTASGFTFSSFGMSWVRQAPGKGLEWV SAISSDSGTKNYADSVKGRFTISRDNAKKMLFLQMNSLRPEDTAVYYC VIGRGSPSSQGTQVTVSSEPKTPKPQPAAAQVQLQESGGGLVQPGGSL RLSCAASGRTFSDHSGYTYTIGWFRQAPGKEREFVARIYWSSGNTYYA DSVKGRFAISRDIAKNTVDLTMNNLEPEDTAVYYCAARDGIPTSRSVE SYNYWGQGTQVTVSS |
| MSA210/ VHH#3G | 39 | QVQLQESGGGLVQPGGSLRLTCTASGFTFSSFGMSWVRQAPGKGLEWV SAISSDSGTKNYADSVKGRFTISRDNAKKMLFLQMNSLRPEDTAVYYC VIGRGSPSSQGTQVTVSSEPKTPKPQPAAAQVQLQDSGGGLVQAGGSL RLSCAVSGRTFSAHSVYTMGWFRQAPGKEREFVARIYWSSANTYYADS VKGRFTISRDNAKNTVDLLMNSLKPEDTAVYYCAARDGIPTSRTVGSY NYWGQGTQVTVSS |
| MSA21/ VHH#12B | 40 | QVQLQESGGGLVQPGGSLRLSCEASGFTFSRFGMTWVRQAPGKGVEWV SGISSLGDSTLYADSVKGRFTISRDNAKNTLYLQMNSLKPEDTAVYYC TIGGSLNPGGQGTQVTVSSEPKTPKPQPAAAQVQLQESGGGLVQPGGS LRLSCAASGFEFENHWMYWVRQAPGKGLEWVSTVNTNGLITRYADSVK GRFTISRDNAKYTLYLQMNSLKSEDTAVYYCTKVLPPYSDDSRTNADW GQGTQVTVSS |
| MSA24/ VHH#12B | 41 | QVQLQESGGGLVQPGNSLRLSCAASGFTFRNFGMSWVRQAPGKEPEWV SSISGSGSNTIYADSVKDRFTISRDNAKSTLYLQMNSLKPEDTAVYYC TIGGSLSRSSQGTQVTVSS<u>EPKTPKPQPAAA</u>QVQLQESGGGLVQPGGS LRLSCAASGFEFENHWMYWVRQAPGKGLEWVSTVNTNGLITRYADSVK GRFTISRDNAKYTLYLQMNSLKSEDTAVYYCTKVLPPYSDDSRTNADW GQGTQVTVSS |
| MSA210/ VHH#12B | 42 | QVQLQESGGGLVQPGGSLRLTCTASGFTFSSFGMSWVRQAPGKGLEWV SAISSDSGTKNYADSVKGRFTISRDNAKKMLFLQMNSLRPEDTAVYYC VIGRGSPSSQGTQVTVSS<u>EPKTPKPQPAAA</u>QVQLQESGGGLVQPGGSL RLSCAASGFEFENHWMYWVRQAPGKGLEWVSTVNTNGLITRYADSVKG RFTISRDNAKYTLYLQMNSLKSEDTAVYYCTKVLPPYSDDSRTNADWG QGTQVTVSS |
| MSA212/ VHH#12B | 43 | QVQLQESGGGLVQPGGSLRLTCTASGFTFRSFGMSWVRQAPGKGLEWV SAISADGSDKRYADSVKGRFTISRDNGKKMLTLDMNSLKPEDTAVYYC VIGRGSPASQGTQVTVSS<u>EPKTPKPQPAAA</u>QVQLQESGGGLVQPGGSL RLSCAASGFEFENHWMYWVRQAPGKGLEWVSTVNTNGLITRYADSVKG RFTISRDNAKYTLYLQMNSLKSEDTAVYYCTKVLPPYSDDSRTNADWG QGTQVTVSS |

TABLE 6

Amino acid sequence listing of VHH's directed against human IFN-gamma.

| Seq. Family | Name | Seq. Id | Sequence |
|---|---|---|---|
| 1 | MP3D2SRA | 44 | QVQLQDSGGGTVQAGGSLRLSCAASGRTFSDYAVGWFRQA PGKEREFVARILWTGASRSYANSVDGRFTVSTDNAKNTVY LQMNSLKPEDTAIYYCAALPSNIITTDYLRVYYWGQGTQV TVSS |
| 1 | MP3A3SR | 45 | QVQLQDSGGGTVQAGGSLRLSCAASGRTFSNYAVGWFRQA PGKEREFVARIKWSGGRSYANSVDGRFTVSTDNAKNTVY LQMNSLKPEDTAIYYCA?LPSNIITTDYLRVYYWGQGTQV TVSS |

TABLE 6-continued

Amino acid sequence listing of VHH's directed against human IFN-gamma.

| Seq. Family | Name | Seq. Id | Sequence |
|---|---|---|---|
| 2 | MP3C5SR | 46 | QVQLQESGGGLVQAGGSLRLSCAAAGISGSVFSRTPMGWYRQAPGKQRELVAGILTSGATSYAESVKGRFTISRDNAKNTVYLQMNSLSPEDTAEYYCNTYPTWVLSWGQGTQVTSS |
| 2 | MP3C1SR | 47 | QVQLQDSGGGLVQAGGSLRLSCAAAGISGSVFSRTPMGWYRQAPGKQRELVAGILSSGATVYAESVKGRFTISRDNAKNTVYLQMNSLSPEDTAEYYCNTYPTWVLSWGQGTQVTSS |
| 2 | MP3G8SR | 48 | QVQLQESGGGLVQAGGSLRLSCAAAGISGSVFSRTPMGWYRQAPGKQRELVAGILSSGATAYAESVKGRFTISRDNAKNTVYLQMNSLSPEDTAEYYCNTYPTWVLSWGQGTQVTSS |
| 3 | MP3D2BR | 49 | QVQLQESGGGLVQPGESLRLSCAASRGIFRFNAGGWYRQAPGKQRELVAFIGVDNTTRYIDSVKGRFTISRDNAKTTVYLQMNSLQPEDTAVYYCNKVPYIDWGQGTQVTVSS |
| 4 | MP3H6SRA | 50 | QVQLQESGGGLVQAGGSLRLSCAASGRTFSTYNMGWFRQAPGKEREFVAGISWNGGSIYYTSSVEGRFTISRDNAENTVYLQMNSLKPEDTGVYYCASKGRPYGVPSPRQGDYDYWGQGTQVTVSS |
| 4 | MP3B4SRA | 51 | QVQLQESGGGLVQAGGSLRLSCAASGRTFSTYNMGWFRQAPGKEREFVAGISWNGGSIYYTSSVEGRFTISRDNAENTVYLQMNSLKPEDTGVYYCASKGRPYGVPSPRQGDYDYWGQGTQVTVSS |
| 4 | MP4E4BR | 52 | QVQLQESGGGLVQAGGSLRLSCAASGRTFSIYNMGWFRQAPGKEREFVAAISWNGGSIYYTSSVEGRFTISRDNAINTVYLQMNSLKPEDTGVYYCASKGRPYGVPSPRQGEYDYWGQGTQVTVSS |
| 4 | MP4H8SR | 53 | QVQLQESGGGLVQAGGSLRLSCAASGRTFNIYNMGWFRQAPGKERDFVAAISWNGGSIYYTSSVEGRFTISRDNAENTVYLQMNSLKPEDTGVYYCASKGRPYGVPSPRQGDYDYWGQGTQVTVSS |
| 5 | MP2F6SR | 54 | QVKLEESGGGLVQAGGSLRLSCAASGRTFNNYNMGWFRQAPGKEREFVAAISWNGGSTYYDDSVKGRFTISRDNANNLVYLQMNSLNFEDTAVYYCACAANPYGIPQYRENRYDFWGQGTQVTVSS |
| 5 | MP3D1BR | 55 | QVQLQESGGGLVQAGGSLRLSCAASGRTFDNYNMGWFRQAPGKEREFVAAISWNGGSTYYDDSVKGRFTISRDNFQKLVYLQMNSLKLEDTAVYYCACAANPYGIPQYRENRYDFWGQGTQVTVSS |
| 6 | MP2B5BR | 56 | QVQLVESGGRLVQAGGSLRLSCIASGRTISDYAAGWFRQAPGKEREFLASVTWGFGSTSYADSVKGRFTISRDKAKDTVYLQMNTLEPDDTSVYYCASSPRYCAGYRCYVTASEFDSWGQGTQVTVSS |
| 6 | MP2C1BR | 57 | QVKLEESGGRLVQAGGSLRLSCIASGRTISDYAAGWFRQAPGKEREFLASVSWGFGSTYYADSVKGRFTISRDTAKDTVYLQMNTLEPDDTSVYYCASSPRYCAGYRCYATASEFDSWGQGTQVTVSS |
| 6 | MP4A12SR | 58 | QVQLQESGGRLVQAGGSLRLSCIASGRTISDYAAGWFRQAPGKEREFLASVTWGFGSTYYADSVKGRFTISRDKAKDTVYLQMNTLEPDDTSAYYCASSPRYCAGYRCYVTASEFDSWGPGTQVTVSS |
| 7 | MP3F4SRA | 59 | QVQLQDSGGGLVQAGDSLRLSCAASGRSFSSYGMGWFRQAPGKEHEFVAGIWRSGVSLYYTDSVKGRFTISRDDAKMTVSLQMNSLKPEDTAVYYCAAEATFPTWSRGRFADYDRGQGTQVTVSS |
| 7 | MP3D3BR | 60 | QVQLQESGGGLVQAGDSLRLSCTASGRSFSSYGMGWFRQAPGKDHEFVAGIWRSGVSLYYADSVKGRFTISRDDAKMTVSLQMNGLKPEDTAVYYCAAEATFPTWNRGTFADYDRGQGTQVTVSS |
| 7 | MP3E5BR | 61 | QVQLQESGGGLVQAGDSLRLSCAASGRSFSSYGMGWFRQAPGKEHEFVAGIWRSGVSLYYADSVKGRFTISRDDAKMTVS |

TABLE 6-continued

Amino acid sequence listing of VHH's directed against human IFN-gamma.

| Seq. Family | Name | Seq. Id | Sequence |
|---|---|---|---|
| | | | LQMNGLKPEDTAVYYCAAEATFPTWNRGSFADYDYRGQGT TABLE 7-continued Sequences of bivalent (BIV 3E, BIV#m3F), trivalent (TRI3E) or tetravalent (TETRA 3E) VHH directed against TNF-alpha.

| Name | SEQ ID | Sequence |
|---|---|---|
| | | RSVESYNYWGQGTQVTSS<u>EPKTPKPQPAAA</u>QVQLQESGGGLVQPGGSLRLSCAA<br>SGRTFSDHSGYTYTIGWFRQAPGKEREFVARIYWSSGNTYYADSVKGRFAISRDI<br>AKNTVDLTMNNLEPEDTAVYYCAARDGIPTSRSVESYNYWGQGTQVTSS<u>EPKTP</u><br><u>KPQPAAA</u>QVQLQESGGGLVQPGGSLRLSCAASGRTFSDHSGYTYTIGWFRQAPGK<br>EREFVARIYWSSGNTYYADSVKGRFAISRDIAKNTVDLTMNNLEPEDTAVYYCAA<br>RDGIPTSRSVESYNYWGQGTQVTSS |
| TETRA 3E | 75 | QVQLQESGGGLVQPGGSLRLSCAASGRTFSDHSGYTYTIGWFRQAPGKEREFVAR<br>IYWSSGNTYYADSVKGRFAISRDIAKNTVDLTMNNLEPEDTAVYYCAARDGIPTS<br>RSVESYNYWGQGTQVTSS<u>EPKTPKPQPAAA</u>QVQLQESGGGLVQPGGSLRLSCAA<br>SGRTFSDHSGYTYTIGWFRQAPGKEREFVARIYWSSGNTYYADSVKGRFAISRDI<br>AKNTVDLTMNNLEPEDTAVYYCAARDGIPTSRSVESYNYWGQGTQVTSS<u>EPKTP</u><br><u>KPQPAAA</u>QVQLQESGGGLVQPGGSLRLSCAASGRTFSDHSGYTYTIGWFRQAPGK<br>EREFVARIYWSSGNTYYADSVKGRFAISRDIAKNTVDLTMNNLEPEDTAVYYCAA<br>RDGIPTSRSVESYNYWGQGTQVTSS<u>EPKTPKPQPAAA</u>QVQLQESGGGLVQPGGS<br>LRLSCAASGRTFSDHSGYTYTIGWFRQAPGKEREFVARIYWSSGNTYYADSVKGR<br>FAISRDIAKNTVDLTMNNLEPEDTAVYYCAARDGIPTSRSVESYNYWGQGTQVTV<br>SS |
| BIV #m3F | 76 | QVQLQDSGGGLVQAGGSLRLSCAASGGTFSSIIMAWFRQAPGKEREFVGAVSWSG<br>GTTVYADSVLGRFEISRDSARKSVYLQMNSLKPEDTAVYYCAARPYQKYNWASAS<br>YNVWGQGTQVTVSS<u>EPKTPKPQPAAA</u>QVQLQDSGGGLVQAGGSLRLSCAASGGTF<br>SSIIMAWFRQAPGKEREFVGAVSWSGGTTVYADSVLGRFEISRDSARKSVYLQMN<br>SLKPEDTAVYYCAARPYQKYNWASASYNVWGQGTQVTVSS |

Without linker sequence

| BIV#3 Edir | 77 | QVQLQDSGGGLVQAGGSLRLSCAASGGTFSSIIMAWFRQAPGKEREFVGAVSWSG<br>GTTVYADSVLGRFEISRDSARKSVYLQMNSLKPEDTAVYYCAARPYQKYNWASAS<br>YNVWGQGTQVTVSSQVQLQDSGGGLVQAGGSLRLSCAASGGTFSSIIMAWFRQAP<br>GKEREFVGAVSWSGGTTVYADSVLGRFEISRDSARKSVYLQMNSLKPEDTAVYYC<br>AARPYQKYNWASASYNVWGQGTQVTVSS |
| BIV#12 Bdir | 78 | QVQLQESGGGLVQPGGSLRLSCAASGFEFENHWMYWVRQAPGKGLEWVSTVNTNG<br>LITRYADSVKGRFTISRDNAKYTLYLQMNSLKSEDTAVYYCTKVLPPYSDDSRTN<br>ADWGQGTQVTVSSQVQLQESGGGLVQPGGSLRLSCAASGFEFENHWMYWVRQAPG<br>KGLEWVSTVNTNGLITRYADSVKGRFTISRDNAKYTLYLQMNSLKSEDTAVYYCT<br>KVLPPYSDDSRTNADWGQGTQVTVSS |

TABLE 8

Fractional homologies between the amino acid sequences of anti-mouse serum albumin VHHs of the invention.

| SEQ | MSA21 | MSA24 | MSA210 | MSA212 |
|---|---|---|---|---|
| MSA21 | 1.000 | 0.834 | 0.800 | 0.782 |
| MSA24 | — | 1.000 | 0.782 | 0.791 |
| MSA210 | — | — | 1.000 | 0.903 |
| MSA212 | — | — | — | 1.000 |

TABLE 9

Fractional homologies between anti-TNF-alpha VHHs of the invention

| SEQ | VHH#1A | VHH#7B | VHH#2B | VHH#3E | VHH#3G | VHH#10A | VHH#2G | VHH#1F |
|---|---|---|---|---|---|---|---|---|
| VHH#1A | 1.000 | 0.601 | 0.764 | 0.596 | 0.622 | 0.600 | 0.682 | 0.629 |
| VHH#7B | — | 1.000 | 0.604 | 0.635 | 0.645 | 0.943 | 0.653 | 0.616 |
| VHH#2B | — | — | 1.000 | 0.620 | 0.645 | 0.611 | 0.682 | 0.661 |
| VHH#3E | — | — | — | 1.000 | 0.875 | 0.641 | 0.713 | 0.689 |
| VHH#3G | — | — | — | — | 1.000 | 0.651 | 0.779 | 0.740 |
| VHH#10A | — | — | — | — | — | 1.000 | 0.658 | 0.614 |
| VHH#2G | — | — | — | — | — | — | 1.000 | 0.741 |
| VHH#1F | — | — | — | — | — | — | — | 1.000 |
| VHH#9C | — | — | — | — | — | — | — | — |
| VHH#11E | — | — | — | — | — | — | — | — |
| VHH#10C | — | — | — | — | — | — | — | — |
| VHH#4B | — | — | — | — | — | — | — | — |
| VHH#10D | — | — | — | — | — | — | — | — |
| VHH#12B | — | — | — | — | — | — | — | — |

TABLE 9-continued

Fractional homologies between anti-TNF-alpha VHHs of the invention

| | | | | | | | | |
|---|---|---|---|---|---|---|---|---|
| VHH#9E | — | — | — | — | — | — | — | — |
| VHH#3F | | | | | | | | |

| SEQ | VHH#9C | VHH#11E | VHH#10C | VHH#4B | VHH#10D | VHH#12B | VHH#9E | VHH#3F |
|---|---|---|---|---|---|---|---|---|
| VHH#1A | 0.609 | 0.601 | 0.614 | 0.818 | 0.642 | 0.747 | 0.596 | 0.604 |
| VHH#7B | 0.933 | 0.933 | 0.719 | 0.593 | 0.614 | 0.620 | 0.616 | 0.624 |
| VHH#2B | 0.629 | 0.620 | 0.637 | 0.796 | 0.634 | 0.951 | 0.620 | 0.645 |
| VHH#3E | 0.620 | 0.643 | 0.612 | 0.604 | 0.648 | 0.596 | 0.674 | 0.682 |
| VHH#3G | 0.637 | 0.637 | 0.653 | 0.645 | 0.689 | 0.622 | 0.708 | 0.716 |
| VHH#10A | 0.935 | 0.935 | 0.725 | 0.592 | 0.612 | 0.626 | 0.622 | 0.637 |
| VHH#2G | 0.653 | 0.669 | 0.685 | 0.666 | 0.746 | 0.650 | 0.701 | 0.717 |
| VHH#1F | 0.616 | 0.616 | 0.664 | 0.661 | 0.714 | 0.645 | 0.709 | 0.717 |
| VHH#9C | 1.000 | 0.941 | 0.743 | 0.601 | 0.622 | 0.645 | 0.600 | 0.616 |
| VHH#11E | — | 1.000 | 0.719 | 0.601 | 0.622 | 0.637 | 0.608 | 0.624 |
| VHH#10C | — | — | 1.000 | 0.650 | 0.606 | 0.637 | 0.600 | 0.632 |
| VHH#4B | — | — | — | 1.000 | 0.611 | 0.796 | 0.588 | 0.629 |
| VHH#10D | — | — | — | — | 1.000 | 0.619 | 0.674 | 0.674 |
| VHH#12B | — | — | — | — | — | 1.000 | 0.604 | 0.637 |
| VHH#9E | — | — | — | — | — | — | 1.000 | 0.854 |
| VHH#3F | | | | | | | | 1.000 |

TABLE 10

Percentage homologies between anti-IFN-gamma VHHs of the invention

| | % Homology | | | | | | | | |
|---|---|---|---|---|---|---|---|---|---|
| | MP3D2SRA | MP3A3SR | MP3C5SR | MP3C1SR | MP3G8SR | P3D2BR | MP3H6SRA | MP3B4SRA | MP4E4BR | MP4H8SR |
| MP3D2SRA | X | 96 | 66 | 66 | 66 | 62 | 71 | 71 | 71 | 70 |
| MP3A3SR | — | X | 66 | 66 | 66 | 62 | 72 | 72 | 72 | 71 |
| MP3C5SR | — | — | X | 97 | 98 | 73 | 65 | 65 | 64 | 63 |
| MP3C1SR | — | — | — | X | 98 | 72 | 64 | 64 | 64 | 62 |
| MP3G8SR | — | — | — | — | X | 73 | 65 | 65 | 64 | 63 |
| MP3D2BR | — | — | — | — | — | X | 63 | 63 | 63 | 62 |
| MP3H6SRA | — | — | — | — | — | — | X | 100 | 97 | 97 |
| MP3B4SRA | — | — | — | — | — | — | — | X | 97 | 97 |
| MP4E4BR | — | — | — | — | — | — | — | — | X | 97 |
| MP4H8SR | — | — | — | — | — | — | — | — | — | X |
| MP2F6SR | — | — | — | — | — | — | — | — | — | — |
| MP3D1BR | — | — | — | — | — | — | — | — | — | — |
| MP2B5BR | — | — | — | — | — | — | — | — | — | — |
| MP2C1BR | — | — | — | — | — | — | — | — | — | — |
| MP4A12SR | — | — | — | — | — | — | — | — | — | — |
| MP3F4SRA | — | — | — | — | — | — | — | — | — | — |
| MP3D3BR | — | — | — | — | — | — | — | — | — | — |
| MP3E5BR | — | — | — | — | — | — | — | — | — | — |
| MP3C7SRA | — | — | — | — | — | — | — | — | — | — |
| MP2F1BR | — | — | — | — | — | — | — | — | — | — |
| MP2C5BR | — | — | — | — | — | — | — | — | — | — |
| MP2C10BR | — | — | — | — | — | — | — | — | — | — |
| MP2G5SR | — | — | — | — | — | — | — | — | — | — |
| MP3B1SRA | — | — | — | — | — | — | — | — | — | — |
| MP2F10SR | — | — | — | — | — | — | — | — | — | — |
| MP3A7SRA | — | — | — | — | — | — | — | — | — | — |
| MP4C10SR | — | — | — | — | — | — | — | — | — | — |
| MP4D5BR | — | — | — | — | — | — | — | — | — | — |
| MP3F1SRA | — | — | — | — | — | — | — | — | — | — |
| MP6D6BR | — | — | — | — | — | — | — | — | — | — |
| MP6B1BR | — | — | — | — | — | — | — | — | — | — |
| MP6A8BR | — | — | — | — | — | — | — | — | — | — |
| MP6B12BR | — | — | — | — | — | — | — | — | — | — |
| MP6C11BR | | | | | | | | | | |
| MP6B10BR | | | | | | | | | | |

| | % Homology | | | | | | | |
|---|---|---|---|---|---|---|---|---|
| | MP2F6SR | MP3D1BR | MP2B5BR | MP2C1BR | MP4A12SR | MP3F4SRA | MP3D3BR | MP3E5BR | MP3C7SRA |
| MP3D2SRA | 68 | 69 | 65 | 63 | 64 | 68 | 66 | 67 | 68 |
| MP3A3SR | 70 | 71 | 65 | 63 | 64 | 68 | 66 | 67 | 68 |
| MP3C5SR | 63 | 63 | 60 | 58 | 59 | 64 | 64 | 65 | 66 |
| MP3C1SR | 62 | 62 | 58 | 57 | 58 | 65 | 64 | 64 | 65 |
| MP3G8SR | 63 | 63 | 59 | 58 | 59 | 64 | 64 | 65 | 66 |

TABLE 10-continued

Percentage homologies between anti-IFN-gamma VHHs of the invention

| | | | | | | | | | |
|---|---|---|---|---|---|---|---|---|---|
| MP3D2BR | 63 | 64 | 59 | 58 | 58 | 62 | 61 | 62 | 63 |
| MP3H6SRA | 80 | 81 | 67 | 68 | 67 | 75 | 71 | 73 | 75 |
| MP3B4SRA | 80 | 81 | 67 | 68 | 67 | 75 | 71 | 73 | 75 |
| MP4E4BR | 81 | 82 | 68 | 69 | 68 | 73 | 70 | 71 | 73 |
| MP4H8SR | 81 | 81 | 66 | 66 | 66 | 72 | 69 | 71 | 72 |
| MP2F6SR | X | 94 | 65 | 68 | 64 | 70 | 67 | 69 | 71 |
| MP3D1BR | — | X | 65 | 66 | 65 | 71 | 69 | 71 | 72 |
| MP2B5BR | — | — | X | 95 | 97 | 63 | 64 | 64 | 64 |
| MP2C1BR | — | — | — | X | 95 | 63 | 64 | 64 | 64 |
| MP4A12SR | — | — | — | — | X | 63 | 64 | 64 | 64 |
| MP3F4SRA | — | — | — | — | — | X | 94 | 96 | 97 |
| MP3D3BR | — | — | — | — | — | — | X | 98 | 96 |
| MP3E5BR | — | — | — | — | — | — | — | X | 98 |
| MP3C7SRA | — | — | — | — | — | — | — | — | X |
| MP2F1BR | — | — | — | — | — | — | — | — | — |
| MP2C5BR | — | — | — | — | — | — | — | — | — |
| MP2C10BR | — | — | — | — | — | — | — | — | — |
| MP2G5SR | — | — | — | — | — | — | — | — | — |
| MP3B1SRA | — | — | — | — | — | — | — | — | — |
| MP2F10SR | — | — | — | — | — | — | — | — | — |
| MP3A7SRA | — | — | — | — | — | — | — | — | — |
| MP4C10SR | — | — | — | — | — | — | — | — | — |
| MP4D5BR | — | — | — | — | — | — | — | — | — |
| MP3F1SRA | — | — | — | — | — | — | — | — | — |
| MP6D6BR | — | — | — | — | — | — | — | — | — |
| MP6B1BR | — | — | — | — | — | — | — | — | — |
| MP6A8BR | — | — | — | — | — | — | — | — | — |
| MP6B12BR | — | — | — | — | — | — | — | — | — |
| MP6C11BR | | | | | | | | | |
| MP6B10BR | | | | | | | | | |

| | % Homology | | | | | | | | |
|---|---|---|---|---|---|---|---|---|---|
| | MP2F1BR | MP2C5BR | MP2C10BR | MP2G5SR | MP3B1SRA | MP2F10SR | MP3A7SRA | MP4C10SR | MP4D5BR |
| MP3D2SRA | 71 | 70 | 68 | 67 | 63 | 67 | 68 | 60 | 72 |
| MP3A3SR | 72 | 72 | 69 | 67 | 64 | 66 | 67 | 60 | 73 |
| MP3C5SR | 65 | 65 | 65 | 63 | 63 | 64 | 64 | 61 | 67 |
| MP3C1SR | 64 | 63 | 64 | 62 | 63 | 64 | 65 | 60 | 67 |
| MP3G8SR | 65 | 64 | 65 | 63 | 63 | 65 | 65 | 61 | 66 |
| MP3D2BR | 64 | 63 | 63 | 63 | 64 | 63 | 63 | 63 | 65 |
| MP3H6SRA | 73 | 71 | 73 | 71 | 66 | 75 | 75 | 63 | 71 |
| MP3B4SRA | 73 | 71 | 73 | 71 | 66 | 75 | 75 | 63 | 71 |
| MP4E4BR | 73 | 71 | 73 | 71 | 66 | 75 | 75 | 63 | 72 |
| MP4H8SR | 71 | 71 | 72 | 71 | 64 | 73 | 73 | 62 | 70 |
| MP2F6SR | 67 | 65 | 73 | 71 | 63 | 71 | 70 | 62 | 69 |
| MP3D1BR | 67 | 65 | 70 | 69 | 63 | 71 | 71 | 62 | 68 |
| MP2B5BR | 65 | 63 | 64 | 63 | 60 | 66 | 63 | 57 | 63 |
| MP2C1BR | 63 | 61 | 66 | 65 | 59 | 66 | 63 | 56 | 61 |
| MP4A12SR | 62 | 60 | 63 | 62 | 59 | 65 | 63 | 56 | 61 |
| MP3F4SRA | 69 | 67 | 68 | 68 | 62 | 67 | 69 | 60 | 72 |
| MP3D3BR | 70 | 68 | 67 | 67 | 62 | 67 | 67 | 80 | 70 |
| MP3E5BR | 70 | 68 | 68 | 69 | 63 | 68 | 68 | 60 | 72 |
| MP3C7SRA | 71 | 69 | 69 | 70 | 63 | 69 | 69 | 61 | 72 |
| MP2F1BR | X | 94 | 66 | 67 | 63 | 68 | 67 | 61 | 70 |
| MP2C5BR | — | X | 66 | 67 | 63 | 67 | 65 | 62 | 69 |
| MP2C10BR | — | — | X | 94 | 62 | 68 | 66 | 59 | 67 |
| MP2G5SR | — | — | — | X | 62 | 67 | 65 | 59 | 67 |
| MP3B1SRA | — | — | — | — | X | 66 | 65 | 91 | 67 |
| MP2F10SR | — | — | — | — | — | X | 97 | 61 | 67 |
| MP3A7SRA | — | — | — | — | — | — | X | 61 | 68 |
| MP4C10SR | — | — | — | — | — | — | — | X | 64 |
| MP4D5BR | — | — | — | — | — | — | — | — | X |
| MP3F1SRA | — | — | — | — | — | — | — | — | — |
| MP6D6BR | — | — | — | — | — | — | — | — | — |
| MP6B1BR | — | — | — | — | — | — | — | — | — |
| MP6A8BR | — | — | — | — | — | — | — | — | — |
| MP6B12BR | — | — | — | — | — | — | — | — | — |
| MP6C11BR | | | | | | | | | |
| MP6B10BR | | | | | | | | | |

| | % Homology | | | | | | |
|---|---|---|---|---|---|---|---|
| | MP3F1SRA | MP6D6BR | MP6B1BR | MP6A8BR | MP6B12BR | MP6C11BR | MP6B10BR |
| MP3D2SRA | 65 | 68 | 67 | 66 | 67 | 76 | 70 |
| MP3A3SR | 65 | 67 | 67 | 65 | 66 | 77 | 71 |
| MP3C5SR | 60 | 74 | 63 | 60 | 63 | 70 | 64 |

TABLE 10-continued

Percentage homologies between anti-IFN-gamma VHHs of the invention

| | | | | | | | |
|---|---|---|---|---|---|---|---|
| MP3C1SR | 59 | 73 | 63 | 60 | 62 | 70 | 65 |
| MP3G8SR | 60 | 73 | 63 | 61 | 63 | 71 | 64 |
| MP3D2BR | 58 | 73 | 64 | 60 | 63 | 68 | 67 |
| MP3H6SRA | 69 | 71 | 71 | 68 | 70 | 82 | 70 |
| MP3B4SRA | 69 | 71 | 71 | 68 | 70 | 82 | 70 |
| MP4E4BR | 70 | 71 | 71 | 68 | 70 | 80 | 71 |
| MP4H8SR | 67 | 69 | 70 | 67 | 70 | 79 | 71 |
| MP2F6SR | 66 | 67 | 69 | 68 | 67 | 78 | 69 |
| MP3D1BR | 66 | 67 | 71 | 69 | 69 | 79 | 70 |
| MP2B5BR | 84 | 65 | 63 | 63 | 62 | 70 | 65 |
| MP2C1BR | 85 | 65 | 64 | 63 | 62 | 70 | 65 |
| MP4A12SR | 84 | 64 | 63 | 63 | 62 | 70 | 65 |
| MP3F4SRA | 63 | 67 | 68 | 65 | 65 | 76 | 71 |
| MP3D3BR | 64 | 66 | 66 | 64 | 64 | 75 | 69 |
| MP3E5BR | 64 | 67 | 68 | 65 | 66 | 77 | 71 |
| MP3C7SRA | 64 | 68 | 68 | 66 | 66 | 78 | 71 |
| MP2F1BR | 64 | 68 | 65 | 64 | 64 | 74 | 67 |
| MP2C5BR | 63 | 67 | 64 | 62 | 63 | 73 | 67 |
| MP2C10BR | 66 | 69 | 68 | 64 | 68 | 74 | 73 |
| MP2G5SR | 65 | 67 | 66 | 64 | 66 | 73 | 73 |
| MP3B1SRA | 60 | 67 | 69 | 68 | 69 | 69 | 65 |
| MP2F10SR | 65 | 71 | 66 | 65 | 67 | 77 | 68 |
| MP3A7SRA | 63 | 71 | 65 | 65 | 67 | 77 | 69 |
| MP4C10SR | 58 | 65 | 64 | 63 | 66 | 66 | 63 |
| MP4D5BR | 64 | 69 | 68 | 65 | 67 | 76 | 73 |
| MP3F1SRA | X | 65 | 64 | 64 | 63 | 71 | 68 |
| MP6D6BR | — | X | 70 | 65 | 70 | 77 | 73 |
| MP6B1BR | — | — | X | 78 | 81 | 76 | 71 |
| MP6A8BR | — | — | — | X | 75 | 74 | 66 |
| MP6B12BR | — | — | — | — | X | 73 | 68 |
| MP6C11BR | | | | | | X | 77 |
| MP6B10BR | | | | | | | X |

TABLE 11

Treatment schedule

| Group | Animals | Description | Schedule |
|---|---|---|---|
| 1 | 8 | negative control 1 ip | daily 100 µl PBS i.p. |
| 2 | 8 | negative control 2 rectal | every other day 100 µl PBS rectal for 2 weeks |
| 3 | 8 | negative control 3 intragastric | daily 100 µl PBS intragastric for 14 consecutive days |
| 4 | 8 | positive control 1 dexamethasone | 5 µg i.p. for 7 consecutive days |
| 5 | 8 | positive control 2 IL10 expressing *l. lactis* | applied orally once per day for 14 consecutive days |
| 6 | 8 | bivalent VHH 3F intra-gastric | daily 100 µg bivalent VHH 3F$_2$ intragastric on 14 consecutive days |
| 7 | 8 | bivalent VHH 3F i.p. | daily 100 µg bivalent VHH 3F i.p. for 14 consecutive days |
| 8 | 8 | bivalent VHH 3F rectally | 100 µg bivalent VHH 3F rectally in 100 µl PBS every other day for two weeks |

The invention claimed is:

1. An anti-TNF-alpha polypeptide comprising at least one anti-TNF-alpha single domain antibody comprising:
   (a) an amino acid sequence comprising SEQ ID NO: 1, or
   (b) an amino acid sequence with more than 85% identity to the amino acid sequence of SEQ ID NO: 1, and which comprises an arginine residue at position 103 (numbering according to Kabat).

2. The anti-TNF-alpha polypeptide according to claim 1, comprising an arginine at position 45 and a tryptophan at position 47 (numbering according to Kabat).

3. The anti-TNF-alpha polypeptide according to claim 1, wherein at least one anti-TNF-alpha single domain antibody is humanized.

4. The anti-TNF-alpha polypeptide according to claim 3, wherein at least one anti-TNF-alpha single domain antibody is a humanized *Camelidae* VHH.

5. The anti-TNF-alpha polypeptide according to claim 1, wherein the number of anti-TNF-alpha single domain antibodies is at least two.

6. The anti-TNF-alpha polypeptide according to claim 1 further comprising at least one single domain antibody that binds a serum protein.

7. The anti-TNF-alpha polypeptide according to claim 6 wherein said serum protein is any of serum albumin, serum immunoglobulins, thyroxine-binding protein, transferrin, or fibrinogen.

8. The anti-TNF-alpha polypeptide according to claim 6, wherein the number of single domain antibodies directed against TNF-alpha is at least two.

9. A composition comprising the anti-TNF-alpha polypeptide according to claim 1.

10. A composition comprising the anti-TNF-alpha polypeptide according to claim 2.

11. A composition comprising the anti-TNF-alpha polypeptide according to claim 3.

12. A composition comprising the anti-TNF-alpha polypeptide according to claim 4.

13. A composition comprising the anti-TNF-alpha polypeptide according to claim 5.

14. A composition comprising the anti-TNF-alpha polypeptide according to claim 6.

15. A composition comprising the anti-TNF-alpha polypeptide according to claim 7.

16. A composition comprising the anti-TNF-alpha polypeptide according to claim 8.

* * * * *